US012560619B2

(12) United States Patent
Sorek et al.

(10) Patent No.: US 12,560,619 B2
(45) Date of Patent: **\*Feb. 24, 2026**

(54) METHODS AND COMPOSITIONS FOR DIAGNOSING BRAIN INJURY OR NEURODEGENERATION

(71) Applicant: BRAINBOX SOLUTIONS, INC., Richmond, VA (US)

(72) Inventors: Rachel Sorek, Zafaria (IL); Keren Jakobi, Tel Aviv (IL); Donna Edmonds, Lancaster, VA (US)

(73) Assignee: BRAINBOX SOLUTIONS, INC., Richmond, VA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/735,006

(22) Filed: Jun. 5, 2024

(65) Prior Publication Data

US 2025/0067754 A1     Feb. 27, 2025

Related U.S. Application Data

(63) Continuation of application No. 16/299,588, filed on Mar. 12, 2019, now Pat. No. 12,038,446, which is a continuation of application No. 15/547,252, filed as application No. PCT/IL2016/050108 on Feb. 1, 2016, now abandoned.

(60) Provisional application No. 62/112,189, filed on Feb. 5, 2015.

(51) Int. Cl.
| | |
|---|---|
| *G01N 33/68* | (2006.01) |
| *C07K 14/47* | (2006.01) |
| *G01N 33/543* | (2006.01) |
| *G01N 33/96* | (2006.01) |

(52) U.S. Cl.
CPC ......... *G01N 33/6896* (2013.01); *C07K 14/47* (2013.01); *G01N 33/54366* (2013.01); *G01N 33/96* (2013.01); *G01N 2800/28* (2013.01); *G01N 2800/52* (2013.01); *G01N 2800/56* (2013.01)

(58) Field of Classification Search
CPC ......... G01N 33/6896; G01N 33/54366; G01N 33/96; G01N 2800/28; G01N 2800/52; G01N 2800/56; C07K 14/47
See application file for complete search history.

(56) References Cited

U.S. PATENT DOCUMENTS

| | | | |
|---|---|---|---|
| 6,235,489 B1 | 5/2001 | Jackowski | |
| 6,884,591 B2 | 4/2005 | Janigro et al. | |
| 7,144,708 B2 | 12/2006 | Janigro et al. | |
| 7,396,654 B2 | 7/2008 | Hayes et al. | |
| 7,456,027 B2 | 11/2008 | Wang et al. | |
| 8,460,888 B2 | 6/2013 | Lafaye et al. | |
| 8,492,107 B2 | 7/2013 | Wang et al. | |
| 8,557,526 B2 | 10/2013 | Ottens et al. | |
| 8,663,911 B2 | 3/2014 | Vojdani | |
| 8,778,343 B2 | 7/2014 | Kayed | |
| 9,194,867 B2 | 11/2015 | Vojdani | |
| 9,547,014 B2 | 1/2017 | Travis et al. | |
| 9,810,698 B2 | 11/2017 | Wang et al. | |
| 10,041,959 B2 | 8/2018 | Wang et al. | |
| 10,330,689 B2 | 6/2019 | Wang et al. | |
| 10,534,003 B2 | 1/2020 | Everett et al. | |
| 11,143,662 B2 * | 10/2021 | Edmonds ........... | G01N 33/6896 |
| 11,499,982 B2 | 11/2022 | Everett et al. | |
| 12,038,446 B2 * | 7/2024 | Sorek ................. | G01N 33/6896 |
| 2003/0040660 A1 | 2/2003 | Jackowski et al. | |
| 2005/0260770 A1 | 11/2005 | Cohen et al. | |
| 2011/0177974 A1 | 7/2011 | Wang et al. | |
| 2013/0022982 A1 | 1/2013 | Wang et al. | |
| 2014/0045713 A1 | 2/2014 | Everett et al. | |
| 2014/0303041 A1 | 10/2014 | Hayes et al. | |
| 2014/0342381 A1 | 11/2014 | Hayes | |
| 2015/0004169 A1 | 1/2015 | Kayed | |
| 2015/0031048 A1 | 1/2015 | Van Eyk et al. | |
| 2015/0118218 A1 | 4/2015 | Travis et al. | |
| 2015/0119273 A1 | 4/2015 | Goldstein et al. | |
| 2015/0141528 A1 | 5/2015 | Larner | |
| 2015/0247867 A1 | 9/2015 | Curdt et al. | |
| 2015/0268252 A1 | 9/2015 | Svetlov et al. | |
| 2017/0146555 A1 | 5/2017 | Wang et al. | |
| 2018/0024145 A1 | 1/2018 | Sorek et al. | |
| 2019/0195893 A1 | 6/2019 | Sorek et al. | |
| 2019/0310265 A1 | 10/2019 | Van Eyk et al. | |
| 2023/0077876 A1 | 3/2023 | Everett et al. | |

FOREIGN PATENT DOCUMENTS

| | | |
|---|---|---|
| WO | 2002008755 A2 | 1/2002 |
| WO | 2003/042701 A1 | 3/2003 |
| WO | 2010148391 A2 | 12/2010 |
| WO | 2013104720 A2 | 7/2013 |
| WO | 2015009907 A1 | 1/2015 |

(Continued)

OTHER PUBLICATIONS

Cohen, Irun R., "Real and artificial immune systems: computing the state of the body," Nature Reviews Immunology, Jul. 2007, vol. 7, pp. 569-574.

(Continued)

*Primary Examiner* — Olga N Chernyshev

(74) *Attorney, Agent, or Firm* — Greenberg Traurig, LLP; Melissa Hunter-Ensor; Leslie Serunian

(57) ABSTRACT

Methods and compositions for diagnosing brain injury, neurodegeneration; or a predisposition thereto, in a subject are provided. Particularly, the present invention relates to specific antigen antibody reactivities useful in diagnosing brain injury, neurodegeneration or a predisposition thereto, in a subject.

10 Claims, 7 Drawing Sheets

Specification includes a Sequence Listing.

(56)                     References Cited

FOREIGN PATENT DOCUMENTS

| WO | 2015157390 A1 | 10/2015 |
| WO | 2016055148 A2 | 4/2016 |
| WO | 2016087611 A1 | 6/2016 |
| WO | 2017008894 A1 | 1/2017 |

OTHER PUBLICATIONS

Kanter et al., "Lipid microarrays identify key mediators of autoimmune brain inflammation," Nature Medicine, Jan. 2006, vol. 12, No. 1, pp. 138-143.

Merbl et al., "Newborn humans manifest autoantibodies to defined self molecules detected by antigen microarray informatics," The Journal of Clinical Investigation, Mar. 2007, vol. 117, No. 3, pp. 712-718.

Quintana et al., "Antigen-Chip Technology for Accessing Global Information about the State of the Body," Lupus, 2006, vol. 15, No. 7, pp. 428-430.

Quintana et al., "Autoantibody Patterns in Diabetes-prone NOD Mice and in Standard C57BL/6 Mice," Journal of Autoimmunity, Nov. 2001, vol. 17, No. 3, pp. 191-197.

Quintana et al., "Cluster analysis of human autoantibody reactivities in health and in type 1 diabetes mellitus: a bio-informatic approach to immune complexity," Journal of Autoimmunity, Aug. 2003, vol. 21, No. 1, pp. 65-75.

Quintana et al., "The natural autoantibody repertoire and autoimmune disease," Biomedicine & Pharmacotherapy, 2004, vol. 58, No. 5, pp. 276-281.

Robinson et al., "Autoantigen microarrays for multiplex characterization of autoantibody responses," Nature Medicine, Mar. 2002, vol. 8, No. 3, pp. 295-301.

Robinson et al., "Protein microarrays guide tolerizing DNA vaccine treatment of autoimmune encephalomyelitis," Nature Biotechnology, Sep. 2003, vol. 21, No. 9, pp. 1033-1039.

Zafonte et al., "Effect of Citicoline on Functional and Cognitive Status Among Patients With Traumatic Brain Injury: Citicoline Brain Injury Treatment Trial (COBRIT)," JAMA, Nov. 21, 2012, vol. 308, No. 19, pp. 1993-2000.

Babcock, L. et al., "Ability of S100B to predict severity and cranial CT results in children with TBI," Brain Injury, vol. 26, No. 11, pp. 1372-1380 (2012).

Berger, R. et al., "Multiplex Assessment of Serum Biomarker Concentrations in Well-Appearing Children With Inflicted Traumatic Brain Injury," Pediatric Research, vol. 65, No. 1, pp. 97-102 (2009).

Biberthaler, P. et al., "Serum S-100B Concentration Provides Additional Information for the Indication of Computed Tomography in Patients After Minor Injury," Shock, vol. 25, No. 5, pp. 446-453 (2006).

Ingebrigtsen, T. et al., "The clinical value of serum S-100 protein measurements in minor head injury: a Scandinavian multicentre study," Brain Injury, vol. 14, No. 12, pp. 1047-1055 (2000).

Jeter, C. et al., "Biomarkers for the Diagnosis and Prognosis of Mild Traumatic Brain Injury/Concussion," Journal of Neurotrauma, vol. 30, pp. 657-670 (2013).

Mondello, S. et al., "Glial Neuronal Ratio: A Novel Index for Differentiating Injury Type in Patients with Severe Traumatic Brain Injury," Journal of Neurotrauma, vol. 29, pp. 1096-1104 (2012).

Papa, L. et al., "[Elevated] Levels of Serum Glial Fibrillary Acidic Protein Breakdown Products in Mild and Moderate Traumatic Brain Injury are Associated With Intracranial Lesions and Neurosurgical Intervention," Ann. Emerg. Med., vol. 59, No. 6, pp. 1-24 (2012).

Papa, L. et al., Serum levels of ubiquitin C-terminal hydrolase distinquish mild traumatic brain injury from trauma controls and are elevated in mild and moderate traumatic brain injury patients with intracranial lesions and neurosurgical intervention, J. Trauma, vol. 72, No. 5, pp. 1335-1344 (2012).

Rodrigues, E. et al., "Increased serum brain derived neurotrophic factor (BDNF) following isolated severe traumatic brain injury in humans," Abstract No. 0196, Brain Injury, 22 (Supplement 1), p. 165 (2008).

Rostami, E. et al., "Alteration in BDNF and its receptors, full-length and truncated TrkB and p75NTR following penetrating traumatic brain injury," Brain Research, vol. 1542, pp. 195-205 (2014).

Rostami, E et al., Proteomic-based identification of injury-specific patterns of biomarkers following different types of TBI, Presentation Abstract, Presentation date: Nov. 15, 2010, XP009193994, 2 pages.

Griesbach, G. et al., "Alterations in BDNF and Synapsin I within the Occipital Cortex and Hippocampus after Mild Traumatic Brain Injury in the Developing Rat: Reflections of Injury-Induced Neuroplasticity," Journal of Neurotrauma, vol. 19, No. 7, pp. 803-814 (2002).

Horakova, D. et al., "Environmental Factors Associated with Disease Progression after the First Demyelinating Event: Results from the Multi-Center SET Study," Plos One, vol. 8, No. 1, Jan. 8, 2013, p. e53996 (8 pages).

Liu, Y. et al., "Development of Recombinant Antigen Array for Simultaneous Detection of Viral Antibodies," PLOS ONE, vol. 8, No. 9, Sep. 13, 2013, p. e73842 (9 pages).

Supplementary Partial European Search Report in corresponding European Patent Application No. 16 74 6229, dated May 16, 2018 (5 pages).

Provisional Opinion in corresponding European Patent Application No. 16 74 6229, dated May 16, 2018 (6 pages).

International Search Report and Written Opinion for corresponding PCT/IL2016/050108 dated Jun. 15, 2016 (14 pages).

Marchi, N. et al., "Consequences of Repeated Blood-Brain Barrier Disruption in Football Players," PLoS ONE 8(3):e56805. doi: 10.1371/journal.pone.0056805, Mar. 6, 2013.

Ngankam, L. et al., "Immunological markers of severity and outcome of traumatic brain injury," Zhurnal nevrologii i psikhiatrii imeni SS Korsakova/Ministerstvo zdravookhraneniia i meditskinskoi promyshlennosti Rossiiskioi Federastsii, Vserossiiskoe obschestvo nevrologov [i] Vesrossiiskoe obshchestvo psikhiatrov, 111(7), pp. 61-65, Dec. 31, 2010 (Dec. 31, 2010). Abstract in English Provided (1 page).

Xu et al., BMC Neurology, 2012, 12(87):1-7.

Zhang, Y. and Popovich, P., "Roles of autoantibodies in central nervous system injury," Discovery Medicine, vol. 11(60), pp. 395-402. (http://www.discoverymedicine.com/Yi-Zhang/2011/05/10/roles-of-autoantibodies-in-central-nervous-system-injury).

Zhang, Z. et al., "Human Traumatic Brain Injury Induces Autoantibody Response against Glial Fibrillary Acidic Protein and Its Breakdown Products," PLoS ONE 9(3): e92698. doi: 10.1371/journal pne. 0092698, Mar. 24, 2014.

Buki et al., "Minor and Repetitive Head Injury", Advances and Technical Standards in Neurosurgery 42, 2015, pp. 147-192, Springer International Publishing Switzerland.

Ichkova et al., "New Biomarker Stars for Traumatic Brain Injury", Journal of Cerebral Blood Flow & Metabolism, 2017, vol. 37(10), 3276-3277.

Ke et al., "Increased Expression of Small Heat Shock Protein aB-Crystallin After Intracerebral Hemorrhage in Adult Rats", J. Mol. Neurosci, 2013, 51:159-169, Springer Science+Business Media New York.

Lumpkins et al., "Glial Fibrillary Acidic Protein is Highly Correlated with Brain Injury", The Journal of Trauma, 2008, 65, pp. 778-784.

Martinez et al., "Type-Dependent Oxidative Damage in Frontotemporal Lobar Degeneration: Cortical Astrocytes are Targets of Oxidative Damage", j Neuropathol Exp Neurol, vol. 67, No. 12, Dec. 2008, pp. 1122-1136.

McMahon et al., "Measurement of the Glial Fibrillary Acidic protein and its Breakdown Products GFAP-BDP Biomarker for the Detection of Traumatic Brain Injury Compared to Computed Tomography and Magnetic Resonance Imaging", Journal of Neurotrauma, 35:527-533, Apr. 15, 2015.

(56)        References Cited

OTHER PUBLICATIONS

Newcombe et al., "Distribution of Glial Fibrillary Acidic Protein in Gliosed Human White Matter", Journal of Neurochemistry, 47, 1986, pp. 1713-1719.

Okonkwo et al., "GFAP-BDP as an Acute Diagnostic Marker in Traumatic Brain Injury: Results from the Prospective Transforming Research and Clinical Knowledge in Traumatic Brain Injury Study", Journal of Neurotrauma, 30:1490-1497, Sep. 1, 2013.

Papa et al., "Elevated Levels of Serum Glial Fibrillary Acidic Protein Breakdown Products in Mild and Moderate Traumatic Brain Injury are Associated with Intracranial Lesions and Neurosurgical Intervention", Annals of Emergency Medicine, vol. 59, No. 6, Jun. 2012, pp. 471-483.

Pelinka et al., "Glial Fibrillary Acidic Protein in Serum After Traumatic Brain Injury and Multiple Trauma", The Journal of Trauma, 2004, 57:1006-1012.

Pelinka et al., "GFAP Versus S100B in Serum after Traumatic Brain Injury: Relationship to Brain Bamage and Outcome", Journal of Neurotrauma, vol. 21, No. 11, 2004, pp. 1553-1561.

Rohn et al., "Caspase-Cleaved Glial Fibrillary Acidic Protein within Cerebellar White Matter of the Alzheimer's Disease Brain", Int J Clin Pathol, 2013, 6(1), pp. 41-48.

Shen et al., "Addressing the Needs of Traumatic Brain Injury with Clinical Proteomics", Clinical Proteomics, 2014, 11:11, (13 pages).

Vasquez et al., "Creatine Kinase BB and Neuron-Specific Enolase in Cerebrospinal Fluid in the Diagnosis of Brain Insult", The American Journal of Forensic Medicine and Pathology, 16(3), pp. 210-214, 1995.

Yang et al., "Glial Fibrillary Acidic Protein: from Intermediate Filament Assembly and Gliosis to Neurobiomarker", Trends in Neuroscience, Jun. 2015, vol. 38, No. 6, pp. 364-374.

Zhang et al., "Human Traumatic Brain Injury Induces Autoantibody Response Against Glial Fibrillary Acidic Protein and Its Breakdown Products", PLOS One, Mar. 2014, vol. 9, Issue 3, (16 pages).

Zoltewicz et al., "Characterization of Antibodies that Detect Human GFAP after Traumatic Brain Injury", Biomarker Insights, 2012:7, pp. 71-79.

* cited by examiner

METHODS AND COMPOSITIONS FOR DIAGNOSING BRAIN INJURY OR NEURODEGENERATION

CROSS REFERENCE TO RELATED APPLICATIONS

This application is a continuation of U.S. patent application Ser. No. 16/299,588, filed on Mar. 12, 2019, now U.S. Pat. No. 12,038,446, issued on Jul. 16, 2024, which is a continuation of U.S. patent application Ser. No. 15/547,252, filed on Jul. 28, 2017, which is a national stage entry under 35 U.S.C. § 371 of International PCT Application No.: PCT/IL2016/050108, filed on Feb. 1, 2016, designating the United States and published in English, which claims priority to and benefit of U.S. Provisional Application No. 62/112,189, filed on Feb. 5, 2015, the contents of all of which are incorporated herein by reference in their entireties.

SEQUENCE LISTING

This application contains a Sequence Listing which has been submitted electronically in XML format and is hereby incorporated by reference in its entirety. The Sequence Listing XML file, created on Jun. 5, 2024, is named 151066-010308USCON2_SL.xml and is 213,123 bytes in size.

FIELD OF THE INVENTION

The present invention relates to methods and compositions for diagnosing brain injury, neurodegeneration; or a predisposition thereto, and more specifically to clinical methods for determining the presence and type of brain injury or neurodegeneration.

BACKGROUND OF THE INVENTION

Brain injuries are complex and can have multiple severe clinical outcomes. Injury of the brain and spinal cord can result from head trauma, stroke, traumatic birth, heart surgery, cardiac arrest and patients requiring cardiovascular support with ventricular assist devices or extracorporeal membrane oxygenation (ECMO).

About 1.7 Million Americans sustain a traumatic brain injury (TBI) each year, ranging from mild to severe, and this is in addition to about 360,000 soldiers involved in combat operations and public safety workers surviving terrorist attacks who develop mild TBI secondary to explosive (concussive) blasts. It contributes about 30% of all injury related deaths and costs about $60 B per year. At least 230,000 people are hospitalized due to TBI and survive; more than a million are treated in an emergency department (ED) for TBI and 80,000 to 90,000 Americans experience long-term disability from TBIs.

Recent study was conducted to determine the dimensions of TBI evaluation in US emergency department. TBI was evaluated during 4.8 million visits per year; and head CT scan was performed in 82% of TBI evaluations (3.9 million visits per year). TBI was diagnosed in 52% of evaluations (2.5 million visits per year). Among those who received head CT scans, 9% had CT evidence of traumatic abnormalities. Among patients evaluated for TBI who had a Glasgow Coma Scale score recorded, 94.5% were classified as having mild TBI, 2.1% as moderate TBI, and 3.5% as severe TBI. Among patients with International Classification of Diseases, Ninth Revision, Clinical Modification, codes permitting the calculation of head Abbreviated Injury Scale scores 9.0%, 85.0%, 2.5%, 3.2%, 0.3%, and 0% had head Abbreviated Injury Scale scores of 1, 2, 3, 4, 5, and 6, respectively. Of patients evaluated for TBI, 31% had other head/face/neck injuries, 10% had spine and back injuries, 7% had torso injuries, and 14% had extremity injuries (Korley et al., Sep. 10, 2015, J Head Trauma Rehabil)

TBI is the result of a blunt blow, jolt or blast overpressure to the head that disrupts brain function. The subset of mild TBI (mTBI) has represented a harder segment of TBI to diagnose. The severity of head injuries range from a brief change in mental status or consciousness to extended unconsciousness and amnesia. In severe or multiple concussion cases, personality changes can occur with devastating results. Cognitive decline is recognized as part of the post injury syndrome.

Proper treatment of TBI injury requires an accurate diagnosis of the structures affected. The mechanisms of injury in TBI cause a variety of abnormalities in the peripheral vestibular mechanisms, central vestibular structures, ocular-motor tracts, cerebellum, as well as all portions of the brain communicating with these structures. The onset of vestibular deficits generally occurs within seven to ten days post injury. While reported symptoms of dizziness resolve after three months, 15% have persistent symptoms one year later.

At present, one of the rather subjective and not totally effective diagnostic procedures when traumatic brain injury is suspected involves a number of examining techniques. The patient receives a neurological examination which may consist of the following: 1) mental status, 2) motor function, 3) sensory examination, 4) deep tendon reflexes, 5) station, gait, and equilibrium, and 6) cranial nerve function. The mental status examination may include: a) level of consciousness, b) short and long term memory, c) knowledge of patient and place and d) questions about symptoms: headache, dizziness, blurry vision, etc. In addition, the patient may also have radiological studies which could include CT scan of the head, MRI, PET scan. It has been reported that in the early stages of (especially mild) traumatic brain injury, the imaging techniques may not be sufficiently sensitive to detect an abnormality. Furthermore, the patient's cognitive skills may not be impaired initially, and there may be few, if any, symptoms. Patients are often observed over 24-48 hours and are awakened at regular intervals (e.g., every 3-4 hours) to assure that they are able to be aroused. Narcotics for headache or other pain are not given, so that their effects do not cloud the issue of the patient's arousal state. A computerized test which determines level of cognition and reaction time is often employed with repetitive examinations.

One of the problems with this approach in diagnosing potential traumatic brain injuries is that it is not one which always provides precise, timely, objective information. It is also subject to individual variations from person-to-person. Further, if the person is asymptomatic at the time, the conclusion might be that there is no problem, and the individual might be encouraged to go back to normal activities. Such guidance could potentially be injurious to the person's health and could even lead to fatal consequences.

Once a patient has been diagnosed with a brain injury, it becomes important to treat the patient in a timely, effective manner in order to minimize the risk of permanent injury or death.

In spite of the foregoing known procedures, there remains a very real and substantial need for a method of early and effective determination as to whether an individual has suffered a brain injury, how severe it might be, and upon finding the presence of such an injury, effectively treating the patient.

SUMMARY OF THE INVENTION

The present invention provides methods and kits for diagnosing brain injury or neurodegeneration. The present invention further provides antigen probe arrays for practicing such a diagnosis, and antigen probe sets for generating such arrays.

The antigen probe sets of the present invention can be used to profile the antibody response to said antigens in patients suffering from brain injury or neurodegenerative disease, due to disruption of any or all components of the anatomic structure and the ability to detect elements which cross the blood brain barrier. This antibody response profile can be used for the diagnosis, monitoring and management of brain injury. According to some embodiments, the antibody profile reflects the patient status at time of injury. The profile of the antibody response can be measured on any platform including but not limited to a micro array or any array chip.

The present invention is based, in part, on the unexpected results obtained when testing the antibody reactivity of patients suffering from brain injury compared to healthy controls. Surprisingly, differential immunoglobulin G (IgG) and IgM reactivities to specific antigens were found in the tested brain injury patients, compared to healthy controls. The present invention is also based on the discovery that analysis of the pattern of an individual's antibody response to specific brain related molecules in combination with markers of immune response provides a novel and reliable method of ascertaining the nature and extent of brain injury and of other neurodegenerative conditions. Thus, the present invention provides unique antigens, indicative to brain injury. The present invention further provides antigen-autoantibody reactivity patterns relevant to brain injury. In particular embodiments, the present invention provides highly specific, reliable, accurate and discriminatory assays for diagnosing and monitoring brain injury, based on the indicative antigens, or on reactivity patterns thereof.

According to some embodiments, the 'pre-existing state' of the patient status at time of injury is monitored.

Thus, according to some embodiments of the invention, there are provided novel methods for diagnosing and monitoring the progression of brain injury. According to some embodiments of the invention, the methods comprise determining the reactivity of antibodies in a sample obtained or derived from a subject to at least one antigen as described herein. The methods of the invention further comprise a step of comparing the reactivity of antibodies in the sample to the at least one antigen to a control reactivity to said at least one antigen. According to certain embodiments, a significantly differential reactivity of the antibodies in the sample compared to the reactivity of the healthy control, or to the reactivity of baseline samples from the same patient, is an indication that the subject is afflicted with brain injury.

According to certain embodiments, the baseline samples from the same patient may be used [for measurements over time] to predict progression, resolution of event or remission of disease course.

According to certain embodiments, the methods of the present invention can discriminate which patients with brain injury require a head CT scan to rule out intracranial hemorrhage versus concussion alone. If implemented as an initial response (e.g., in the emergency department (ED) setting) or later (e.g., neurology department), the methods of present invention would decrease head CT scan utilization, decreasing health care costs and radiation exposure.

Thus, according to a first aspect, the present invention provides a method of diagnosing brain injury in a subject, the method comprising the steps of obtaining a sample from the subject, determining the reactivity of antibodies in the sample to at least one antigen selected from the groups consisting of SEQ ID NOs: 1-115, isoforms thereof, post-translationally modified forms thereof, fragments thereof, or combinations of any of the foregoing; and comparing the reactivity of antibodies in the sample to a reactivity of a healthy control; wherein a significantly different reactivity of the antibody or antibodies in the sample compared to the reactivity of the healthy control is an indication that the subject is afflicted with brain injury.

In certain embodiments, the at least one antigen is selected from the groups consisting of SEQ ID NOs: 2, 14, 28, 42, 85, and 86, or any combination thereof.

In certain embodiments, said method further comprising measuring the levels of one or more biomarkers in the sample; and comparing the levels of the one or more biomarkers with predefined levels of the same biomarkers that correlate to a subject having brain injury and predefined levels of the same biomarkers that correlate to a healthy control, wherein a correlation to one of the predefined levels provides the diagnosis.

In certain embodiments, said brain injury is selected from the group consisting of: concussions, chronic traumatic encephalopathy, mild traumatic brain injuries, moderate traumatic brain injuries, severe traumatic brain injuries, head trauma, concussive blasts and brain neurodegenerative condition.

In certain embodiments, said brain injury causes disruption of the blood-brain barrier.

In certain embodiments, the brain neurodegenerative condition further comprises loss of memory or motor function and cognitive decline.

In certain embodiments, the neurodegenerative condition is selected from the group consisting of: Alzheimer's disease, Huntington's disease, Parkinson's disease, demyelinating disease, HTLV-1-associated myelopathy (HAM), multiple sclerosis (MS), amyotrophic lateral sclerosis (ALS), pathological neurological symptoms after injury or trauma, encephalopathy and viral encephalopathy.

In certain embodiments, a significantly higher reactivity of the antibodies in the sample compared to the reactivity of the healthy control is an indication that the subject is of increased likelihood to be afflicted with brain injury. In other certain embodiments, where the reactivity of the antibodies in the sample compared to the reactivity of the healthy control is not significantly higher, where the reactivity of the antibodies in the sample compared to the reactivity of the healthy control is the same, where the reactivity of the antibodies in the sample compared to the reactivity of the healthy control is lower or where the reactivity of the antibodies in the sample compared to the reactivity of the healthy control is significantly lower, it is an indication that the subject is of decreased likelihood to be afflicted with brain injury. Each possibility represents a separate embodiment of the present invention.

In certain embodiments of the methods of the present invention, the methods are preceded by a step comprising obtaining or deriving a sample from the subject. In certain embodiments, the sample is obtained or derived from the subject by non-invasive means or methods.

In certain embodiments, said obtaining is carried out within two hours of the head trauma. In certain embodiments, said obtaining is carried out within four hours of the head trauma. In certain embodiments, said obtaining is carried out within 24 hours of the head trauma. In certain embodiments, said obtaining is carried out within 72 hours of the head trauma. In certain embodiments, said obtaining is carried out during the post-acute care.

In certain embodiments, the subject is conscious at the time of said obtaining.

In certain embodiments, determining the reactivity of antibodies in the sample to a plurality of antigens produces a reactivity pattern, used for the diagnosis of brain injury in the subject. Thus, according to exemplary embodiments of the invention, the reactivity pattern of antibodies in the sample to the plurality of antigens is compared to the reactivity pattern of antibodies in a sample corresponding to healthy control subjects to said plurality of antigens, wherein a significant difference between the reactivity pattern of the sample and the reactivity pattern of healthy controls indicates that the subject is afflicted with, or in other embodiments has increased likelihood for having brain injury. Conveniently, the reactivity patterns are calculated and compared using e.g. learning and pattern recognition algorithms as described herein.

According to another embodiment, the reactivity of antibodies comprises IgG and IgM reactivities. According to another embodiment, the significantly higher reactivity of the antibodies in the sample comprises differential IgG and/or IgM reactivities. According to another embodiment, the increased IgM reactivity is of at least one antigen selected from the group consisting of SEQ ID NOs: 1-115, isoforms thereof, post-translationally modified forms thereof, fragments thereof, or combinations of any of the foregoing. According to another embodiment, the increased IgG reactivity is of at least one antigen selected from the group consisting of SEQ ID NOs: 1-115, isoforms thereof, post-translationally modified forms thereof, fragments thereof, or combinations of any of the foregoing. Each possibility represents a separate embodiment of the invention.

According to additional embodiments of the methods of the present invention, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample. In certain embodiments, the sample is obtained or derived from the subject by non-invasive means or methods.

According to certain embodiments of the methods of the present invention, the control is selected from the group consisting of a sample from at least one healthy individual, a baseline sample from same subject, a panel of control samples from a set of healthy individuals, and a stored set of data from healthy individuals. Each possibility represents a separate embodiment of the invention. Typically, a healthy individual is a subject not afflicted with brain injury. In another embodiment, a healthy individual is a subject not afflicted with neurodegenerative disease.

According to another embodiment, the method comprises determining the reactivity of antibodies in the sample to a plurality of antigens.

According to another embodiment, the method comprises determining the reactivity of antibodies in the sample to at least one antigen selected from the group consisting of SEQ ID NOs: 1-115, isoforms thereof, post-translationally modified forms thereof, fragments thereof, or combinations of any of the foregoing. According to another embodiment, the method comprises determining the reactivity of antibodies in the sample to at least two antigens selected from the group consisting of SEQ ID NOs: 1-115, isoforms thereof, post-translationally modified forms thereof, fragments thereof, or combinations of any of the foregoing.

According to another embodiment, the plurality of antigens is used in the form of an antigen probe set, an antigen array, or an antigen chip.

According to another aspect, the present invention provides an antigen probe set comprising a plurality of antigen probes selected from the group consisting of SEQ ID NOs: 1-115, isoforms thereof, post-translationally modified forms thereof, fragments thereof, or combinations of any of the foregoing. In another embodiment, the antigen probe set comprises the antigen probes of SEQ ID NOs: 1-115, isoforms thereof, post-translationally modified forms thereof, fragments thereof, or combinations of any of the foregoing.

According to another aspect, the present invention provides an article of manufacture comprising the antigen probe set described above.

In certain embodiments, the article of manufacture, further comprising one or more biomarkers selected from the group consisting of glial fibrillary acidic protein (GFAP), Synuclein beta (Sncb), Metallothionein-3 (MT3), Neurogranin (NRGN), intercellular adhesion molecule-5 (ICAM5) and Brain derived neurotrophic factor (BDNF), or citrullinated forms thereof.

In certain embodiments, the article of manufacture is in the form of an antigen probe array or in the form of an antigen chip or in the form of a dipstick or in the form of a lateral flow test or in the form of an ELISA plate or in the form of a Quanterix system, an Agilent Plate reader, a Meso Scale Diagnostics platform, or any other platform known to those skilled in the art. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use of the kit for diagnosing brain injury.

According to another aspect, there is provided use of the at least one antigen selected from the group consisting of: SEQ ID NOs: 1-115, isoforms thereof, post-translationally modified forms thereof, fragments thereof, or combinations of any of the foregoing; for the preparation of a diagnostic kit for diagnosing brain injury in a subject. Each possibility represents a separate embodiment of the invention. The diagnostic kit is, in some embodiments, useful for determining the reactivity of antibodies in a sample, thereby determining the reactivity pattern of the sample to the at least one antigen. In some embodiments, a significant difference (e.g., increase) between the reactivity pattern of the sample compared to a reactivity pattern of a control sample is an indication for brain injury.

According to another aspect, there is provided a method for qualifying brain injury status in a subject the method comprising the steps of: obtaining a sample from the subject;

determining the reactivity of antibodies in the sample to at least one antigen selected from the group consisting of SEQ ID NOs: 1-115, isoforms thereof, post-translationally modified forms thereof, fragments thereof, or combinations of any of the foregoing; and comparing the reactivity of antibodies in the sample to a predefined reactivity that correlate to one or more brain injury statuses selected from the group consisting of having brain injury, not having brain injury, predisposition to brain injury, sub-acute brain injury, acute brain injury, post-acute brain injury, progressing brain injury, regressing brain injury, subclinical brain injury, mild brain injury, moderate brain injury, severe brain injury and chronic brain injury, wherein a correlation to one of the predefined reactivities determines the brain injury status of the subject.

In certain embodiments, said method further comprising measuring the levels of one or more biomarkers in the sample; and comparing the levels of the one or more biomarkers with predefined levels of the same biomarkers that correlate to one or more brain injury statuses, wherein a correlation to one of the predefined levels determines the brain injury status of the subject.

According to another aspect, there is provided a method of detecting recovery from brain injury in a subject, the method comprising the steps of: obtaining a sample from the subject; determining the reactivity of antibodies in the sample to at least one antigen selected from the group consisting of SEQ ID NOS: 10, 44, 61, 66, 102, 104, isoforms thereof, post-translationally modified forms thereof, fragments thereof, or any combinations thereof; and comparing the reactivity of antibodies in the sample to a predefined reactivity threshold; wherein a significantly different reactivity of the antibodies in the sample compared to the predefined reactivity threshold is indicative of recovery from brain injury in said subject.

In certain embodiments, said method further comprising measuring the levels of one or more biomarkers in the sample; and comparing the levels of the one or more biomarkers with predefined levels of the same biomarkers that correlates with recovery from brain injury, wherein a correlation to one of the predefined levels is indicative of recovery from brain injury of the subject.

In certain embodiments, the one or more biomarkers is selected from the group consisting of glial fibrillary acidic protein (GFAP), Synuclein beta (Sncb), Metallothionein-3 (MT3), Neurogranin (NRGN), intercellular adhesion molecule-5 (ICAM5) and Brain derived neurotrophic factor (BDNF), or citrullinated forms thereof.

In certain embodiments, a combination of one or more antibodies and one or more biomarkers are used.

According to certain embodiments, the comparison is conducted by using at least one classifier algorithm.

According to certain embodiments, the at least one classifier algorithm is selected from the group consisting of a decision tree classifier, logistic regression classifier, nearest neighbor classifier, neural network classifier, Gaussian mixture model (GMM), Support Vector Machine (SVM) classifier, nearest centroid classifier, linear regression classifier, linear discriminant analysis (LDA) classifier, quadratic discriminant analysis (QDA) classifier and random forest classifier.

Other objects, features and advantages of the present invention will become clear from the following description and drawings.

Serum samples obtained from TBI patients at time 0 (t0, N=85) were compared with serum samples obtained from healthy control (HC, N=21). The analysis was based on 464 iChip features (232 antigen, IgM and IgG) and four ELISA features. iChip data is based on average of two block replicates, following correction procedure. ELISA features were selected based on data availability; only features with data available for >80% of the iChip samples were used. Samples with missing ELISA data were removed from the analysis.

Figure 7:
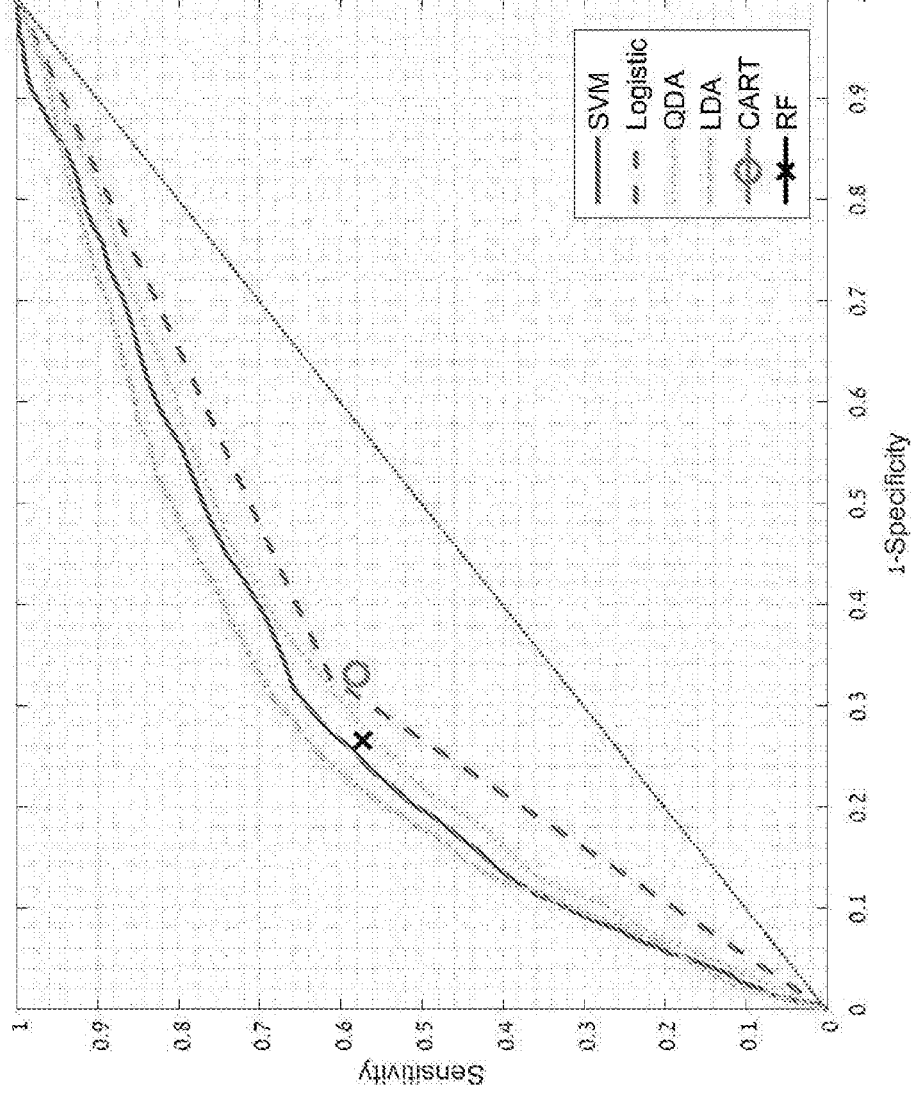

FIG. 7 shows ROC curves of six classification methods (SVM, LR, QDA, CART, RF and LDA), based on 100 iterations of 70:30 cross validation. Features were ranked according to their median scoring or frequency of model inclusion, depending on the method. Serum samples obtained from TBI patients at time 0 (t0) with abnormal CT were compared with samples obtained from TBI patients at time 0 (t0) with Normal CT. Analysis was based on 464 iChip features (232 antigen, IgM and IgG) and four ELISA features. iChip data is based on average of two block replicates, following correction procedure. ELISA features were selected based on data availability; only features with data available for >80% of the iChip samples were used. Samples with missing ELISA data were removed from the analysis.

DETAILED DESCRIPTION OF THE INVENTION

The present invention provides methods of diagnosing brain injury or a neurodegenerative disorder in a subject. The present invention further provides antigen probe sets or arrays for practicing such a diagnosis, and identifies specific antigen probe sets for generating such sets or arrays.

Without wishing to be bound by any particular theory or mechanism of action, the invention is based, in part, on the finding of unique antigens highly distinctive between healthy subjects and patients suffering from brain injury. The invention is further based on the finding that the antibody reactivity profile in serum of patients suffering from brain injury was clearly distinct from healthy control individuals. Although protein biomarkers of brain injury patients have been extensively investigated, the unique antibody immune signatures as described herein have not been described before. Advantageously, the unique antibody signatures of the present disclosure provide highly sensitive and specific assays for diagnosing brain injury.

The present invention provides, in some embodiments, unique antigen-antibody reactivity patterns particularly relevant to brain injury. In the course of investigating specific antibodies, the inventors examined the reactivity of IgM and IgG antibodies in the sera of healthy persons and those diagnosed with brain injury to a variety of antigens, using antigen microarray and informatics analysis.

Definitions

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "about" as used herein means in quantitative terms plus or minus 5%, or in another embodiment plus or minus 10%, or in another embodiment plus or minus 15%, or in another embodiment plus or minus 20%.

As used herein, the term "autoantibodies" refers to antibodies that are capable of reacting against an antigenic constituent of an individual's own tissue or cells (e.g., the antibodies recognize and bind to "self-antigens").

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as an impact (percussive or concussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

According to some embodiments of the method of the present invention, a healthy subject's predisposition to future onset of brain injury is also diagnosed. According to some embodiments said predisposition is due to previous injury or due to family history.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia. Many of these origins can lead to Chronic Traumatic Encephalopathy (CTE).

As employed herein, the term "traumatic brain injury" shall mean a brain injury resulting from direct or indirect shock load or loads applied to the brain causing it to move rapidly and unnaturally within a patient's skull and shall expressly include, but not be limited to, brain injuries caused by: (a) objects penetrating the skull, such as, bullets, arrows, and other physical objects which pass through the skull and enter the brain, (b) impact loads applied to the head or other portions of the patient's body, (c) surgically induced trauma, (d) explosions, such as might exist in warfare, through impacting of grenades, bombs, and other explosives, which cause substantial tremors in the earth in relatively-close proximity to where an individual is standing, as well as similar tremors created by nonexplosive means, such as sports injuries, vehicular accidents, collapse of buildings and earthquakes, for example. The results of traumatic brain injury may be of various types, but in each instance, will involve temporary or permanent reduction in the ability of the brain to function normally and may cause death.

One of the consequences of a traumatic brain injury frequently is the generation of inflammation within the brain as the shock to the brain serves to increase the permeability of the endothelial cells, thereby permitting loss of fluids from the vascular structure into the brain. Such a leakage frequently occurs due to the increased porosity of the blood vessels resulting from the trauma, thereby causing blood serum to leak through the vessels into the brain area. As this builds up, this can generate inflammation and swelling of the brain, which may require surgical intervention.

Clinically, traumatic brain injury can be rated as mild, moderate or severe based on TBI variables that include duration of loss of consciousness (LOC), Glasgow Coma Score (GCS) and post-traumatic stress amnesia.

As used herein, "secondary brain trauma" refers to damage to the brain of a patient post-acute brain injury, i.e., during the secondary injury phase of a TBI.

"Chronic traumatic encephalopathy (CTE)" is a neurodegenerative disease that is most often identified in postmortem autopsies of individuals exposed to repetitive head impacts, such as boxers and football players. The neuropathology of CTE is characterized by the accumulation of hyperphosphorylated tau protein in a pattern that is unique from that of other neurodegenerative diseases, including Alzheimer's disease. The clinical features of CTE are often progressive, leading to dramatic changes in mood, behavior, and cognition, frequently resulting in debilitating dementia. In some cases, motor features, including Parkinsonism, can also be present.

A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

"Stroke" refers to the destruction of brain tissue as a result of intracerebral hemorrhage or infarction. Stroke is a leading cause of death in the developed world. It may be caused by reduced blood flow and death of tissues in one area of the brain (infarction). Causes of strokes include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke.

"Alzheimer's disease (AD)" is a very common yet irreversible, progressive brain disease that slowly destroys memory and thinking skills, and eventually the ability to carry out the simplest tasks. AD is the most common cause of dementia among older people causing the loss of cognitive functioning thinking, remembering, and reasoning to such an extent that it interferes with a person's daily life and activities. Estimates vary, but experts suggest that as many as 5.1 million Americans may have AD. Currently brain imaging of people with, and those with a family history, of AD or its earlier stage, amnesic mild cognitive impairment (MCI), are beginning to detect changes in the brain. The clinical dementia of AD is coupled with a distinct pathology of senile plaques. AD is characterized by abnormal amyloid beta accumulation and deposition in brain parenchyma and cerebral capillaries, which leads to blood-brain barrier (BBB) disruption.

As used herein, "chronic brain injury" refers to a subject who has suffered a brain injury from three days post injury until at least 12 months previously yet continues to present symptoms of brain injury.

As used herein, "sub-acute brain injury" refers to a subject who has suffered a brain injury from about 2-5 days post injury.

"Conscious", as used herein, has the conventional meaning, as set forth in Plum, et al., The Diagnosis of Stupor and Coma, CNS Series, Philadelphia:Davis (1982), which is hereby incorporated by reference. Conscious patients include those who have a capacity for reliable, reproducible, interactive behavior evidencing awareness of self or the environment. Conscious patients include patients who recover consciousness with less severe brain injury but who, because of their impaired cognitive function, do not reach independent living. Conscious patients do not include those who exhibit wakefulness but lack interaction (e.g., those deemed to be in a persistent vegetative state).

The subject who is conscious after exposure to a head trauma may be asymptomatic of any visible symptoms of traumatic brain injury. Conversely, the subject may exhibit various symptoms of brain injury and cognitive dysfunction.

This is in contrast to a subject who is unconscious at the time of the obtaining, as indicated by conditions such as a concussion or intracranial hemorrhage (e.g. intra-axial hematoma, epidural hematoma, and subdural hematoma).

The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time) and the effectiveness or response to treatment of brain injury (e.g., clinical follow up and surveillance of brain injury after treatment). Based on this status, further procedures may be indicated, including additional diagnostic tests or therapeutic procedures or regimens.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in a method of the present invention, e.g., to diagnose brain injury in a patient. Brain injury biomarker proteins include, but are not limited to, SNCB, GFAP, S100B, MT3, ICAM5, BDNF, and/or NSE. The term also includes other brain injury biomarker proteins known in the art including neurogranin (NRGN), myelin basic protein (MBP), PAD-2, tubulin beta-4B chain, tubulin alpha-IB chain, CNPase, PPIA, Septin-7, Elongation factor 1-alpha2, TPPP, TPPP3, Ermin Isoform 2, NDRG2 Isoform 2, astrotactin 1 (ASTN1), brain angiogenesis inhibitor 3 (BAD); carnosine dipeptidase 1 (CNDP 1); ERMTN; glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); and peptidylarginine deiminase (types 1-4 and 6) (PAD).

In addition, the term "brain injury biomarkers" also includes the isoforms and/or post-translationally modified forms of any of the foregoing. The present invention contemplates the detection, measurement, quantification, determination and the like of both unmodified and modified (e.g., citrullination or other post-translational modification) proteins/polypeptides/peptides as well as autoantibodies to any of the foregoing. In certain embodiments, it is understood that reference to the detection, measurement, determination, and the like, of a biomarker refers detection of the protein/polypeptide/peptide (modified and/or unmodified). In other embodiments, reference to the detection, measurement, determination, and the like, of a biomarker refers detection of autoantibodies of the protein/polypeptide/peptide.

As used herein, the term "comparing" refers to making an assessment of how the reactivity of antibodies in a sample from a patient relates to the reactivity of the corresponding antibodies in a standard or control sample. For example, "comparing" may refer to assessing whether the reactivity of antibodies from a sample of a patient to one or more antigens is the same as, more or less than, or different from the corresponding reactivity of antibodies from the standard or control sample. More specifically, the term may refer to assessing whether the reactivity of antibodies of a sample from a patient to one or more antigens is the same as, more or less than, different from or otherwise corresponds (or not)

to a predefined reactivity of antibodies that correspond to, for example, a patient having subclinical brain injury (SCI), not having SCI, is responding to treatment for SCI, is not responding to treatment for SCI, is/is not likely to respond to a particular SCI treatment, or having/not having another disease or condition.

As used herein, the terms "indicates" or "correlates" (or "indicating" or "correlating," or "indication" or "correlation," depending on the context) in reference to a parameter, e.g., a modulated reactivity of antibodies of a sample from a patient, may mean that the patient has brain injury. In specific embodiments, the parameter may comprise the reactivity of antibodies to one or more antigens of the present invention. A particular reactivity of antibodies to one or more antigens may indicate that a patient has brain injury (i.e., correlates to a patient having brain injury). In other embodiments, a particular reactivity of antibodies to one or more antigens may be correlated to a patient being unaffected (i.e., indicates a patient does not have brain injury. In certain embodiments, "indicating." or "correlating." as used according to the present invention, may be by any linear or non-linear method of quantifying the relationship between levels of reactivity of antibodies to a standard, control or comparative value for the assessment of the diagnosis, prediction of brain injury or brain injury progression, assessment of efficacy of clinical treatment, identification of a patient that may respond to a particular treatment regime or pharmaceutical agent, monitoring of the progress of treatment, and in the context of a screening assay, for the identification of an anti-brain injury therapeutic.

According to some embodiments, monitoring the progression of brain injury is conducted at 7-20 day time point post injury, where the neural circulatory reconnections begin to occur. According to some embodiments, the risk of damage to the neural circulatory system is predicted.

The terms "patient," "individual," or "subject" are used interchangeably herein, and refer to a mammal, particularly, a human. The patient may have mild, intermediate or severe disease. The patient may be treatment naive, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The term "healthy control" as used herein refers to a healthy individual; a baseline from the same individual, a plurality of healthy individuals, a data set or value corresponding to or obtained from a healthy individual or a plurality of healthy individuals.

The term "Extended Glasgow Outcome Scale (GOSE)" as used herein categorizes functional disability after TBI on a scale of 1-8, where 1=Dead and 8=Upper Good Recovery. The functional disability is defined as a GOSE score of <8.

The terms "measuring", "detecting" and "determining" are used interchangeably throughout, and refer to methods which include obtaining a patient sample and detecting reactivity of antibodies in a sample. In some embodiments, the terms refer to obtaining a patient sample and detecting the reactivity of antibodies in the sample to one or more antigens. Measuring can be accomplished by methods known in the art and those further described herein.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of brain injury. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid). In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The samples may be tested immediately after collection, after storage at 4 degrees, −20 degrees, or −80 degrees Celsius. After storage for 24 hours, 1 week, 1 month, 1 year, 10 years or up to 30 years.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the reactivity of antibodies in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., an brain injury treatment) on a patient. In yet another embodiment, a transcription rate, mRNA level, translation rate, protein level, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, etc. A "suitable control" can be a profile or pattern of reactivity of antibodies to at least one antigen that correlates to brain injury, to which a patient sample can be compared. The patient sample can also be compared to a negative control, i.e., a profile that correlates to not having brain injury.

Antigen probes to be used in the assays of the invention may be purified or synthesized using methods well known in the art. For example, an antigenic protein or peptide may be produced using known recombinant or synthetic methods, including, but not limited to, solid phase (e.g. Boc or f-Moc chemistry) and solution phase synthesis methods (Stewart and Young, 1963; Meienhofer, 1973; Schroder and Lupke, 1965; Sambrook et al., 2001). One of skill in the art will possess the required expertise to obtain or synthesize the antigen probes of the invention. Some of the antigen probes are also commercially available, e.g. from Sigma (St. Louis, Mo., USA), Prospec (Ness-Ziona, Israel), Abnova (Taipei City, Taiwan), Matreya LLC (Pleasant Gap, Pa., USA), Avanti Polar Lipids (Alabaster, Ala., USA), Calbiochem (San Diego, Calif., USA), Chemicon (Temecula, Calif., USA), GeneTex (San Antonio, Tex., USA), Novus Biologicals (Littleton, Colo., USA) Assay Designs (Ann Arbor, Mich., USA), ProSci Inc. (Poway, Calif., USA), EMD Biosciences (San Diego, Calif., USA), Cayman Chemical (Ann Arbor, Mich., USA), HyTest (Turku, Finland), Meridian Life Science (Memphis, Tenn. USA) and Biodesign International (Saco, Me., USA), as detailed herein below.

It should be noted, that the invention utilizes antigen probes as well as homologs, fragments, partial sequences, mutant forms, modified forms and derivatives thereof, as long as these homologs, fragments, partial sequences, mutant forms, modified forms and derivatives are immunologically cross-reactive with these antigen probes. The term "immunologically cross-reactive" as used herein refers to two or more antigens that are specifically bound by the same antibody. The term "homolog" as used herein refers to a peptide which having at least 70%, at least 75%, at least 80%, at least 85% or at least 90% identity to the antigen's amino acid sequence. Cross-reactivity can be determined by any of a number of immunoassay techniques, such as a competition assay (measuring the ability of a test antigen to competitively inhibit the binding of an antibody to its known antigen).

The term "peptide" typically refers to a polypeptide of up to about 50 amino acid residues in length. According to particular embodiments, the antigenic peptides of the invention may be 10-50 amino acids in length and are typically about 10-30 or about 15-25 amino acids in length.

The term encompasses native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, backbone modifications; and residue modifications.

The peptide antigens of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. According to some embodiments, the peptide antigens of the invention are BSA-conjugated peptides.

Functional derivatives consist of chemical modifications to amino acid side chains and/or the carboxyl and/or amino moieties of said peptides. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring or modified amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

The amino acid residues described herein are in the "L" isomeric form, unless otherwise indicated. However, residues in the "D" isomeric form can be substituted for any L-amino acid residue, as long as the peptide substantially retains the desired antibody specificity.

Suitable analogs may be readily synthesized by now-standard peptide synthesis methods and apparatus or recombinant methods. All such analogs will essentially be based on the antigens of the invention as regards their amino acid sequence but will have one or more amino acid residues deleted, substituted or added. When amino acid residues are substituted, such conservative replacements which are envisaged are those which do not significantly alter the structure or antigenicity of the polypeptide. For example basic amino acids will be replaced with other basic amino acids, acidic ones with acidic ones and neutral ones with neutral ones. In addition to analogs comprising conservative substitutions as detailed above, analogs comprising non-conservative amino acid substitutions are further contemplated, as long as these analogs are immunologically cross reactive with a peptide antigen of the invention.

In other aspects, there are provided nucleic acids encoding these peptides, vectors comprising these nucleic acids and host cells containing them. These nucleic acids, vectors and host cells are readily produced by recombinant methods known in the art (see, e.g., Sambrook et al., 2001). For example, an isolated nucleic acid sequence encoding an antigen of the invention can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

"Functionally equivalent variants" of the polypeptide or peptide antigens of the invention as used herein are polypeptides or peptides with partial sequence homology, polypeptides or peptides having one or more specific conservative and/or non-conservative amino acid changes and polypeptide or peptide conjugates which do not alter the biological or structural properties of the polypeptide or peptide.

In terms of "functional analogues", it is well understood by those skilled in the art, that inherent in the definition of a biologically functional polypeptide or peptide analogue is the concept that there is a limit to the number of changes that may be made within a defined portion of the molecule and still result in a molecule with an acceptable level of equivalent biological activity. A plurality of distinct polypeptides or peptides with different substitutions may easily be made and used in accordance with the invention. It is also understood that certain residues are particularly important to the biological or structural properties of a polypeptide, and such residues may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the polypeptide. Examples of such conservative changes are well-known to the skilled artisan and are within the scope of the present invention. Conservative substitution also includes the use of a chemically derivatized residue in place of a non-derivatized residue provided that the resulting polypeptide is a biologically functional equivalent to the polypeptide antigens.

Therefore, the "citrullinated polypeptides" encompass a polypeptide having an amino acid sequence that differs from the sequences provided herein by one or more conservative amino acid substitutions. The citrullinated polypeptides also encompass a polypeptide having an amino acid sequence that differs from the sequences provided herein by a single mutation, where the single mutation represents a single amino acid deletion, insertion or substitution.

The citrullinated peptides may be made by methods known to those of skill in the art most notably and preferably by chemical synthesis using techniques well known in the chemistry of proteins such as solid phase synthesis (Merrifield et al, 65 J. AM. CHEM. ASSOC. 2149 (1964); Merrifield et al, 85 J. AMER. CHEM. SOC. 2149 (1963); and Merrifield et al, 35 INT. J. PEPTIDE PROTEIN RES. 161-214 (1990)) or synthesis in homogenous solution (METHODS OF ORGANIC CHEMISTRY, E. Wansch (Ed.) Vol. 15, pts. I and II, Thieme, Stuttgart (1987)) to generate synthetic peptides. Citrulline is a post-translationally modified arginine that is created through the process of deimination which is catalyzed by the enzyme peptidylarginine deiminase 4 (PAD-4) that removes a positive charge from arginine and makes the resulting citrulline polar in nature.

In one embodiment, citrullinated peptides can be made from known commercially available sources. In this aspect, the lyophilized protein is reconstituted in an appropriate buffer to which the enzyme peptidylarginine deiminase 4 is added. Alternatively, $Ca^{2+}$ is added to PAD-4 in solution. The solution is allowed to stand at an appropriate temperature for a time sufficient to cause modification of arginine residues to citrulline and thus create a citrullinated protein. The citrullinated protein is then isolated by the removal of the enzyme using a high molecular weight membrane to separate the enzyme or other methods of chromatography. One of skill in the art will understand that the temperature of incubation, buffer condition and time of incubation may vary depending on the protein that is being deiminated (Masson-Bessiere et al, 166 J. IMMUNOL. 4177-4184 (2001)).

The citrullinated proteins may be further isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography) or by precipitation (immunoprecipitation).

Polyacrylamide gel electrophoresis can also be used to isolate the citrullinated proteins based on the molecular weight of the protein, charge properties and hydrophobicity. The purified citrullinated proteins can be used in further biochemical analyses to establish secondary and tertiary structure which may aid in the design of pharmaceuticals to interact with the protein, alter the protein charge configuration or charge interaction with other proteins or alter its function.

The term "oligonucleotide antigen" as used herein refer to a stretch of contiguous nucleotides of a certain length. Unless otherwise indicated, the term "oligonucleotide antigen" as used herein relates to a nucleotide sequence of between 15 and 40 nucleotides in length, alternatively between 17 and 28 nucleotides in length, or between 18-25 nucleotides in length. In certain embodiments, an oligonucleotide antigen consists of at least 4, at least 5, at least 6, at least 7, at least 8, at least 9, at least 10, at least 16, or more contiguous nucleotides. Each possibility represents a separate embodiment of the invention. In certain embodiments, an antigen consists of not more than 50, not more than 45, not more than 40, not more than 35, not more than 30, not more than 25, not more than 20, not more than 16, or less contiguous nucleotides. Each possibility represents a separate embodiment of the invention. In certain embodiments, an antigen consists of 10-30, 15-25 or 17-20 contiguous nucleotides. In certain embodiments, an antigen consists of 17, 18, 19 or 20 contiguous nucleotides.

As used herein, the "reactivity of antibodies in a sample" or "reactivity of an antibody in a sample" to "an antigen" or to "a plurality of antigens" refers to the immune reactivity of at least one antibody in the sample to at least one specific antigen selected from the plurality of antigens. The immune reactivity of the antibody to the antigen, i.e. its ability to specifically bind the antigen, may be used to determine the amount of the antibody in the sample. The calculated levels of each one of the tested antibodies in the sample are collectively referred to as the reactivity pattern of the sample to these antigens. The reactivity pattern of the sample reflects the levels of each one of the tested antibodies in the sample, thereby providing a quantitative assay. In a preferred embodiment, the antibodies are quantitatively determined.

A "significant difference" between reactivity patterns refers, in different embodiments, to a statistically significant difference, or in other embodiments to a significant difference as recognized by a skilled artisan. In another embodiment, a significant difference between the reactivity pattern of the sample obtained from the subject compared to the control reactivity pattern is an indication that the subject is afflicted with brain injury. In specific embodiments, up-regulation or higher reactivity of the reactivity of an antibody in a sample to an antigen refers to an increase (i.e., elevation) of about at least two, about at least three, about at least four, or about at least five times higher (i.e., greater)

than the reactivity levels of the antibody to the antigen in the control. In another embodiment, down-regulation or lower reactivity of the reactivity of an antibody in a sample to an antigen refers to a decrease (i.e., reduction) of about at least two, about at least three, about at least four, or about at least five times lower than the reactivity levels of the antibody to the antigen in the control.

According to some embodiments, the at least one oligonucleotide antigen is an oligonucleotide sequence comprising at least 5, 6, 7, 8, 9, 10, 11, 12, 13, 14, 15, 16, 17, 18, 19 or 20 contiguous adenine nucleotides. According to another embodiment, the oligonucleotide sequence comprises at most 20 contiguous adenine nucleotides. According to additional embodiments, the at least one oligonucleotide antigen is an oligonucleotide sequence comprising at least 5, 6, 7, 8, 9, 10, 11, 12, 13, 14, 15, 16, 17, 18, 19 or 20 contiguous thymine nucleotides. According to another embodiment, the oligonucleotide sequence comprises at most 20 contiguous thymine nucleotides.

According to additional embodiments, the at least one oligonucleotide antigen is an oligonucleotide sequence comprising at least 5, 6, 7, 8, 9, 10, 11, 12, 13, 14, 15, 16, 17, 18, 19 or 20 contiguous cytosine nucleotides. According to another embodiment, the oligonucleotide sequence comprises at most 20 contiguous cytosine nucleotides. According to additional embodiments, the at least one oligonucleotide antigen is an oligonucleotide sequence comprising 5-17, 6-17, 7-17, 8-17, 9-17, 10-17, 11-17, 12-17, 13-17, 14-17, 15-17, 16-17, or at most 17 contiguous guanine nucleotides.

According to some embodiments, the at least one antigen is selected from the group consisting of SEQ ID NOs: 1-115, isoforms thereof, post-translationally modified forms thereof, fragments thereof; or combinations of any of the foregoing.

According to some embodiments, the antigens are selected from proteins, peptides, oligonucleotide antigens, or any combinations thereof.

It should be understood each antigen according to the present invention may be bound by IgM antibodies and/or IgG antibodies found or isolated from a sample obtained or derived from the tested subject. Since the relative amounts of IgM antibodies and IgG antibodies against a certain epitope or antigen naturally change over the course of time, each antigen according to the present invention may be bound by IgM antibodies, IgG antibodies or both. In certain embodiments, the reactivity of antibodies means the reactivity of IgG antibodies. In certain embodiments, the reactivity of antibodies means the reactivity of IgM antibodies. According to another embodiment, the significantly higher reactivity of the antibodies in the sample means increased IgG reactivity. According to another embodiment, the significantly higher reactivity of the antibodies in the sample comprises increased IgM reactivity.

According to another embodiment, the increased IgM reactivity is of at least one antigen selected from the group consisting of SEQ ID NOs: 1-115, isoforms thereof, post-translationally modified forms thereof, or combinations of any of the foregoing.

According to another embodiment, the increased IgG reactivity is of at least one antigen selected from the group consisting of SEQ ID NOs: 1-115, isoforms thereof, post-translationally modified forms thereof, or combinations of any of the foregoing.

In certain embodiments, the increased IgM and IgG reactivity is of at least one antigen selected from the group consisting of SEQ ID NOs: 1-115, isoforms thereof, post-translationally modified forms thereof, or combinations of any of the foregoing. In certain embodiments, the increased IgM reactivity is of at least one antigen selected from the group consisting of SEQ ID NOs: 1-115, isoforms thereof, post-translationally modified forms thereof, fragments thereof, or combinations of any of the foregoing. Each possibility represents a separate embodiment of the invention.

It should be understood that in order to perform the methods of the present invention, samples obtained or derived from subjects must comprise antibodies produced by the subject himself. Therefore, samples may be obtained or derived from any tissue, organ or liquid naturally comprising at least a subset of the subject's antibodies. In certain embodiments, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample. Methods for obtaining and isolating appropriate samples are well within the purview of the skilled artisan.

According to certain embodiments of the methods of the present invention, the control is selected from the group consisting of a sample from at least one healthy individual, base line of the same subject, a panel of control samples from a set of healthy individuals, and a stored set of data from healthy individuals. Each possibility represents a separate embodiment of the invention. Typically, a healthy individual is a subject not afflicted with brain injury.

In particular embodiments, the significant difference is determined using a cutoff of a positive predictive value (PPV) of at least 85%, preferably at least 90%. Determining a PPV for a selected marker (e.g., an antigen) is well known to the ordinarily skilled artisan and is exemplified in the methods described below. Typically, positivity for an antigen is determined if it detected above 10% of the subjects in a specific study subgroup using a selected cutoff value, such as $PPV \geq 90\%$. For example, antigen i is determined to specifically characterize group A if it detected at least 10% of the subjects in group A with a $PPV \geq 90\%$ when compared to a different test group B. Subjects in group A that are above the cutoff of $PPV \geq 90\%$ for antigen i are considered to be positive for antigen i.

An antibody "directed to" an antigen, as used herein is an antibody which is capable of specific binding to the antigen. Determining the levels of antibodies directed to a plurality of antigens includes measuring the level of each antibody in the sample, wherein each antibody is directed to a specific antigen of the invention. This step is typically performed using an immunoassay, as detailed herein.

In other embodiments, determining the reactivity of antibodies in the sample to the at least one antigen (and the levels of each one of the tested antibodies in the sample) is performed by a process comprising contacting the sample, under conditions such that a specific antigen-antibody complex may be formed, with at least one antigen (or when a plurality of antigens is used, to an antigen probe set comprising the plurality of antigens), and quantifying the amount of antigen-antibody complex formed for each antigen probe. The amount of antigen-antibody complex is indicative of the level of the tested antibody in the sample (or the reactivity of the sample with the antigen).

In another embodiment the method comprises determining the reactivity of at least one IgG antibody and at least one IgM antibody in the sample to the plurality of antigens. In another embodiment, the method comprises determining the reactivity of a plurality of IgG antibodies and at least one IgM antibody in the sample to the plurality of antigens. In another embodiment, the method comprises determining the reactivity of at least one IgG antibody and a plurality of IgM antibodies in the sample to the plurality of antigens. According to another embodiment, the method comprises determining the reactivity of antibodies in the sample to a plurality of antigens.

Typically, determining the reactivity of antibodies in the sample to at least one antigen is performed using an immunoassay. Advantageously, when a plurality of antigens is used, the plurality of antigens may be used in the form of an antigen array.

Antigen Probes and Antigen Probe Sets

According to further embodiments, the invention provides antigen probes and antigen probe sets useful for diagnosing brain injury, as detailed herein.

The invention further provides a plurality of antigens also referred to herein as antigen probe sets. These antigen probe sets comprise a plurality of antigens which are reactive specifically with the sera of subjects having brain injury. According to the principles of the invention, the plurality of antigens may advantageously be used in the form of an antigen array. According to some embodiments the antigen array is conveniently arranged in the form of an antigen chip.

A "probe" as used herein means any compound capable of specific binding to a component. According to one aspect, the present invention provides an antigen probe set comprising a plurality of antigens selected from the group consisting of: SEQ ID NOs: 1-115, isoforms thereof, post-translationally modified forms thereof, fragments thereof, or combinations of any of the foregoing. According to certain embodiments, the antigen probe set comprises a subset of the antigens of the present invention. In a particular embodiment, the subset of antigens consists of: SEQ ID NOs: 1-24, 27-30, 42, 75, 76, isoforms thereof, post-translationally modified forms thereof, fragments thereof, or combinations of any of the foregoing.

In some embodiments, antigen probe set consists of up to 300 antigens. In some embodiments, the antigen probe set consists of 2-5 antigens.

According to another embodiment, the methods of the present invention comprise determining the reactivity of antibodies in the sample to at least one antigen selected from the group consisting of SEQ ID NO: 1-115, isoforms thereof, post-translationally modified forms thereof, fragments thereof, or combinations of any of the foregoing.

The reactivity of antibodies to the plurality of antigens of the invention may be determined according to techniques known in the art.

Preferably, the plurality of antigens of the methods and kits of the invention comprises a set of the antigens as disclosed herein. Yet in other embodiments, the plurality of antigens (or the antigen probe set) comprises or consists of a subset thereof, e.g. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 or 115 different antigens, each selected from the antigens of the present invention, wherein each possibility represents a separate embodiment of the invention. Such subsets may be selected so as to result in optimal sensitivity and/or specificity of the diagnostic assay.

Antigen probes to be used in the assays of the invention may be synthesized or purified using methods well known in the art.

It should be noted, that the invention utilizes antigen probes as well as homologs, fragments and derivatives thereof, as long as these homologs, fragments and derivatives are immunologically cross-reactive with these antigen probes. The term "f" as used herein refers to two or more antigens that are specifically bound by the same antibody. The term "homolog" as used herein refers to an antigen probes having at least 80%, at least 85% or at least 90% identity to the antigen's sequence or structure. Cross-reactivity can be determined by any of a number of immunoassay techniques, such as a competition assay (measuring the ability of a test antigen to competitively inhibit the binding of an antibody to its known antigen).

The term "fragment" as used herein refers to a portion of an antigen, or antigen analog which remains immunologically cross-reactive with the antigen probes, e.g., to immunospecifically recognize the target antigen. The fragment may have the length of about 80%, about 85%, about 90% or about 95% of the respective antigen.

According to another aspect, the present invention provides an antigen probe set comprising a plurality of antigen probes selected from the group consisting of SEQ ID NOs: 1-115, isoforms thereof, post-translationally modified forms thereof, fragments thereof, or combinations of any of the foregoing.

According to another related aspect, the present invention provides an antigen probe set comprising at least one antigen probe selected from the group consisting of SEQ ID NOs: 1-115, isoforms thereof, post-translationally modified forms thereof, fragments thereof, or combinations of any of the foregoing.

According to another aspect, the present invention provides an article of manufacture comprising the at least one of the antigen probe sets described above.

In certain embodiments, the article of manufacture is in the form of an antigen probe array or in the form of an antigen chip or in the form of a dipstick or in the form of a lateral flow test or any other platform known to those skilled in the art. An "antigen probe array." generally refers to a plurality of antigen probes, either mixed in a single container or arranges in to or more containers. An "antigen chip" generally refers to a substantially two dimensional surface, onto which a plurality of antigens are attached or adhered. A "dipstick" generally refers to an object, onto which one or a plurality of antigens are attached or adhered, which is dipped into a liquid to perform a chemical test or to provide a measure of quantity found in the liquid. A "lateral flow test" generally refers to devices intended to detect the presence (or absence) of a target analyte in sample (matrix) without the need for specialized and costly equipment. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use. For example, the aforementioned means may include reagents, detectable labels and/or containers which may be used for measuring specific binding of antibodies to the antigen probes of the invention. "Means" as used herein may also refer to devices, reagents and chemicals, such as vials, buffers and written protocols or instructions, used to perform biological or chemical assays.

According to another aspect, there is provided use of the at least one antigen selected from the group consisting of: SEQ ID NOs: 1-115, isoforms thereof, post-translationally modified forms thereof, fragments thereof, or combinations of any of the foregoing; for the preparation of a diagnostic kit for diagnosing brain injury in a subject. The diagnostic kit is, in some embodiments, useful for determining the reactivity of antibodies in a sample, thereby determining the reactivity pattern of the sample to the at least one antigen. In some embodiments, a significant difference (e.g., increase) between the reactivity pattern of the sample compared to a reactivity pattern of a control sample is an indication for brain injury.

In other embodiments, the plurality of antigens comprised in the antigen probe set comprises or consists up to 50, 55, 60, 70, 80, 90 or 100 different antigens. In other embodiments, the plurality of antigens comprised in the antigen probe set comprises or consists at least 50, 100, 150, 200 or 500 different antigens.

In other aspects, there are provided nucleic-acid vectors comprising the oligonucleotides of the invention and host cells containing them. These nucleic acids, vectors and host cells are readily produced by recombinant methods known in the art. A poly-nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to perform the methods of the present invention.

According to the invention, the kits comprise a plurality of antigens also referred to herein as antigen probe sets. These antigen probe sets comprising a plurality of antigens are reactive specifically with the sera of subjects having brain injury. In some embodiments, the antigen probe sets can differentiate between sera of subjects having brain injury and normal subject. According to the principles of the invention, the plurality of antigens may advantageously be used in the form of an antigen array. According to some embodiments the antigen array is conveniently arranged in the form of an antigen chip.

In other embodiments, the kit may further comprise means for determining the reactivity of antibodies in a sample to the plurality of antigens. For example, the kit may contain reagents, detectable labels and/or containers which may be used for measuring specific binding of antibodies to the antigen probes of the invention. In a particular embodiment, the kit is in the form of an antigen array.

In some embodiments, the kit comprises means for comparing reactivity patterns of antibodies in different samples to the plurality of antigens. In other embodiments, the kit may further comprise negative and/or positive control samples. For example, a negative control sample may contain a sample from at least one healthy individual (e.g., an individual not-afflicted with brain injury). A positive control may contain a sample from at least one individual afflicted with brain injury, or a subtype of brain injury which is being diagnosed. Other non-limiting examples are a panel of control samples from a set of healthy individuals or diseased individuals, or a stored set of data from control individuals.

Antibodies, Samples and Immunoassays

Antibodies, or immunoglobulins, comprise two heavy chains linked together by disulfide bonds and two light chains, each light chain being linked to a respective heavy chain by disulfide bonds in a "Y" shaped configuration. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')₂ fragments. Further included within the scope of the invention (for example as immunoassay reagents, as detailed herein) are chimeric antibodies; recombinant and engineered antibodies, and fragments thereof.

Exemplary functional antibody fragments comprising whole or essentially whole variable regions of both light and heavy chains are defined as follows: (i) Fv, defined as a genetically engineered fragment consisting of the variable region of the light chain and the variable region of the heavy chain expressed as two chains; (ii) single-chain Fv ("scFv"), a genetically engineered single-chain molecule including the variable region of the light chain and the variable region of the heavy chain, linked by a suitable polypeptide linker; (iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof: (iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens. An "antigenic peptide" is a peptide which is capable of specifically binding an antibody.

In another embodiment, detection of the capacity of an antibody to specifically bind an antigen probe may be performed by quantifying specific antigen-antibody complex formation. The term "specifically bind" as used herein means that the binding of an antibody to a specific antigen probe is not affected by the presence of non-related molecules.

In certain embodiments, the method of the present invention is performed by determining the capacity of an antigen of the invention to specifically bind antibodies of the IgG isotype, or, in other embodiments, antibodies of the IgM, isolated from a subject.

Methods for obtaining suitable antibody-containing biological samples from a subject are well within the ability of those of skill in the art. Typically, suitable samples comprise whole blood and products derived therefrom, such as plasma and serum. In other embodiments, other antibody-containing samples may be used, e.g. CSF, urine and saliva samples.

Numerous well known fluid collection methods can be utilized to collect the biological sample from the subject in order to perform the methods of the invention.

In accordance with the present invention, any suitable immunoassay can be used with the subject antigens. Such techniques are well known to the ordinarily skilled artisan and have been described in many standard immunology manuals and texts. In certain preferable embodiments, determining the capacity of the antibodies to specifically bind the antigen probes is performed using an antigen probe array-based method. Preferably, the array is incubated with suitably diluted serum of the subject so as to allow specific binding between antibodies contained in the serum and the immobilized antigen probes, washing out unbound serum from the array, incubating the washed array with a detectable label-conjugated ligand of antibodies of the desired isotype, washing out unbound label from the array, and measuring levels of the label bound to each antigen probe.

In various embodiments, the method of the present invention further comprises diluting the sample before performing the determining step. In one embodiment, the sample is diluted 1:2, for instance, using PBS. In another embodiment, the sample is diluted 1:4, 1:6, 1:8, 1:15, 1:20, 1:50, or preferably 1:10. Each possibility represents a separate embodiment of the present invention. In another embodiment, the sample is diluted in the range of times 2-times 10. In another embodiment, the sample is diluted in the range of times 4-times 10. In another embodiment, the sample is diluted in the range of times 6-times 10. In another embodiment, the sample is diluted in the range of times 8-times 10. The Antigen Chip Antigen microarrays are used for the high-throughput characterization of the immune response (Robinson et al., 2002, *Nat Med* 8, 295-301), and have been used to analyze immune responses in vaccination and in autoimmune disorders (Robinson et al., 2002; Robinson et al., 2003, *Nat Biotechnol.* 21, 1033-9; Quintana et al., 2004; Kanter et al., 2006, *Nat Med* 12, 138-43). It has been hypothesized, that patterns of multiple reactivities may be more revealing than single antigen-antibody relationships (Quintana et al., 2006, *Lupus* 15, 428-30) as shown in previous analyses of autoimmune repertoires of mice (Quintana et al., 2004; Quintana et al., 2001, *J Autoimmun* 17, 191-7) and humans (Merbl et al., 2007, *J Clin Invest* 117, 712-8; Quintana et al., 2003, *J Autoimmun* 21, 65-75) in health and disease. Thus, autoantibody repertoires have the potential to provide both new insights into the pathogenesis of the disease and to serve as immune biomarkers (Cohen, 2007, *Nat Rev Immunol.* 7, 569-74) of the disease process.

According to some aspects the methods of the present invention may be practiced using antigen arrays as disclosed in WO 02/08755 and U.S. 2005/0260770, the contents of which are incorporated herein by reference. WO 02/08755 is directed to a system and an article of manufacture for clustering and thereby identifying predefined antigens reactive with undetermined immunoglobulins of sera derived from patient subjects in need of diagnosis of disease or monitoring of treatment. Further disclosed are diagnostic methods, and systems useful in these methods, employing the step of clustering a subset of antigens of a plurality of antigens, the subset of antigens being reactive with a plurality of antibodies being derived from a plurality of patients, and associating or disassociating the antibodies of a subject with the resulting cluster.

U.S. Pat. App. Pub. No. 2005/0260770 discloses an antigen array system and diagnostic uses thereof. The application provides a method of diagnosing an immune disease, particularly diabetes type 1, or a predisposition thereto in a subject, comprising determining a capacity of immunoglobulins of the subject to specifically bind each antigen probe of an antigen probe set. The teachings of the disclosures are incorporated in their entirety as if fully set forth herein.

In other embodiments, various other immunoassays may be used, including, without limitation, enzyme-linked immunosorbent assay (ELISA), flow cytometry with multiplex beads (such as the system made by Luminex), surface plasmon resonance (SPR), elipsometry, and various other immunoassays which employ, for example, laser scanning, light detecting, photon detecting via a photo-multiplier, photographing with a digital camera based system or video system, radiation counting, fluorescence detecting, electronic, magnetic detecting and any other system that allows quantitative measurement of antigen-antibody binding.

Various methods have been developed for preparing arrays suitable for the methods of the present invention. State-of-the-art methods involves using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. First, the glass surface is activated by a chemical treatment that leaves a layer of reactive groups such as epoxy groups on the surface, which bind covalently any molecule containing free amine or thiol groups. Suitable supports may also include silicon, nitrocellulose, paper, cellulosic supports and the like.

Preferably, each antigen probe, or distinct subset of antigen probes of the present invention, which is attached to a specific addressable location of the array is attached independently to at least two, more preferably to at least three separate specific addressable locations of the array in order to enable generation of statistically robust data.

According to additional embodiments, the antigen probe set comprises at least 5, at least 25, at least 100, at least 150, at least 200, at least 250, at least 300 or more antigens, including one or a plurality of the antigens provided by the present invention.

In addition to antigen probes of the invention, the array may advantageously include control antigen probes or other standard chemicals. Such control antigen probes may include normalization control probes. The signals obtained from the normalization control probes provide a control for variations in binding conditions, label intensity, "reading" efficiency and other factors that may cause the signal of a given binding antibody-probe ligand interaction to vary. For example, signals, such as fluorescence intensity, read from all other antigen probes of the antigen probe array are divided by the signal (e.g., fluorescence intensity) from the normalization control probes thereby normalizing the measurements. Normalization control probes can be bound to various addressable locations on the antigen probe array to control for spatial variation in antibody-ligand probe efficiency. Preferably, normalization control probes are located at the corners or edges of the array to control for edge effects, as well as in the middle of the array.

The labeled antibody ligands may be of any of various suitable types of antibody ligand. Preferably, the antibody ligand is an antibody which is capable of specifically binding the Fc portion of the antibodies of the subject used. For example, where the antibodies of the subject are of the IgM isotype, the antibody ligand is preferably an antibody capable of specifically binding to the Fc region of IgM antibodies of the subject.

The ligand of the antibodies of the subject may be conjugated to any of various types of detectable labels. Preferably the label is a fluorophore, most preferably Cy3. Alternately, the fluorophore may be any of various fluorophores, including Cy5, Dy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of blood serum or plasma or a dilution thereof (e.g. 1:10 dilution), the antibodies may be subjected to any desired degree of purification prior to being tested for their capacity to specifically bind antigen probes. The method of the present invention may be practiced using whole antibodies of the subject, or antibody fragments of the subject which comprises an antibody variable region.

Combination Measurement of the Levels of One or More Antibodies and One or More Biomarkers in the Sample Obtained From the Subject The present invention is based, at least in part, on the discovery that a combination measurement of the levels of one or more antibodies and one or more biomarkers in the sample obtained from the subject can measure both the real-time background physiology of the subject and the status of the acute event.

In a patient with Brain Injury, the response to injury and the recovery process from the injury is dependent upon a combination of the nature of the injury and the state of the individual prior to injury. Patients that are injured on top of a 'healthy' background will likely have a better (faster, more complete) recovery profile than patients that are injured on a 'sick' or 'previously injured' background.

Determination of the autoantibody profile of a patient can be used as a surrogate measurement of the state of the patient prior to brain injury and determination of the levels of circulating antigen shortly after injury can be used as a surrogate measurement of the nature/degree of injury. Algorithms that combine the information about the state of the patient prior to injury and the nature/degree of the injury can be used in order to predict outcomes.

Determination of the autoantibody profile can be performed using any platform where antigens are bound to a surface, circulating antibodies bind to the antigen and are detected with a tagged secondary antibody. Determination of the circulating antigen profile can be done in any ELISA type sandwich assay format which includes a capture antibody and a detection antibody.

The platforms used for antibody and antigen detection may be independent (eg. iCHIP for autoantibody, MSD ELISA for antigens or any relevant ELISA based platform) or may be combined into a single platform to simultaneously measure both circulating autoantibody and antigen. This can be done by printing an iCHIP with both relevant antigens and capture antibodies, contacting serum with the printed surface such that circulating antibodies will bind to the surface bound antigen, and circulating antigens will bind to the surface bound capture antibodies. Detection can be with a cocktail of secondary and detection antibodies.

In the case where there is a need to measure autoantibodies to the same antigen that is informative about the disease state, these measurements can we done in two separate chambers. The data from multiple tests can be combined for the purpose of an algorithmic analysis to finally predict the status of the patient.

Kits for the Detection of Biomarkers

In another aspect, the present invention provides kits for qualifying brain injury status, which kits are used to detect the biomarkers described herein. In a specific embodiment, the kit is provided as an ELISA kit comprising antibodies to the biomarkers of the present invention including, but not limited to, glial fibrillary acidic protein (GFAP) and Synuclein beta (Sncb).

In an alternative embodiment, the panel of biomarkers comprises BDNF, GFAP, MT3 and SNCB. In another embodiment, the panel of biomarkers comprises BDNF, GFAP, NRGN and SNCB. In a further embodiment, the panel of biomarkers comprises BDNF, ICAM5, MT3 and SNCB.

The ELISA kit may comprise a solid support, such as a chip, microtiter plate (e.g., a 96-well plate), bead, or resin having biomarker capture reagents attached thereon.

The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

Data Analysis

Advantageously, the methods of the invention may employ the use of learning and pattern recognition analyzers, clustering algorithms and the like, in order to discriminate between reactivity patterns of healthy control subjects to those of patients having brain injury. As such, this term specifically includes a difference measured by, for example, determining the reactivity of antibodies in a test sample to a plurality of antigens, and comparing the resulting reactivity pattern to the reactivity patterns of negative and positive control samples (e.g. samples obtained from control subjects which are not afflicted with brain injury or patients afflicted with brain injury, respectively) using such algorithms and/or analyzers. The difference may also be measured by comparing the reactivity pattern of the test sample to a predetermined classification rule obtained in such manner.

In some embodiments, the methods of the invention may employ the use of learning and pattern recognition analyzers, clustering algorithms and the like, in order to discriminate between reactivity patterns of subjects having a subtype of brain injury to control subjects. For example, the methods may include determining the reactivity of antibodies in a test sample to a plurality of antigens, and comparing the resulting pattern to the reactivity patterns of negative and positive control samples using such algorithms and/or analyzers.

Thus, in another embodiment, a significant difference between the reactivity patterns of a test sample compared to a reactivity pattern of a control sample, wherein the difference is computed using a learning and pattern recognition algorithm, indicates that the subject is afflicted with brain injury. For example, the algorithm may include, without limitation, supervised or non-supervised classifiers including statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor, artificial neural networks, coupled two-way clustering algorithms, multi-layer perceptrons (MLP), generalized regression neural network (GRNN), fuzzy inference systems (FIS), self-organizing map (SOM), genetic algorithms (GAS), neuro-fuzzy systems (NFS), adaptive resonance theory (ART).

In certain embodiments, one or more algorithms or computer programs may be used for comparing the amount of each antibody quantified in the test sample against a predetermined cutoff (or against a number of predetermined cutoffs). Alternatively, one or more instructions for manually performing the necessary steps by a human can be provided.

Algorithms for determining and comparing pattern analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

Diagnostic Methods

As used herein the term "diagnosing" or "diagnosis" refers to the process of identifying a medical condition or disease (e.g., brain injury) by its signs, symptoms, and in particular from the results of various diagnostic procedures, including e.g. detecting the reactivity, or reactivity pattern, of antibodies in a biological sample (e.g. serum) obtained from an individual, to one or more antigens. Furthermore, as used herein the term "diagnosing" or "diagnosis" encompasses screening for a disease, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy (dose/schedule) for a disease, monitoring the treatment of a disease, and/or predicting the suitability of a therapy for specific patients or subpopulations or determining the appropriate dosing of a therapeutic product in patients or subpopulations.

In one embodiment, diagnosing brain injury further permits assessing a risk of said brain injury evolving to brain damage and leading to long-term dysfunction. In another embodiment, assessment of a risk of said brain injury evolving to long-term dysfunction permits therapeutic intervention at an early stage.

The immediate issue facing an individual that has suffered a TBI is determining when it is safe to return to high risk activities after a concussive injury without risking permanent brain damage that occurs at a cellular level. According to some embodiments, the present invention provides a broad immune system test to monitor, assess chronic outcomes and verify safety to return to work or play.

Assessment of pathology and neurological impairment immediately after TBI is crucial for determination of appropriate clinical management and for predicting long-term outcome. The outcome measures most often used in head injuries are the Glasgow Coma Scale (GCS), the Glasgow Outcome Scale (GOS), computed tomography, and magnetic resonance imaging (MRI) to detect intracranial pathology. However, despite dramatically improved emergency triage systems based on these outcome measures, most TBI suffer long term impairment and a large number of TBI survivors are severely affected despite predictions of "good recovery" on the GOS. In addition, CT and MRI are expensive and cannot be rapidly employed in an emergency room environment. Moreover, in austere medical environments associated with combat, accurate diagnosis of TBI would be an essential prerequisite for appropriate triage of casualties.

In one embodiment, the type of brain damage associated with brain injury is a white matter structural abnormality. In another embodiment, the white matter structural abnormality or damage is in the corpus callosum region. In another embodiment, the abnormality or damage is in the uncinate fasciculus. In another embodiment, the abnormality or damage is in the right brain frontal lobe. In another embodiment, the abnormality or damage is in the left frontal lobe. In another embodiment, the abnormality or damage is diffuse axonal injury (DAI). In another embodiment, the abnormality or damage is diffuse vascular injury.

In some embodiments, the brain injury is a mild TBI, in one embodiment a concussion is a mild TBI. In another embodiment, mild TBI is caused by a head injury, where the head injury is, in another embodiment, blunt trauma, acceleration, or deceleration forces. It will be appreciated that such head injuries can be characterized by having one or more of the following conditions: (1) observed or self-reported contusion, disorientation, or impaired consciousness, dysfunction of memory at the time of the injury, loss of consciousness lasting less than 30 minutes; and, (2) symptoms such as headache, dizziness, fatigue, irritability, and poor concentration soon after the injury. Head injuries are also categorized as mild based on clinical examinations using the Glasgow Coma Scale. In one embodiment, the head injury has a Glasgow Coma Scale score (GCS) of 13-15 upon examination at an emergency center, with no abnormal findings on head CT, duration of loss of consciousness for no more than 30 minutes, post-traumatic amnesia for less than 24 hours, and an Abbreviated Injury Score (AIS) S3 and an ISS of <12 modified to exclude the head region.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis. The "accuracy" of a diagnostic assay is the proximity of measurement results to the true value. The "p value" of a diagnostic assay is the probability of obtaining the observed sample results (or a more extreme result) when the null hypothesis is actually true.

In certain embodiments, the use of an antigen probe set provided by the present invention, or an antigen probe array provided by the present invention, results in an antibody reactivity profile which is brain injury-indicative (p value$\leq$1.00E-08), sensitive ($\geq$0.600), specific ($\geq$0.700) and accurate ($\geq$0.600). In certain embodiments, the use results in an antibody reactivity profile which is more brain injury-indicative (p value$\leq$1.00E-10), sensitive ($\geq$0.700), specific ($\geq$0.800) and accurate ($\geq$0.700). In certain embodiments, the use results in an antibody reactivity profile which is even more brain injury-indicative (p value$\leq$1.00E-12), sensitive ($\geq$0.800), specific ($\geq$0.900) and accurate ($\geq$0.800). In certain embodiments, the use results in an antibody reactivity profile which is yet even more brain injury-indicative (p value $\leq$1.00E-14), sensitive ($\geq$0.900), specific ($\geq$0.950) and accurate ($\geq$0.900). In certain embodiments, the use results in an antibody reactivity profile which highly brain injury-indicative (p value$\leq$1.00E-16), sensitive ($\geq$0.950), specific ($\geq$0.990) and accurate ($\geq$0.950). Each possibility represents a separate embodiment of the invention.

In certain embodiments, the antigens provided by the present invention, or the antigen patterns provided by the present invention, are brain injury-indicative (p value$\leq$1.87E-08), sensitive ($\geq$0.609), specific ($\geq$0.769) and accurate ($\geq$0.687). In certain embodiments, the antigens provided by the present invention, or the antigen patterns provided by the present invention, are advantageously brain injury-indicative (p value$\leq$2.81E-12), sensitive ($\geq$0.657), specific ($\geq$0.798) and accurate ($\geq$0.725). In certain embodiments, the antigens provided by the present invention, or the antigen patterns provided by the present invention, are further advantageously brain injury-indicative (p value$\leq$8.00E-14), sensitive ($\geq$0.663), specific ($\geq$0.814) and accurate ($\geq$0.738).

In another embodiment, the methods may result in determining a level of brain injury progression. In a further embodiment, the methods may result in providing the comparison to an entity for monitoring brain injury progression. In these embodiments, the methods can be used, for example, to differentiate between subjects with progressing brain injury, and subjects with regressing brain injury.

In one embodiment, the subject being diagnosed according to the methods of the invention is symptomatic. In other embodiments, the subject is asymptomatic. In certain embodiments the subject shows immediate symptoms. In certain embodiments the subject shows delayed symptoms. In certain embodiments, the subject is not or was not receiving a treatment.

As used herein, the term "treating" may encompass curing, preventing, reducing the incidence of, ameliorating symptoms of, to inducing remission of, or slowing the progression of a disease. The terms "reducing", "suppressing" and "inhibiting" refer to lessening or decreasing.

The diagnostic procedure can be performed in vivo or in vitro, preferably in vitro. In certain embodiments of the methods of the present invention, the diagnostic procedure is performed by non-invasive means or methods.

The diagnostic procedure and platform of the present invention may be suitable for use as point of care device or point of service in clinic, in physician's office, in hospital laboratories, or in commercial diagnostic laboratories.

The following examples are presented in order to more fully illustrate some embodiments of the invention. They should, in no way be construed, however, as limiting the broad scope of the invention.

EXAMPLES

Materials and Methods

Human Subjects

The study was approved by the Institutional Review Boards of the participating clinical unit; informed consent was obtained from all participants. In an initial study, sera derived from blood samples obtained from healthy subjects, and subjects suffering from brain injury at varying times post injury, and with varying GOSE scores, were tested using an antigen microarray that included 228 antigens (see Table 1).

Blood samples and clinical data were collected from patients in the HeadSMART trial, arriving at the emergency departments (ED) of Johns Hopkins Hospital (JHH, Baltimore; n=61) or at one of the participating centers of the COBRIT clinical trial (n=31; as described in JAMA. 2012; 308(19):1993-2000).

Defined human serum samples were used for this study. Samples from adult TBI patients were analyzed retrospectively. The healthy control cohort of patients, evaluated for non-TBI complaints was obtained from Baylor College of Medicine (Houston, TX; n=21).

To be considered a TBI patient for the HeadSMART trial, the following criteria had to be met: 18 years old or greater, blunt TBI presenting within 24 hours of injury, met the American College of Emergency Physicians (ACEP) criteria for obtaining head CT scans in TBI. Patients having brain tumor, brain surgery, pregnant, non-English speakers, were excluded. Serial serum samples were collected from enrollment to up to 6 months from 61 TBI patients. Three samples per patient at eight different time points after brain injury were collected, a selection of which were used in the analysis For COBRIT trial samples, the following criteria were used: Inclusion Criteria were that the patient had a non-penetrating traumatic brain injury, age 18 (19 in Alabama)-70 years, GCS criteria on/off paralytics as specified in protocol, reasonable expectation of completion of outcome measures at a network center at six months post-injury, reasonable expectation of enrollment within 24-hour time window, and English-speaking. Exclusion criteria included: Intubated patients with GCS motor score=6 and not meeting CT criteria, bilaterally fixed and dilated pupils, positive pregnancy test, known pregnancy, or currently breast feeding, evidence of diseases that interfere with outcome assessment, current acetylcholinesterase inhibitor use, imminent death or current life-threatening disease, currently enrolment in another study, or prisoners. For healthy controls, 21 non-TBI individuals at least 18 years of age were recruited under informed consent at Baylor College of Medicine. One blood sample was collected per control individual and processed to obtain replicate vials of serum and plasma, which were stored at −80° Celsius until use. All patient identifiers were kept confidential.

Antigens and Serum Testing 228 different antigens were spotted on in-house produced epoxyhexyltriethoxysilane (EHTES) activated epoxy slides using a Scienion S-11 non-contact microarray printer (Scienion AG, Germany). The microarrays were then blocked for 1 hour at room temperature with 1% casein. Test serum samples in 1% casein blocking buffer (1:20 dilution) were incubated under a coverslip for 1 hour at 37°. The arrays were then washed and incubated for 1 hour at 37° with a 1:500 dilution of two detection antibodies, mixed together: a goat anti-human IgG Cy3-conjugated antibody, and a goat anti-human IgM AF647-conjugated antibody (both purchased from Jackson ImmunoResearch Laboratories Inc., West Grove, PA). Image acquisition was performed by laser at two wavelengths 530 nm and 630 nm (Agilent Technologies, Santa Clara, CA) and the results were analyzed using Genepix pro 7 software (Molecular devices, Sunnyvale, CA). The quantitative range of signal intensity of binding to each antigen spot was 0-65,000; this range of detection made it possible to obtain reliable data at a 1:20 dilution of test serum samples.

Image Analysis and Data Processing

Each spot's intensity is represented by its pixels' mean after subtraction of its local background median, followed by Log 2 transform. Negative spots (following background subtraction) are imputed with background-like intensity. Background intensity was subtracted for each spot, to obtain net signals. For every antigen in every slide, outlier spots were removed. Outliers spots are defined as having Z score>2 or <−2. The intensity of multiple spots was combined through median, following removal of outlier spots. The foreground and background intensities of multiple spots of each antigen were averaged, and the difference between the foreground and the background was calculated. The resulting value was taken as the antigen reactivity of the antibodies binding to that spotted antigen. All antigens showed meaningful reactivity in a significant number of slides; thus no antigen was excluded.

Statistical Analysis of Antibody Results

Antigens whose reactivity was higher or lower in a specific study subgroup compared to other subgroups were identified. Univariare analysis was used for separating antigens in a T test. Antigens that allowed for setting a classification threshold such as positive predictive value (PPV) ≥90% and sensitivity≥20% were achieved and determined to significantly characterize a specific subgroup. For added restriction, only antigens whose p value for a two sided t-test (after Benjamini-Hochberg correction for multiple hypothesis) was smaller than 0.05 were selected.

ELISA Plate Assay Methods

Biomarkers are tested by either the colorimetric, fluorescence, chemiluminescent, or electrochemiluminescent detection methodologies. For the colorimetric detection methods, Maxisorb 96 well plates are used. For fluorescence assays, black opaque-walled plates are used. For luminescence based-assays, microtiter plates suitable for luminescence are used. Plates are prepared as follows. Plates are rinsed once with coating buffer specific to each plate type. Capture antibodies are added to each well at an optimized concentration for an optimal time period. Generally coating is performed over 12 hours at 4° C. in optimal coating buffer. Following the coating period, the excess antibody is removed and the plates are blocked in an optimized blocking buffer consisting of buffered saline with one of the following: Casein, bovine serum Albumin, species-specific whole serum, or filtered non-fat dry milk powder, or other blocking agent, and/or non-ionic detergent. A series of sequential incubations of optimal length are used to allow: 1) masking of non-specific binding sites (i.e., blocking), 2), capture antibody-antigen binding. 3) binding of antigen followed by washing for removal of excess and non-bound antigens, 4) incubation of anti-antigen detection antibody solution and detection tag, 5) washing for removal of excess non-bound detection antibody and tag, and 6) addition of detection substrate (ELISA) or optimal detection solution (fluorescence or luminescence). Colorimetric detection is performed on a microtiter plate reader, or similar technology, by measuring absorbance of a colored substrate at an appropriate wavelength of light. Fluorescence assays are performed using a fluorescence based plate reader. Luminescence is detected on a luminescence based reader. Data are collected and biomarker concentrations are determined using a standard curve of recombinant protein of known concentration.

Example 1: Association Between FABP (SEQ ID No: 61) and MBPR149 (SEQ ID No: 10) With TBI Outcomes Each patient was profiled with its own measured time-points in order to explore its autoantibodies profile change with time post injury. Samples from TBI patients with Extended Glasgow Outcome Scale (GOSE) equals 8 were compared to samples from TBI patients with GOSE lower than 8 at a specific time-point (3 months/1 month).

Antibodies' Binding

Sera samples from healthy subjects and brain injury patients at varying times post injury, and with varying GOSE scores were tested for binding of serum IgG and/or IgM antibodies to the various antigens disclosed in Table 1.

TABLE 1

List of brain injury related antigens.

| Antigen | Amino acid sequence or manufacture (Catalog number) | SEQ ID NO: |
|---|---|---|
| MBP (myelin basic protein) | MASQKRPSQRHGSKYLATASTMDHARHGFLPRHRDTGILDSIGRFFGGDRGAPKRGSG KVPWLKPGRSPLPSHARSQPGLCNMYKDSHHPARTAHYGSLPQKSHGRTQDENPVVHF FKNIVTPRTPPPSQGKGRGLSLSRFSWGAEGQRPGFGYGGRASDYKSAHKGFKGVDAQ GTLSKIFKLGGRDSRSGSPMARR Enzo LS (ALX-200-606-M001) | 1 |
| MBP- in vitro citrullinated | Post translational citullination of arginine(s) in Enzo LS (ALX-200-606-M001) | 2 |
| MBP R26 | Ac-TMDHA(Cit)HGFLPC-amide | 3 |
| MBP R32, R34 | Ac-GFLP(Cit)H(Cit)DTGIC-amide | 4 |
| MBP R44 | Ac-CILDSIG(Cit)FFGG-amide | 5 |
| MBP R50 | Ac-FGGD(Cit)GAPKRGC-amide | 6 |
| MBP R92 | Ac-CDSHHPA(Cit)TAHYG-amide | 7 |
| MBP R106 | Ac-CQKSHG(Cit)TQDEN-amide | 8 |
| MBP R124 | Ac-CFKNIVTP(Cit)TP-amide | 9 |
| MBP R149 | Ac-GAEGQ(Cit)PGFGYC-amide | 10 |
| MBP R157 | Ac-CGYGG(Cit)ASDYKS-amide | 11 |
| MBP R186, R189 | Ac-CKLGG(Cit)DS(Cit)SG-amide | 12 |
| MBP R196, R197 | Ac-C(Ahx)SGSPMA(Cit)(Cit)-OH | 13 |
| GFAP (glial fibrillary acid protein) | MERRRITSAARRSYVSSGEMMVGGLAPGRRLGPGTRLSLARMPPPLPTRVDFSLAGAL NAGFKETRASERAEMMELNDRFASYIEKVRFLEQQNKALAAELNQLRAKEPTKLADVY QAELRELRLRLDQLTANSARLEVERDNLAQDLATVRQKLQDETNLRLEAENNLAAYRQ EADEATLARLDLERKIESLEEEIRFLRKIHEEEVRELQEQLARQQVHVELDVAKPDLT AALKEIRTQYEAMASSNMHEAEEWYRSKFADLTDAAARNAELLRQAKHEANDYRRQLQ SLTCDLESLRGTNESLERQMREQEERHVREAASYQEALARLEEEGQSLKDEMARHLQE YQDLLNVKLALDIEIATYRKLLEGEENRITIPVQTFSNLQIRETSLDTKSVSEGHLKR NIVVKTVEMRDGEVIKESKQEHKDVM Calbiochem (345996) | 14 |
| GFAP- in in vitro citrullinated | Post translational citullination of arginine(s) Calbiochem (345996) | 15 |
| GFAP R30 | Ac-LAPGR(Cit)LGPGTC-amide | 16 |
| GFAP R36 | Ac-CLGPGT(Cit)LSLAR-amide | 17 |
| GFAP R270 | Ac-AA(Cit)NAELLRQC-amide | 18 |
| GFAP R406 | Ac-CEGHLK(Cit)NIVVK-amide | 19 |
| GFAP R416 | Ac-CVKTVEM(Cit)DGEVI-amide | 20 |

TABLE 1-continued

<u>List of brain injury related antigens.</u>

| Antigen | Amino acid sequence or manufacture (Catalog number) | SEQ ID NO: |
|---|---|---|
| NRGN (neurogranin) | MDCCTENACSKPDDDILDIPLDDPGANAAAAKIQASFRGHMARKKIKSGERGRKGPGP GGPGGAGVARGGAGGGPSGD | 21 |
| NRGN- in vitro citrullinated | Post translational citullination of arginine(s) in NRGN | 22 |
| NRGN R51, R53 | Ac-CKSGE(Cit)G(Cit)KGPG-amide | 23 |
| NRGN R68 | Ac-CGGAGVA(Cit)GGAG-amide | 24 |
| ERMIN | MKTLSPDRIQPHIMTDVPATFTQAECNGDKPPENGQQTITKISEELTDVDSPLPHYRV EPSLEGALTKGSQEERRKLQGNMLLNSSMEDKMLKENPEEKLFIVHKAITDLSLQETS ADEMTFREGHQWEKIPLSGSNQEIRRQKERITEQPLKEEEDEDRKNKGHQAAEIEWLG FRKPSQADMLHSKHDEEQKVWDEEIDDDDDDNCNNDEDEVRVIEFKKKHEEVSQFKEE GDASEDSPLSSASSQAVTPDEQPTLGKKSDISRNAYSRYNTISYRKIRKGNTKQRIDE FESMMHL | 25 |
| ERMIN- in vitro citrullinated | Post translational citullination of arginine(s) in ERMIN | 26 |
| Ermin R57 | Ac-DSPLPHY(Cit)VEPSLEC-amide | 27 |
| ICAM5 | MPGPSPGLRRALLGLWAALGLGLFGLSAVSQEPFWADLQPRVAFVERGGSLWLNCSTN CPRPERGGLETSLRRNGTQRGLRWLARQLVDIREPETQPVCFFRCARRTLQARGLIRT FQRPDRVELMPLPPWQPVGENFTLSCRVPGAGPRASLTLTLLRGAQELIRRSFAGEPP RARGAVLTATVLARREDHGANFSCRAELDLRPHGLGLFENSSAPRELRTFSLSPDAPR LAAPRLLEVGSERPVSCTLDGLFPASEARVYLALGDQNLSPDVTLEGDAFVATATATA SAEQEGARQLVCNVTLGGENRETRENVTIYSFPAPLLTLSEPSVSEGQMVTVTCAAGA QALVTLEGVPAAVPGQPAQLQLNATENDDRRSFFCDATLDVDGETLIKNRSAELRVLY APRLDDSDCPRSWTWPEGPEQTLRCEARGNPEPSVHCARSDGGAVLALGLLGPVTRAL SGTYRCKAANDQGEAVKDVTLTVEYAPALDSVGCPERITWLEGTEASLSCVAHGVPPP DVICVRSGELGAVIEGLLRVAREHAGTYRCEATNPRGSAAKNVAVTVEYGPRFEEPSC PSNWTWVEGSGRLFSCEVDGKPQPSVKCVGSGGATEGVLLPLAPPDPSPRAPRIPRVL APGIYVCNATNRHGSVAKTVVVSAESPPEMDESTCPSHQTWLEGAEASALACAARGRP SPGVRCSREGIPWPEQQRVSREDAGTYHCVATNAHGTDSRTVTVGVEYRPVVAELAAS PPGGVRPGGNFTLTCRAEAWPPAQISWRAPPGALNIGLSSNNSTLSVAGAMGSHGGEY ECAATNAHGRHARRITVRVAGPWLWVAVGGAAGGAALLAAGAGLAFYVQSTACKKGEY NVQEAESSGEAVCLNGAGGGAGGAAGAEGGPEAAGGAAESPAEGEVFAIQLTSA R&D (1950-M5) | 28 |
| SNCB (Beta- synuclein) | MDVFMKGLSMAKEGVVAAAEKTKQGVTEAAEKTKEGVLYVGSKTREGVVQGVASVAEK TKEQASHLGGAVFSGAGNIAAATGLVKREEFPTDLKPEEVAQEAAEEPLIEPLMEPEG ESYEDPPQEEYQEYEPEA OriGene (TP315165) | 29 |
| MT3 (Metallothionein III) | MDPETCPCPSGGSCTCADSCKCEGCKCTSCKKSCCSCCPAECEKCAKDCVCKGGEAAE AEAEKCSCCQ | 30 |
| OMG (Oligodenrocyte Myelin Glycoprotein) | MEYQILKMSLCLFILLFLTPGILCICPLQCICTERHRHVDCSGRNLSTLPSGLQENII HLNLSYNHFTDLHNQLTQYTNLRTLDISNNRLESLPAHLPRSLWNMSAANNNIKLLDK SDTAYQWNLKYLDVSKNMLEKVVLIKNTLRSLEVLNLSSNKLWTVPTNMPSKLHIVDL SNNSLTQILPGTLINLTNLTHLYLHNNKFTFIPDQSFDQLFQLQEITLYNNRWSCDHK QNITYLLKWMMETKAHVIGTPCSTQISSLKEHNMYPTPSGFTSSLFTVSGMQTVDTIN SLSVVTQPKVTKIPKQYRTKETTFGATLSKDTTFTSTDKAFVPYPEDTSTETINSHEA AAATLTIHLQDGMVTNTSLTSSTKSSPTPMTLSITSGMPNNFSEMPQQSTTLNLWREE TTTNVKTPLPSVANAWKVNASFLLLLNVVVMLAV | 31 |
| CNDP1 (Carnosine dipeptidase 1) | | 32 |
| Reticulon 1 | MAAPGDPQDELLPLAGPGSQWLRHRGEGENEAVTPKGATPAPQAGEPSPGLGARAREA ASREAGSGPARQSPVAMETASTGVAGVSSAMDHTFSTTSKDGEGSCYTSLISDICYPP QEDSTYFTGILQKENGHVTISESPEELGTPGPSLPDVPGIESRGLFSSDSGIEMTPAE STEVNKILADPLDQMKAEAYKYIDITRPEEVKHQEQHHPELEDKDLDFKNKDTDISIK PEGVREPDKPAPVEGKIIKDHLLEESTFAPYIDDLSEEQRRAPQITTPVKITLTEIEP SVETTTQEKTPEKQDICLKPSPDTVPTVTVSEPEDDSPGSITPPSSGTEPSAAESQGK GSISEDELITAIKEAKGLSYETAENPRPVGQLADRPEVKARSGPPTIPSPLDHEASSA ESGDSEIELVSEDPMAAEDALPSGYVSFGHVGGPPPSPASPSIQYSILREEREAELDS ELIIESCDASSASEESPKREQDSPPMKPSALDAIREETGVRAEERAPSRRGLAEPGSF LDYPSTEPQPGPELPPGDGALEPETPMLPRKPEEDSSSNQSPAATKGPGPLGPGAPPP LLFLNKQKAIDLLYWRDIKQTGIVFGSFLLLLFSLTQFSVVSVVAYLALAALSATISF RIYKSVLQAVQKTDEGHPFKAYLELEITLSQEQIQKYTDCLQFYVNSTLKELRRLFLV | 33 |

TABLE 1-continued

| Antigen | Amino acid sequence or manufacture (Catalog number) | SEQ ID NO: |
|---|---|---|
| | QDLVDSLKFAVLMWLLTYVGALFNGLTLLLMAVVSMFTLPVVYVKHQAQIDQYLGLVR THINAVVAKIQAKIPGAKRHAE | |
| Astrotactin 1 | MALAGLCALLACCWGPAAVLATAAGDVDPSKELECKLKSITVSALPFLRENDLSIMHS PSASEPKLLFSVRNDFPGEMVVVDDLENTELPYFVLEISGNTEDIPLVRWRQQWLENG TLLFHIHHQDGAPSLPGQDPTEEPQHESAEEELRILHISVMGGMIALLLSILCLVMIL YTRRRWCKRRRVPQPQKSASAEAANEIHYIPSVLIGGHGRESLRNARVQGHNSSGTLS IRETPILDGYEYDITDLRHHLQRECMNGGEDFASQVTRTLDSLQGCNEKSGMDLTPGS DNAKLSLMNKYKDNIIATSPVDSNHQQATLLSHTSSSQRKRINNKARAGSAFLNPEGD SGTEAENDPQLTFYTDPSRSRRRSRVGSPRSPVNKTTLTLISITSCVIGLVCSSHVNC PLVVKITLHVPEHLIADGSRFILLEGSQLDASDWLNPAQVVLFSQQNSSGPWAMDLCA RRLLDPCEHQCDPETGECLCYEGYMKDPVHKHLCIRNEWGTNQGPWPYTIFQRGFDLV LGEQPSDKIFRFTYTLGEGMWLPLSKSFVIPPAELAINPSAKCKTDMTVMEDAVEVRE ELMTSSSFDSLEVLLDSFGPVRDCSKDNGGCSKNFRCISDRKLDSTGCVCPSGLSPMK DSSGCYDRHIGVDCSDGFNGGCEQLCLQQMAPFPDDPTLYNILMFCGCIEDYKLGVDG RSCQLITETCPEGSDCGESRELPMNQTLFGEMFFGYNNHSKEVAAGQVLKGTFRQNNF ARGLDQQLPDGLVVATVPLENQCLEEISEPTPDPDFLTGMVNFSEVSGYPVLQHWKVR SVMYHIKLNQVAISQALSNALHSLDGATSRADFVALLDQFGNHYIQEAIYGFEESCSI WYPNKQVQRRLWLEYEDISKGNSPSDESEERERDPKVLTFPEYITSLSDSGTKHMAAG VRMECHSKGRCPSSCPLCHVTSSPDTPAEPVLLEVTKAAPIYELVTNNQTQRLLQEAT MSSLWCSGTGDVIEDWCRCDSTAFGADGLPTCAPLPQPVLRLSTVHEPSSTLVVLEWE HSEPPIGVQIVDYLLRQEKVTDRMDHSKVETETVLSFVDDIISGAKSPCAMPSQVPDK QLTTISLIIRCLEPDTIYMFTLWGVDNTGRRSRPSDVIVKTPCPVVDDVKAQEIADKI YNLFNGYTSGKEQQTAYNTLLDLGSPTLHRVLYHYNQHYESFGEFTWRCEDELGPRKA GLILSQLGDLSSWCNGLLQEPKISLRRSSLKYLGCRYSEIKPYGLDWAELSRDLRKTC EEQTLSIPYNDYGDSKEI | 34 |
| Brain Angiogenesis Inhibitor 3 | uniprot# O60242 | 35 |
| Glutamate Receptor, Metabotrophic 3 | uniprot# Q14832 | 36 |
| Kelch like 32 | uniprot# Q96NJ5 | 37 |
| Matrix metallopro- teinase-9 | uniprot# P14780 | 38 |
| Melanoma Antigen Family E, 2 | uniprot# Q8TD90 | 39 |
| Neuregulin 3 | uniprot# P56975 | 40 |
| SLIT and NTRK-Like Family, Member 3 | uniprot# O94933 | 41 |
| BDNF (Brain derived neurotrophic factor) | MTILFLTMVISYFGCMKAAPMKEANIRGQGGLAYPGVRTHGTLESVNGPKAGSRGLTS LADTFEHVIEELLDEDQKVRPNEENNKDADLYTSRVMLSSQVPLEPPLLFLLEEYKNY LDAANMSMRVRRHSDPARRGELSVCDSISEWVTAADKKTAVDMSGGTVTVLEKVPVSK GQLKQYFYETKCNPMGYTKEGCRGIDKRHWNSQCRTTQSYVRALTMDSKKRIGWRHRI DTSCVCTLTIKRGR R&D (248BD005) | 42 |
| UBIQUITIN CTERMINAL HYDROLASE L1 | uniprot# P09936 | 43 |
| Oligo24 | T16G1: TTT TTT TTT TTT TTT TG | 44 |
| Tubulin beta-4B chain in vitro citrullinated | uniprot# P68371 | 45 |
| Tubulin beta-4B chain | (K)IREEYPDrIMNTF(S) | 46 |

TABLE 1-continued

List of brain injury related antigens.

| Antigen | Amino acid sequence or manufacture (Catalog number) | SEQ ID NO: |
|---|---|---|
| Tubulin alpha-1B chain | uniprot# P68363 | 47 |
| Tubulin alpha-1B chain in vitro citrullinated | | 48 |
| Tubulin alpha-1B chain | (K)YMAccLLYrGDVVPK(D) | 49 |
| Tubulin alpha-1B chain | (E)VrTGTYrQLFHPE(Q) | 50 |
| synaptotag min | uniprot# P21579 | 51 |
| AB1-42 | | 52 |
| CNPase | (K)STLArVIVDK(Y) | 53 |
| CNPase | (K)ITPGArGAFSEEYK(R) | 54 |
| Laminin | uniprot# Q13753 | 55 |
| PPIA in vitro citrullinated | uniprot# P62937 | 56 |
| PPIA | (K)TAENFrALSTGEK(G) | 57 |
| S100A10 | Uniprot# P60903 | 58 |
| Septin-7 in vitro citrullinated | | 59 |
| Septin-7 | (R)ILEQQNSSrTLEK(N) | 60 |
| Fatty acid binding Protein (FABP-3) | Prospec (PRO-340) | 61 |
| Elongation factor 1-alpha 2 in vitro citrullinated | Uniprot#Q05639 | 62 |
| Elongation factor 1-alpha 2 | (K)PLrLPLQDVYK(I) | 63 |
| Elongation factor 1-alpha 2 | (D)VYKIGGIGTVPVGrVE(T) | 64 |
| ICNPase (2',3-cyclic nucleotide 3'-phospho-diesterase) | uniprot# P09543 | 65 |
| Collagen-IV | uniprot# P02462 | 66 |
| TPPP | (K)AISSPTVSrLTDTTK(F) | 67 |
| Phospho-c-Jun | uniprot# P05412 | 68 |
| TPPP3 in vitro citrullinated | (K)TGGAVD(Cit)LTDTSrYTGSHK(E) | 69 |

TABLE 1-continued

| Antigen | Amino acid sequence or manufacture (Catalog number) | SEQ ID NO: |
|---|---|---|
| TPPP3 | (K)TGGAVDRLTDTSrYTGSHK(E) | 70 |
| TPPP3 | (K)GIAGrQDILDDSGYVSAYK(N) | 71 |
| vesicular membrane protein neurensin-1 (p24 | uniprot# Q8IZ57 | 72 |
| NDRG2, Isoform 2 in vitro citrullinated | uniprot# Q9UN36 | 73 |
| NDRG2, Isoform 2 | (R)TASLTSAASVDGNrSR(S) | 74 |
| S100 calcium binding protein B (S100B) | MSELEKAMVALIDVFHQYSGREGDKHKLKKSELKELINNELSHFLEEIKEQEVVDKVM ETLDNDGDGECDFQEFMAFVAMVTTACHEFFEHE Sigma (S6677) | 75 |
| NSE (neuron specific enolase aka ENO2) | MSIEKIWAREILDSRGNPTVEVDLYTAKGLFRAAVPSGASTGIYEALELRDGDKQRYL GKGVLKAVDHINSTIAPALISSGLSVVEQEKLDNLMLELDGTENKSKFGANAILGVSL AVCKAGAAERELPLYRHIAQLAGNSDLILPVPAFNVINGGSHAGNKLAMQEFMILPVG AESFRDAMRLGAEVYHTLKGVIKDKYGKDATNVGDEGGFAPNILENSEALELVKEAID KAGYTEKIVIGMDVAASEFYRDGKYDLDFKSPTDPSRYITGDQLGALYQDFVRDYPVV SIEDPFDQDDWAAWSKFTANVGIQIVGDDLTVTNPKRIERAVEEKACNCLLLKVNQIG SVTEAIQACKLAQENGWGVMVSHRSGETEDTFIADLVVGLCTGQIKTGAPCRSERLAK YNQLMRIEEELGDEARFAGHNFRNPSVL Abnova (H00002026-P01) | 76 |
| MCP1 (monocyte chemotactic protein-1) | Pro spec (CHM-271) | 77 |
| Tau, total | Sigma (T9392) | 78 |
| Neurofilament light polypeptide | | 79 |
| Neurofilament heavy polypeptide | | 80 |
| y-Enolase | | 81 |
| Prothrombin-FactorII | | 82 |
| EXOSC10 | uniprot# Q01780 | 83 |
| Spectrin, breakdown products | Sigma (S3644) | 84 |
| Myeloperoxidase (MPO) | Sigma (M6908) | 85 |
| CMV | Prospec (CMV Pp150) | 86 |
| ICAM | uniprot# Q8N6I2 | 87 |
| SLC39A11 | uniprot# Q8N1S5 | 88 |
| MAP2 (Microtubule-associated protein 2 | | 89 |

TABLE 1-continued

| List of brain injury related antigens. | | |
| --- | --- | --- |
| Antigen | Amino acid sequence or manufacture (Catalog number) | SEQ ID NO: |
| MAPT (microtubule-associated protein tau gene) | | 90 |
| HTR1A (Serotonin receptor 1A gene) | | 91 |
| PLXNA4 (PlexinsA4) | | 92 |
| Interleukin-6 | PVPPGEDSKD VAAPHRQPLT SSERIDKQIR YILDGISALR KETCNKSNMC ESSKEALAEN NLNLPKMAEK DGCFQSGFNE ETCLVKIITG LLEFEVYLEY LQNRFESSEE QARAVQMSTK VLIQFLQKKA KNLDAITTPD PTTNASLLTK LQAQNQWLQD MTTHLILRSF KEFLQSSLRA LRQM Peprotech (200-06) | 93 |
| Interleukin-12 | p40 Subunit: IWELKK DVYVVELDWY PDAPGEMVVL TCDTPEEDGI TWTLDQSSEV LGSGKTLTIQ VKEFGDAGQY TCHKGGEVLS HSLLLLHKKE DGIWSTDILK DQKEPKNKTF LRCEAKNYSG RFTCWWLTTI STDLTFSVKS SRGSSDPQGV TCGAATLSAE RVRGDNKEYE YSVECQEDSA CPAAEESLPI EVMVDAVHKL KYENYTSSFF IRDIIKPDPP KNLQLKPLKN SRQVEVSWEY PDTWSTPHSY FSLTFCVQVQ GKSKREKKDR VFTDKTSATV ICRKNASISV RAQDRYYSSS WSEWASVPCS Peprotech (200-12) | 94 |
| Interleukin-15 | MNWVNVISDL KKIEDLIQSM HIDATLYTES DVHPSCKVTA MKCFLLELQV ISLESGDASI HDTVENLIIL ANNSLSSNGN VTESGCKECE ELEEKNIKEF LQSFVHIVQM FINTS Peprotech (200-15) | 95 |
| Interleukin-17 | MIVKAGITIP RNPGCPNSED KNFPRTVMVN LNIHNRNTNT NPKRSSDYYN RSTSPWNLHR NEDPERYPSV IWEAKCRHLG CINADGNVDY HMNSVPIQQE ILVLRREPPH CPNSFRLEKI LVSVGCTCVT PIVHHVA Peprotech (200-17) | 96 |
| Interleukin-1ra | MRPSGRKSSK MQAFRIWDVN QKTFYLRNNQ LVAGYLQGPN VNLEEKIDVV PIEPHALFLG IHGGKMCLSC VKSGDETRLQ LEAVNITDLS ENRKQDKRFA FIRSDSGPTT SFESAACPGW FLCTAMEADQ PVSLTNMPDE GVMVTKFYFQ EDE Peprotech (200-01RA) | 97 |
| TNFRI | MDSVCPQGKY IHPQNNSICC TKCHKGTYLY NDCPGPGQDT DCRECESGSF TASENHLRHC LSCSKCRKEM GQVEISSCTV DRDTVCGCRK NQYRHYWSEN LFQCFNCSLC LNGTVHLSCQ EKQNTVCTCH AGFFLRENEC VSCSNCKKSL ECTKLCLPQI EN Peprotech (310-07) | 98 |
| VEGF | APMAEGGGQN HHEVVKFMDV YQRSYCHPIE TLVDIFQEYP DEIEYIFKPS CVPLMRCGGC CNDEGLECVP TEESNITMQI MRIKPHQGQH IGEMSFLQHN KCECRPKKDR ARQENPCGPC SERRKHLFVQ DPQTCKCSCK NTDSRCKARQ LELNERTCRC DKPRR Peprotech (100-20) | 99 |
| VCAM1 | FKIETTPESR YLAQIGDSVS LTCSTTGCES PFFSWRTQID SPLNGKVTNE GTTSTLTMNP VSFGNEHSYL CTATCESRKL EKGIQVEIYS FPKDPEIHLS GPLEAGKPIT VKCSVADVYP FDRLEIDLLK GDHLMKSQEF LEDADRKSLE TKSLEVTFTP VIEDIGKVLV CRAKLHIDEM DSVPTVRQAV KELQVYISPK NTVISVNPST KLQEGGSVTM TCSSEGLPAP EIFWSKKLDN GNLQHLSGNA TLTLIAMRME DSGIYVCEGV NLIGKNRKEV ELIVQEKPFT VEISPGPRIA AQIGDSVMLT CSVMGCESPS FSWRTQIDSP LSGKVRSEGT NSTLTLSPVS FENEHSYLCT VTCGHKKLEK GIQVELYSFP RDPEIEMSGG LVNGSSVTVS CKVPSVYPLD RLEIELLKGE TILENIEFLE DTDMKSLENK SLEMTFIPTI EDTGKALVCQ AKLHIDDMEF EPKQRQSTQT LYVNVAPRDT TVLVSPSSIL EEGSSVNMTC LSQGFPAPKI LWSRQLPNGE LQPLSENATL TLISTKMEDS GVYLCEGINQ AGRSRKEVEL IIQVTPKDIK LTAFPSESVK EGDTVIISCT CGNVPETWII LKKKAETGDT VLKSIDGAYT IRKAQLKDAG VYECESKNKV GSQLRSLTLD VQGRENNKDY FSP Peprotech (150-04) | 100 |

TABLE 1-continued

List of brain injury related antigens.

| Antigen | Amino acid sequence or manufacture (Catalog number) | SEQ ID NO: |
|---------|-----------------------------------------------------|------------|
| Factor VIIa | AKRONbiotech (AK9916) | 101 |
| Collagen II | | 102 |
| Microglobulin-b2 | Sigma (M4890) | 103 |
| TNFRSF12A | EQAPGTAPCS RGSSWSADLD KCMDCASCRA RPHSDFCLGC AAAPPAPFRL LWP<br>Peprotech (310-21) | 104 |
| TNFRII | MAPEPGSTCR LREYYDQTAQ MCCSKCSPGQ HAKVFCTKTS DTVCDSCEDS TYTQLWNWVP ECLSCGSRCS SDQVETQACT REQNRICTCR PGWYCALSKQ EGCRLCAPLR KCRPGFGVAR PGTETSDVVC KPCAPGTFSN TTSSTDICRP HQICNVVAIP GNASMDAVCT STSP<br>Peprotech (310-12) | 105 |
| CRP | Sigma (C4063) | 106 |
| BAFF-R | MRRGPRSLRG RDAPAPTPCV PAECFDLLVR HCVACGLLRT PRPKPAGASS PAPRTALQPQ ESVGAGAGEA ALPLPG<br>Peprotech (310-13R) | 107 |
| BAFF | AVQGPEETVT QDCLQLIADS ETPTIQKGSY TFVPWLLSFK RGSALEEKEN KILVKETGYF FIYGQVLYTD KTYAMGHLIQ RKKVHVFGDE LSLVTLFRCI QNMPETLPNN SCYSAGIAKL EEGDELQLAI PRENAQISLD GDVTFFGALK LL<br>Peprotech (310-13) | 108 |
| GLP1 | HAEGTFTSDV SSYLEGQAAK EFIAWLVKGR G<br>Peprotech (130-08) | 109 |
| HSP90 | Sigma (H6774) | 110 |
| EGFP | Prospec (cyt-332) | 111 |
| C4 | Sigma (C8195) | 112 |
| C3 | Sigma (C2910) | 113 |
| C1q | Prospec (pro-554) | 114 |
| Fibrinogen | AKRONbiotech (AK9026) | 115 |

Figure 1:
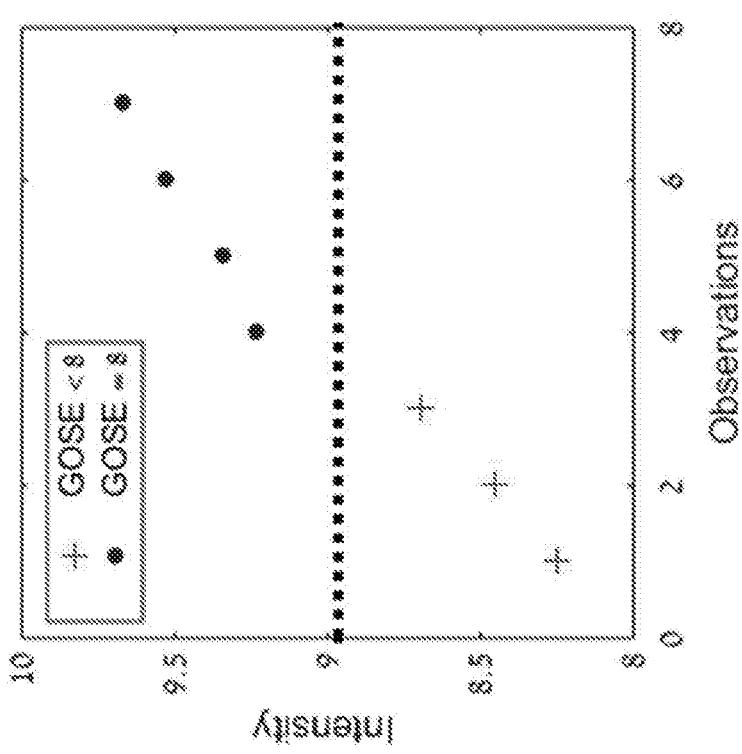
FIG. 1 illustrates anti-Fatty acid-binding protein (FABP-3, SEQ ID No: 61) IgM autoantibody levels at day 30 post brain injury. TBI patients with Glasgow Outcome Scale Extended (GOSE) score<8 (cross labeled) represent lower IgM levels than patients with GOSE score=8 (circle labeled).

As shown in FIG. 1, the levels of anti-Fatty acid-binding protein (FABP, SEQ ID No: 61) IgM autoantibodies in serum samples obtained from TBI patients at day 30 post injury, with Glasgow Outcome Scale Extended (GOSE) score<8 (cross labeled) are lower in comparison to patients with GOSE score=8 (circle labeled).

Figure 2:
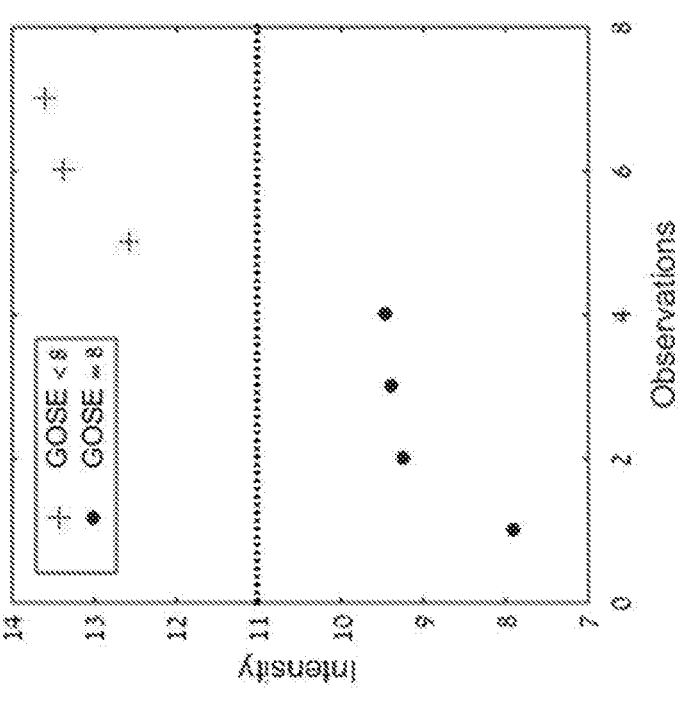
FIG. 2 illustrates anti-Myelin basic protein (MBPR149, SEQ ID No: 10) derived BSA conjugated peptide IgM autoantibody levels at day 30 post brain injury. TBI patients with Glasgow Outcome Scale Extended (GOSE) score<8 (cross labeled) represent higher IgM levels than patients with GOSE score=8 (circle labeled).

As shown in FIG. 2, the levels of anti-Myelin basic protein (MBPR149, SEQ ID No: 10, MBP derived BSA conjugated peptide) IgM autoantibodies in serum samples obtained from TBI patients at day 30 post injury, with Glasgow Outcome Scale Extended (GOSE) score<8 (cross labeled) are higher in comparison to patients with GOSE score=8 (circle labeled). These results demonstrate for the first time that increased levels of anti-FABP IgM autoantibodies in serum samples obtained from a TBI patient are indicative of recovery from brain injury of said TBI patient. Furthermore, decreased levels of anti-MBPR149 IgM autoantibodies in serum samples obtained from a TBI patient are indicative of recovery from brain injury of said TBI patient. Thus the present invention disclosed specific antigen antibody reactivities that can be used for monitoring, and/or prognosis of brain injury.

Figure 3:
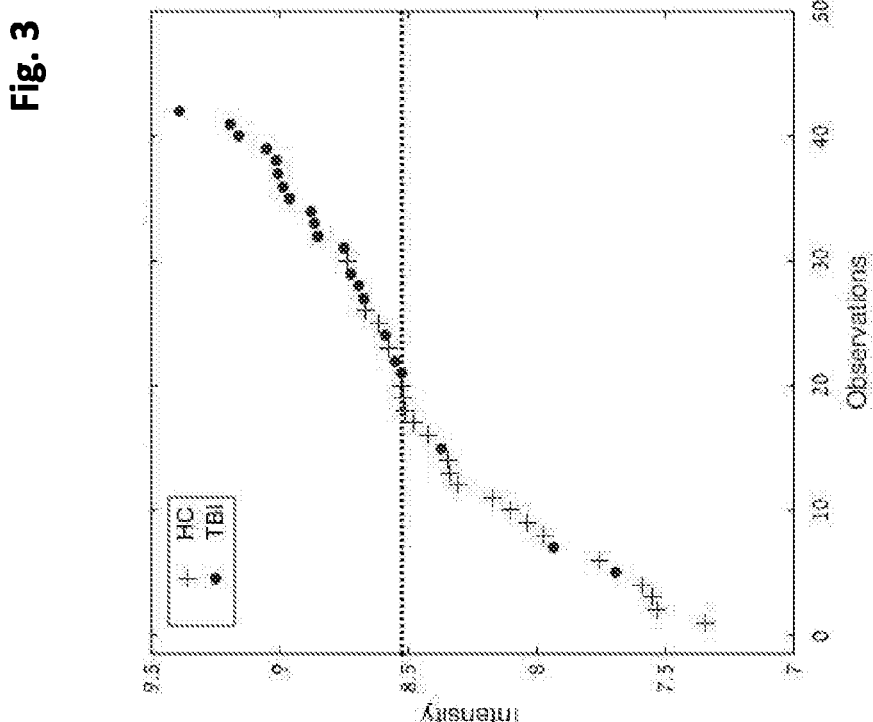
FIG. 3 illustrates anti-Myeloperoxidase (MPO, SEQ ID No: 85) IgM autoantibody levels in serum samples obtained from TBI patients (circle labeled) in comparison with healthy controls (cross labeled).

Example 2: Elevated Levels of Anti-Myeloperoxidase (MPO, SEQ ID No: 85) IgM Autoantibodies in Serum Samples Obtained From TBI Patients as Compared to Healthy Controls As shown in FIG. 3, the levels of anti-MPO IgM autoantibodies in serum samples obtained from TBI patients (circle labeled) are higher in comparison with healthy controls (cross labeled). These results demonstrate for the first time that increased levels of anti-MPO autoantibodies are indicative of brain injury.

Figures 4A, 4B:
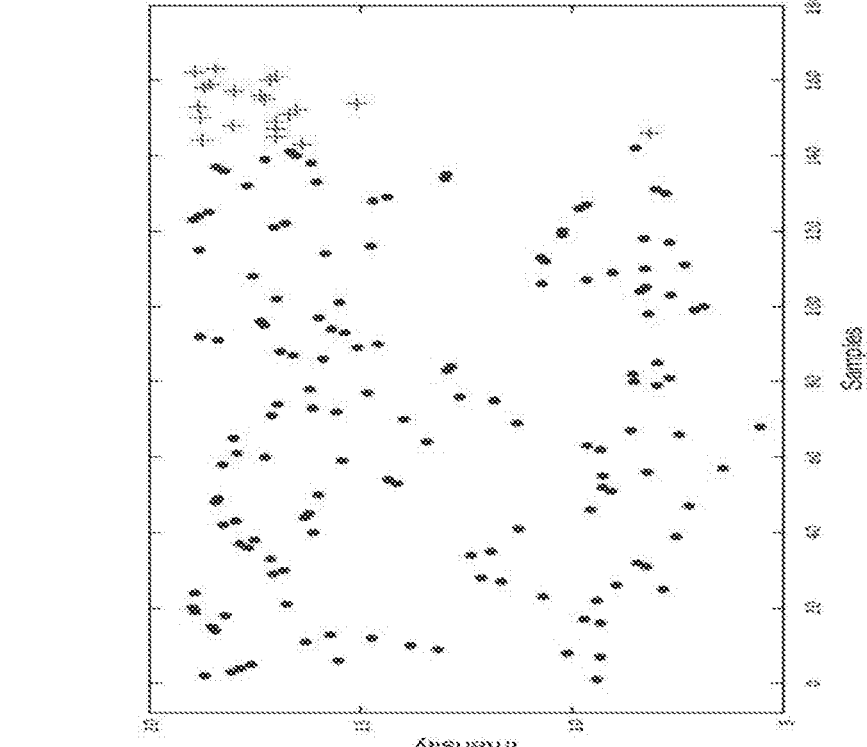
FIG. 4A illustrates anti-CMV (SEQ ID No: 86) IgG autoantibody levels in serum samples obtained from TBI patients (circle labeled) at day 30 and day 90 post injury (N=142) in comparison with healthy controls (cross labeled) (N=21).
FIG. 4B shows the above separation performance by receivers operating characteristic (ROC) curves of anti-Cytomegalovirus (CMV) IgG autoantibody levels. T test P value for separation: 3.746E-07, after FDR correction: 5.02E-05. Kruskal-Wallis test P value for separation: 4.567E-05, after FDR correction: 0.0081593.

Example 3: Decreased Levels of Anti-CMV (SEQ ID No: 86) IgG Autoantibody in Serum Samples Obtained From TBI Patients as Compared to Healthy Controls As shown in FIG. 4A, the levels of anti-CMV (SEQ ID No: 86) IgG autoantibody levels in serum samples obtained from TBI patients (circle labeled) at day 30 and day 90 post injury (N=142) are lower in comparison with healthy controls (cross labeled) (N=21). FIG. 4B shows the separation performance by receivers operating characteristic (ROC) curves of anti-CMV IgG autoantibody levels.

Figures 5A, 5B:
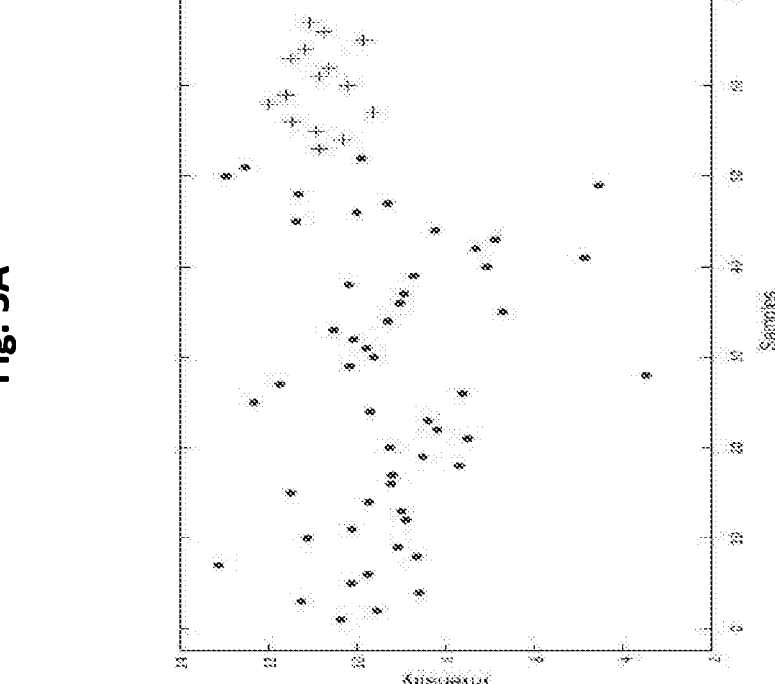
FIG. 5A demonstrates the prediction of the clinical status of TBI patients at day 90 post injury, based on the anti-TNFRSF12A (SEQ ID No: 104) IgM autoantibody levels in serum samples obtained from TBI patients at day 30 post injury. TBI patients, with GOSE<8 at day 90 post injury (circle labeled) (N=52) were compared with TBI patients, with GOSE=8 at day 90 post injury (cross labeled) (N=15).
FIG. 5B shows the above separation performance by receivers operating characteristic (ROC) curves of anti-TNFRSF12A IgM autoantibody levels. T test P value for separation: 6.808E-06, after FDR correction: 0.0036493. Kruskal-Wallis test P value for separation: 0.0004082, after FDR correction: 0.1541973

Example 4: The Prediction of the Clinical Status of
TBI Patients at Day 90 Post Injury, Based on the
Anti-TNFRSF12A (SEQ ID No: 104) IgM
Autoantibody Levels in Serum Samples Obtained
From TBI Patients at Day 30 Post Injury As shown in FIG. 5A, the levels of anti-TNFRSF12A
(SEQ ID No:104) IgM autoantibody in serum samples
obtained from TBI patients at day 30 post injury can be used
for the prediction of the clinical status (GOSE<8 or
GOSE=8) of TBI patients at day 90 post injury. FIG. 5B
shows the separation performance by receivers operating
characteristic (ROC) curves of anti-TNFRSF12A IgM
autoantibody levels.

Example 5: Combination Measurement of the
Levels of Autoantibodies and Biomarkers in Serum
Samples Obtained From TBI Patients as Compared
to Healthy Controls To determine whether combination measurement of the
levels of antibodies and biomarkers in serum samples can
differentiate between TBI patients and healthy controls, a
combined analysis was conducted. Serum samples obtained
from TBI patients at time 0 (to, N=85) were compared with
serum samples obtained from healthy control (HC, N=21).
The analysis was based on 464 iChip features (232 antigens,
IgM and IgG) and four ELISA features. iChip data is based
on average of two block replicates, following correction
procedure. ELISA features were selected based on data
availability; only features with data available for >80% of
the iChip samples were used. Samples with missing ELISA
data were removed from the analysis.

Figure 6:
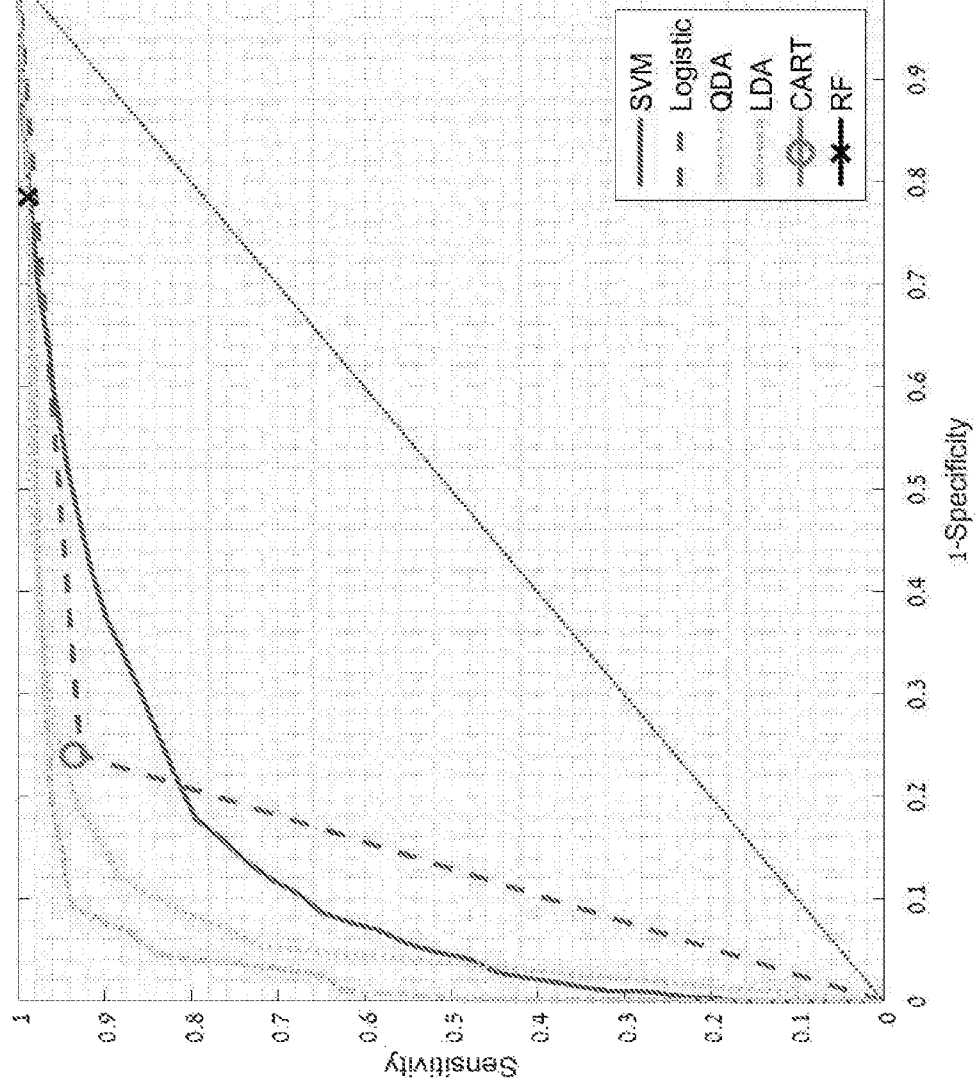
FIG. 6 shows the area under the Receiver Operating Characteristics (ROC) curves of six classification methods (SVM, LR, QDA, CART, RF and LDA) based on 100 iterations of 70:30 cross validation. Features were ranked according to their median scoring or frequency of model inclusion, depending on the method.

FIG. 6 shows the area under the Receiver Operating
Characteristics (ROC) curves of six classification methods
(SVM, LR, QDA, CART, RF and LDA) based on 100
iterations of 70:30 cross validation. Features were ranked
according to their median scoring or frequency of model
inclusion, depending on the method.

Using the LDA classification method revealed that the top
six features above the random background level are the
biomarkers: GFAP and SNCB in combination with the
autoantibodies; anti-MBP in vitro citrullinated (SEQ ID No:
2) IgM, anti-GFAP (SEQ ID No: 14) IgM, anti-ICAM5
(SEQ ID No: 28) IgM, and anti-BDNF (SEQ ID No: 42)
IgM.

Using the QDA classification method revealed that the top
three features above the random background level are the biomarkers: GFAP and SNCB in combination with the
autoantibodies: anti-MBP in vitro citrullinated (SEQ ID No:
2).

Example 6: Combination Measurement of the
Levels of Antibodies and Biomarkers in Serum
Samples Obtained From TBI Patients With
Intracranial Hemorrhage on Head CT as Compared
to TBI Patients With Normal CT To determine whether combination measurement of the
levels of antibodies and biomarkers in serum samples can
differentiate between TBI patients with intracranial hemor-
rhage on head CT and those with normal CT, a combined
analysis was conducted. Serum samples obtained from TBI
patients at time 0 (t0) with abnormal CT were compared
with samples obtained from TBI patients at time 0 (t0) with
normal CT. Analysis was based on 464 iChip features (232
antigen, IgM and IgG) and four ELISA features. iChip data
is based on average of two block replicates, following
correction procedure. ELISA features were selected based
on data availability; only features with data available for
>80% of the iChip samples were used. Samples with missing
ELISA data were removed from the analysis.

FIG. 7 shows ROC curves of six classification methods
(SVM, LR, QDA, CART, RF and LDA), based on 100
iterations of 70:30 cross validation. Features were ranked
according to their median scoring or frequency of model
inclusion, depending on the method.

Using the LDA classification method revealed that the top
five features above the random background level are the
biomarker: SNCB in combination with the autoantibodies:
anti-Collagen IV (SEQ ID No: 66) IgG, anti-Oligo24 (SEQ
ID No: 44) IgM, anti-EBV IgM and anti-Collagen II (SEQ
ID No: 102) IgG.

The foregoing description of the specific embodiments
will so fully reveal the general nature of the invention that
others can, by applying current knowledge, readily modify
and/or adapt for various applications such specific embodi-
ments without undue experimentation and without departing
from the generic concept, and, therefore, such adaptations
and modifications should and are intended to be compre-
hended within the meaning and range of equivalents of the
disclosed embodiments. It is to be understood that the
phraseology or terminology employed herein is for the
purpose of description and not of limitation. The means,
materials, and steps for carrying out various disclosed func-
tions may take a variety of alternative forms without depart-
ing from the invention.

The invention claimed is:

1. A method of detecting a biomarker protein in a subject having or suspected of having brain injury, the method comprising:

(i) detecting biomarker protein synuclein beta (SNCB) in a biological sample obtained from the subject using a detecting assay selected from an immunoassay, an antigen probe set assay, a microarray assay, a dipstick assay, or a chip assay;

(ii) measuring the level of the SNCB biomarker protein detected in the sample and comparing the level in the sample to the level of the SNCB biomarker protein present in a healthy control;

(iii) diagnosing the subject as having or suspected of having brain injury when the level of the SNCB biomarker protein measured in step (ii) is higher than the level of the SNCB biomarker protein in the healthy control; and (iv) administering a brain injury treatment or therapy to the subject diagnosed as having or suspected of having brain injury in step (iii).

2. The method of claim 1, further comprising measuring in the biological sample the levels of at least one protein selected from the group consisting of myelin basic protein (MBP), glial fibrillary acidic protein (GFAP), intercellular adhesion molecule-5 (ICAM5), brain derived neurotrophic factor (BDNF), Collagen II, Collagen IV, Oligo24 of SEQ ID NO: 44, Epstein Barr Virus (EBV) antigen, and a combination thereof; and comparing the levels of the at least one protein in the sample to the respective levels of the same proteins present in a healthy control.

3. The method of claim 1, wherein the antigen probe set assay is in the form of an array, wherein the biomarker protein is localized and detected at specific addressable locations of the array.

4. The method of claim 1, wherein the detecting assay is in the form of a kit, which optionally comprises reagents, buffers, detectable labels, and instructions for use.

5. The method of claim 1, wherein the detecting assay comprises an immunoassay selected from the group consisting of an enzymatic assay, a fluorescence assay, a luminescence assay, a colorimetric detection assay, or a combination thereof.

6. The method of claim 1, wherein the biological sample is plasma, serum, blood, or cerebrospinal fluid.

7. The method of claim 1, wherein a citrullinated form or a post-translationally modified form of the SNCB biomarker protein is detected in the biological sample.

8. The method of claim 1, further comprising detecting in the biological sample Metallothionein-3 protein (MT3).

9. The method of claim 1, wherein the healthy control comprises a biological sample obtained from a healthy individual without brain injury; a panel of samples obtained from a set of healthy individuals without brain injury; or a stored set of data obtained from healthy individuals without brain injury.

10. The method of claim 2, wherein the levels of the at least one protein in the sample are higher than the levels of the same proteins present in the healthy control.

* * * * *

SEQUENCE LISTING

```
Sequence total quantity: 115
SEQ ID NO: 1              moltype = AA  length = 197
FEATURE                   Location/Qualifiers
source                    1..197
                          mol_type = protein
                          organism = Homo sapiens
SEQUENCE: 1
MASQKRPSQR HGSKYLATAS TMDHARHGFL PRHRDTGILD SIGRFFGGDR GAPKRGSGKV  60
PWLKPGRSPL PSHARSQPGL CNMYKDSHHP ARTAHYGSLP QKSHGRTQDE NPVVHFFKNI  120
VTPRTPPPSQ GKGRGLSLSR FSWGAEGQRP GFGYGGRASD YKSAHKGFKG VDAQGTLSKI  180
FKLGGRDSRS GSPMARR                                                 197

SEQ ID NO: 2              moltype = AA  length = 197
FEATURE                   Location/Qualifiers
SITE                      6
                          note = Citrulline
SITE                      10
```

```
                        note = Citrulline
SITE                    26
                        note = Citrulline
SITE                    32
                        note = Citrulline
SITE                    34
                        note = Citrulline
SITE                    44
                        note = Citrulline
SITE                    50
                        note = Citrulline
SITE                    55
                        note = Citrulline
SITE                    67
                        note = Citrulline
SITE                    75
                        note = Citrulline
SITE                    92
                        note = Citrulline
SITE                    106
                        note = Citrulline
SITE                    124
                        note = Citrulline
SITE                    134
                        note = Citrulline
SITE                    140
                        note = Citrulline
SITE                    149
                        note = Citrulline
SITE                    157
                        note = Citrulline
SITE                    186
                        note = Citrulline
SITE                    189
                        note = Citrulline
SITE                    196
                        note = Citrulline
SITE                    197
                        note = Citrulline
source                  1..197
                        mol_type = protein
                        organism = synthetic construct
SEQUENCE: 2
MASQKXPSQX HGSKYLATAS TMDHAXHGFL PXHXDTGILD SIGXFFGGDX GAPKXGSGKV  60
PWLKPGXSPL PSHAXSQPGL CNMYKDSHHP AXTAHYGSLP QKSHGXTQDE NPVVHFFKNI  120
VTPXTPPPSQ GKGXGLSLSX FSWGAEGQXP GFGYGGXASD YKSAHKGFKG VDAQGTLSKI  180
FKLGGXDSXS GSPMAXX                                                 197

SEQ ID NO: 3            moltype = AA   length = 12
FEATURE                 Location/Qualifiers
SITE                    6
                        note = Citrulline
source                  1..12
                        mol_type = protein
                        organism = synthetic construct
SEQUENCE: 3
TMDHAXHGFL PC                                                       12

SEQ ID NO: 4            moltype = AA   length = 12
FEATURE                 Location/Qualifiers
SITE                    5
                        note = Citrulline
SITE                    7
                        note = Citrulline
source                  1..12
                        mol_type = protein
                        organism = synthetic construct
SEQUENCE: 4
GFLPXHXDTG IC                                                       12

SEQ ID NO: 5            moltype = AA   length = 12
FEATURE                 Location/Qualifiers
SITE                    8
                        note = Citrulline
source                  1..12
                        mol_type = protein
                        organism = synthetic construct
SEQUENCE: 5
CILDSIGXFF GG                                                       12
```

-continued

```
SEQ ID NO: 6            moltype = AA   length = 12
FEATURE                 Location/Qualifiers
SITE                    5
                        note = Citrulline
source                  1..12
                        mol_type = protein
                        organism = synthetic construct
SEQUENCE: 6
FGGDXGAPKR GC                                                        12

SEQ ID NO: 7            moltype = AA   length = 13
FEATURE                 Location/Qualifiers
SITE                    8
                        note = Citrulline
source                  1..13
                        mol_type = protein
                        organism = synthetic construct
SEQUENCE: 7
CDSHHPAXTA HYG                                                       13

SEQ ID NO: 8            moltype = AA   length = 12
FEATURE                 Location/Qualifiers
SITE                    7
                        note = Citrulline
source                  1..12
                        mol_type = protein
                        organism = synthetic construct
SEQUENCE: 8
CQKSHGXTQD EN                                                        12

SEQ ID NO: 9            moltype = AA   length = 11
FEATURE                 Location/Qualifiers
SITE                    9
                        note = Citrulline
source                  1..11
                        mol_type = protein
                        organism = synthetic construct
SEQUENCE: 9
CFKNIVTPXT P                                                         11

SEQ ID NO: 10           moltype = AA   length = 12
FEATURE                 Location/Qualifiers
SITE                    6
                        note = Citrulline
source                  1..12
                        mol_type = protein
                        organism = synthetic construct
SEQUENCE: 10
GAEGQXPGFG YC                                                        12

SEQ ID NO: 11           moltype = AA   length = 12
FEATURE                 Location/Qualifiers
SITE                    6
                        note = Citrulline
source                  1..12
                        mol_type = protein
                        organism = synthetic construct
SEQUENCE: 11
CGYGGXASDY KS                                                        12

SEQ ID NO: 12           moltype = AA   length = 11
FEATURE                 Location/Qualifiers
SITE                    6
                        note = Citrulline
SITE                    9
                        note = Citrulline
source                  1..11
                        mol_type = protein
                        organism = synthetic construct
SEQUENCE: 12
CKLGGXDSXS G                                                         11

SEQ ID NO: 13           moltype = AA   length = 10
FEATURE                 Location/Qualifiers
SITE                    2
                        note = Aminocaproic acid
SITE                    9
                        note = Citrulline
```

```
SITE                       10
                           note = Citrulline
source                     1..10
                           mol_type = protein
                           organism = synthetic construct
SEQUENCE: 13
CXSGSPMAXX                                                                        10

SEQ ID NO: 14              moltype = AA  length = 432
FEATURE                    Location/Qualifiers
source                     1..432
                           mol_type = protein
                           organism = Homo sapiens
SEQUENCE: 14
MERRRITSAA RRSYVSSGEM MVGGLAPGRR LGPGTRLSLA RMPPPLPTRV DFSLAGALNA  60
GFKETRASER AEMMELNDRF ASYIEKVRFL EQQNKALAAE LNQLRAKEPT KLADVYQAEL  120
RELRLRLDQL TANSARLEVE RDNLAQDLAT VRQKLQDETN LRLEAENNLA AYRQEADEAT  180
LARLDLERKI ESLEEEIRFL RKIHEEEVRE LQEQLARQQV HVELDVAKPD LTAALKEIRT  240
QYEAMASSNM HEAEEWYRSK FADLTDAAAR NAELLRQAKH EANDYRRQLQ SLTCDLESLR  300
GTNESLERQM REQEERHVRE AASYQEALAR LEEEGQSLKD EMARHLQEYQ DLLNVKLALD  360
IEIATYRKLL EGEENRITIP VQTFSNLQIR ETSLDTKSVS EGHLKRNIVV KTVEMRDGEV  420
IKESKQEHKD VM                                                     432

SEQ ID NO: 15              moltype = AA  length = 432
FEATURE                    Location/Qualifiers
SITE                       3
                           note = Citrulline
SITE                       4
                           note = Citrulline
SITE                       5
                           note = Citrulline
SITE                       11
                           note = Citrulline
SITE                       12
                           note = Citrulline
SITE                       29
                           note = Citrulline
SITE                       30
                           note = Citrulline
SITE                       36
                           note = Citrulline
SITE                       41
                           note = Citrulline
SITE                       49
                           note = Citrulline
SITE                       66
                           note = Citrulline
SITE                       70
                           note = Citrulline
SITE                       79
                           note = Citrulline
SITE                       88
                           note = Citrulline
SITE                       105
                           note = Citrulline
SITE                       121
                           note = Citrulline
SITE                       124
                           note = Citrulline
SITE                       126
                           note = Citrulline
SITE                       136
                           note = Citrulline
SITE                       141
                           note = Citrulline
SITE                       152
                           note = Citrulline
SITE                       162
                           note = Citrulline
SITE                       173
                           note = Citrulline
SITE                       183
                           note = Citrulline
SITE                       188
                           note = Citrulline
SITE                       198
                           note = Citrulline
SITE                       201
                           note = Citrulline
```

```
SITE                       209
                           note = Citrulline
SITE                       217
                           note = Citrulline
SITE                       239
                           note = Citrulline
SITE                       258
                           note = Citrulline
SITE                       270
                           note = Citrulline
SITE                       276
                           note = Citrulline
SITE                       286
                           note = Citrulline
SITE                       287
                           note = Citrulline
SITE                       300
                           note = Citrulline
SITE                       308
                           note = Citrulline
SITE                       311
                           note = Citrulline
SITE                       316
                           note = Citrulline
SITE                       319
                           note = Citrulline
SITE                       330
                           note = Citrulline
SITE                       344
                           note = Citrulline
SITE                       367
                           note = Citrulline
SITE                       376
                           note = Citrulline
SITE                       390
                           note = Citrulline
REGION                     406..416
                           note = Citrulline
source                     1..432
                           mol_type = protein
                           organism = synthetic construct
SEQUENCE: 15
MEXXXITSAA XXSYVSSGEM MVGGLAPGXX LGPGTXLSLA XMPPPLPTXV DFSLAGALNA        60
GFKETXASEX AEMMELNDXF ASYIEKVXFL EQQNKALAAE LNQLXAKEPT KLADVYQAEL       120
XELXLXLDQL TANSAXLEVE XDNLAQDLAT VXQKLQDETN LXLEAENNLA AYXQEADEAT       180
LAXLDLEXKI ESLEEEIXFL XKIHEEEVXE LQEQLAXQQV HVELDVAKPD LTAALKEIXT       240
QYEAMASSNM HEAEEWYXSK FADLTDAAAX NAELLXQAKH EANDYXXQLQ SLTCDLESLX       300
GTNESLEXQM XEQEEXHVXE AASYQEALAX LEEEGQSLKD EMAXHLQEYQ DLLNVKLALD       360
IEIATYXKLL EGEENXITIP VQTFSNLQIX ETSLDTKSVS EGHLKXNIVV KTVEMXDGEV       420
IKESKQEHKD VM                                                          432

SEQ ID NO: 16              moltype = AA  length = 12
FEATURE                    Location/Qualifiers
SITE                       6
                           note = Citrulline
source                     1..12
                           mol_type = protein
                           organism = synthetic construct
SEQUENCE: 16
LAPGRXLGPG TC                                                            12

SEQ ID NO: 17              moltype = AA  length = 12
FEATURE                    Location/Qualifiers
SITE                       7
                           note = Citrulline
source                     1..12
                           mol_type = protein
                           organism = synthetic construct
SEQUENCE: 17
CLGPGTXLSL AR                                                            12

SEQ ID NO: 18              moltype = AA  length = 11
FEATURE                    Location/Qualifiers
SITE                       3
                           note = Citrulline
source                     1..11
                           mol_type = protein
                           organism = synthetic construct
SEQUENCE: 18
```

-continued

```
AAXNAELLRQ C                                                             11

SEQ ID NO: 19            moltype = AA  length = 12
FEATURE                 Location/Qualifiers
SITE                    7
                        note = Citrulline
source                  1..12
                        mol_type = protein
                        organism = synthetic construct
SEQUENCE: 19
CEGHLKXNIV VK                                                            12

SEQ ID NO: 20            moltype = AA  length = 13
FEATURE                 Location/Qualifiers
SITE                    8
                        note = Citrulline
source                  1..13
                        mol_type = protein
                        organism = synthetic construct
SEQUENCE: 20
CVKTVEMXDG EVI                                                           13

SEQ ID NO: 21            moltype = AA  length = 78
FEATURE                 Location/Qualifiers
source                  1..78
                        mol_type = protein
                        organism = Homo sapiens
SEQUENCE: 21
MDCCTENACS KPDDDILDIP LDDPGANAAA AKIQASFRGH MARKKIKSGE RGRKGPGPGG  60
PGGAGVARGG AGGGPSGD                                                      78

SEQ ID NO: 22            moltype = AA  length = 78
FEATURE                 Location/Qualifiers
SITE                    38
                        note = Citrulline
SITE                    43
                        note = Citrulline
SITE                    51
                        note = Citrulline
SITE                    53
                        note = Citrulline
SITE                    68
                        note = Citrulline
source                  1..78
                        mol_type = protein
                        organism = synthetic construct
SEQUENCE: 22
MDCCTENACS KPDDDILDIP LDDPGANAAA AKIQASFXGH MAXKKIKSGE XGXKGPGPGG  60
PGGAGVAXGG AGGGPSGD                                                      78

SEQ ID NO: 23            moltype = AA  length = 12
FEATURE                 Location/Qualifiers
SITE                    6
                        note = Citrulline
SITE                    8
                        note = Citrulline
source                  1..12
                        mol_type = protein
                        organism = synthetic construct
SEQUENCE: 23
CKSGEXGXKG PG                                                            12

SEQ ID NO: 24            moltype = AA  length = 12
FEATURE                 Location/Qualifiers
SITE                    8
                        note = Citrulline
source                  1..12
                        mol_type = protein
                        organism = synthetic construct
SEQUENCE: 24
CGGAGVAXGG AG                                                            12

SEQ ID NO: 25            moltype = AA  length = 297
FEATURE                 Location/Qualifiers
source                  1..297
                        mol_type = protein
                        organism = Homo sapiens
SEQUENCE: 25
MKTLSPDRIQ PHIMTDVPAT FTQAECNGDK PPENGQQTIT KISEELTDVD SPLPHYRVEP  60
```

```
SLEGALTKGS QEERRKLQGN MLLNSSMEDK MLKENPEEKL FIVHKAITDL SLQETSADEM   120
TFREGHQWEK IPLSGSNQEI RRQKERITEQ PLKEEEDEDR KNKGHQAAEI EWLGFRKPSQ   180
ADMLHSKHDE EQKVWDEEID DDDDDNCNND EDEVRVIEFK KKHEEVSQFK EEGDASEDSP   240
LSSASSQAVT PDEQPTLGKK SDISRNAYSR YNTISYRKIR KGNTKQRIDE FESMMHL      297

SEQ ID NO: 26              moltype = AA  length = 297
FEATURE                    Location/Qualifiers
SITE                       8
                           note = Citrulline
SITE                       57
                           note = Citrulline
SITE                       74
                           note = Citrulline
SITE                       75
                           note = Citrulline
SITE                       123
                           note = Citrulline
SITE                       141
                           note = Citrulline
SITE                       142
                           note = Citrulline
SITE                       146
                           note = Citrulline
SITE                       160
                           note = Citrulline
SITE                       176
                           note = Citrulline
SITE                       215
                           note = Citrulline
SITE                       265
                           note = Citrulline
SITE                       270
                           note = Citrulline
SITE                       277
                           note = Citrulline
SITE                       280
                           note = Citrulline
SITE                       287
                           note = Citrulline
source                     1..297
                           mol_type = protein
                           organism = synthetic construct
SEQUENCE: 26
MKTLSPDXIQ PHIMTDVPAT FTQAECNGDK PPENGQQTIT KISEELTDVD SPLPHYXVEP   60
SLEGALTKGS QEEXXKLQGN MLLNSSMEDK MLKENPEEKL FIVHKAITDL SLQETSADEM   120
TFXEGHQWEK IPLSGSNQEI XXQKEXITEQ PLKEEEDEDX KNKGHQAAEI EWLGFXKPSQ   180
ADMLHSKHDE EQKVWDEEID DDDDDNCNND EDEVXVIEFK KKHEEVSQFK EEGDASEDSP   240
LSSASSQAVT PDEQPTLGKK SDISXNAYSX YNTISYXKIX KGNTKQXIDE FESMMHL      297

SEQ ID NO: 27              moltype = AA  length = 15
FEATURE                    Location/Qualifiers
SITE                       8
                           note = Citrulline
source                     1..15
                           mol_type = protein
                           organism = synthetic construct
SEQUENCE: 27
DSPLPHYXVE PSLEC                                                    15

SEQ ID NO: 28              moltype = AA  length = 924
FEATURE                    Location/Qualifiers
source                     1..924
                           mol_type = protein
                           organism = Homo sapiens
SEQUENCE: 28
MPGPSPGLRR ALLGLWAALG LGLFGLSAVS QEPFWADLQP RVAFVERGGS LWLNCSTNCP   60
RPERGGLETS LRRNGTQRGL RWLARQLVDI REPETQPVCF FRCARRTLQA RGLIRTFQRP   120
DRVELMPLPP WQPVGENFTL SCRVPGAGPR ASLTLTLLRG AQELIRRSFA GEPPRARGAV   180
LTATVLARRE DHGANFSCRA ELDLRPHGLG LFENSSAPRE LRTFSLSPDA PRLAAPRLLE   240
VGSERPVSCT LDGLFPASEA RVYLALGDQN LSPDVTLEGD AFVATATATA SAEQEGARQL   300
VCNVTLGGEN RETRENVTIY SFPAPLLTLS EPSVSEGQMV TVTCAAGAQA LVTLEGVPAA   360
VPGQPAQLQL NATENDDRRS FFCDATLDVD GETLIKNRSA ELRVLYAPRL DDSDCPRSWT   420
WPEGPEQTLR CEARGNPEPS VHCARSDGGA VLALGLLGPV TRALSGTYRC KAANDQGEAV   480
KDVTLTVEYA PALDSVGCPE RITWLEGTEA SLSCVAHGVP PPDVICVRSG ELGAVIEGLL   540
RVAREHAGTY RCEATNPRGS AAKNVAVTVE YGPRFEEPSC PSNWTWVEGS GRLFSCEVDG   600
KPQPSVKCVG SGGATEGVLL PLAPPDPSPR APRIPRVLAP GIYVCNATNR HGSVAKTVVV   660
SAESPPEMDE STCPSHQTWL EGAEASALAC AARGRPSPGV RCSREGIPWP EQQRVSREDA   720
GTYHCVATNA HGTDSRTVTV GVEYRPVVAE LAASPPGGVR PGGNFTLTCR AEAWPPAQIS   780
WRAPPGALNI GLSSNNSTLS VAGAMGSHGG EYECAATNAH GRHARRITVR VAGPWLWVAV   840
```

```
GGAAGGAALL AAGAGLAFYV QSTACKKGEY NVQEAESSGE AVCLNGAGGG AGGAAGAEGG   900
PEAAGGAAES PAEGEVFAIQ LTSA                                          924

SEQ ID NO: 29           moltype = AA  length = 134
FEATURE                 Location/Qualifiers
source                  1..134
                        mol_type = protein
                        organism = Homo sapiens
SEQUENCE: 29
MDVFMKGLSM AKEGVVAAAE KTKQGVTEAA EKTKEGVLYV GSKTREGVVQ GVASVAEKTK    60
EQASHLGGAV FSGAGNIAAA TGLVKREEFP TDLKPEEVAQ EAAEEPLIEP LMEPEGESYE   120
DPPQEEYQEY EPEA                                                     134

SEQ ID NO: 30           moltype = AA  length = 68
FEATURE                 Location/Qualifiers
source                  1..68
                        mol_type = protein
                        organism = Homo sapiens
SEQUENCE: 30
MDPETCPCPS GGSCTCADSC KCEGCKCTSC KKSCCSCCPA ECEKCAKDCV CKGGEAAEAE    60
AEKCSCCQ                                                             68

SEQ ID NO: 31           moltype = AA  length = 440
FEATURE                 Location/Qualifiers
source                  1..440
                        mol_type = protein
                        organism = Homo sapiens
SEQUENCE: 31
MEYQILKMSL CLFILLFLTP GILCICPLQC ICTERHRHVD CSGRNLSTLP SGLQENIIHL    60
NLSYNHFTDL HNQLTQYTNL RTLDISNNRL ESLPAHLPRS LWNMSAANNN IKLLDKSDTA   120
YQWNLKYLDV SKNMLEKVVL IKNTLRSLEV LNLSSNKLWT VPTNMPSKLH IVDLSNNSLT   180
QILPGTLINL TNLTHLYLHN NKFTFIPDQS FDQLFQLQEI TLYNNRWSCD HKQNITYLLK   240
WMMETKAHVI GTPCSTQISS LKEHNMYPTP SGFTSSLFTV SGMQTVDTIN SLSVVTQPKV   300
TKIPKQYRTK ETTFGATLSK DTTFTSTDKA FVPYPEDTST ETINSHEAAA ATLTIHLQDG   360
MVTNTSLTSS TKSSPTPMTL SITSGMPNNF SEMPQQSTTL NLWREETTTN VKTPLPSVAN   420
AWKVNASFLL LLNVVVMLAV                                               440

SEQ ID NO: 32           moltype = AA  length = 507
FEATURE                 Location/Qualifiers
source                  1..507
                        mol_type = protein
                        organism = Homo sapiens
SEQUENCE: 32
MDPKLGRMAA SLLAVLLLLL ERGMFSSPSP PPALLEKVFQ YIDLHQDEFV QTLKEWVAIE    60
SDSVQPVPRF RQELFRMMAV AADTLQRLGA RVASVDMGPQ QLPDGQSLPI PPIILAELGS   120
DPTKGTVCFY GHLDVQPADR GDGWLTDPYV LTEVDGKLYG RGATDNKGPV LAWINAVSAF   180
RALEQDLPVN IKFIIEGMEE AGSVALEELV EKEKDRFFSG VDYIVISDNL WISQRKPAIT   240
YGTRGNSYFM VEVKCRDQDF HSGTFGGILH EPMADLVALL GSLVDSSGHI LVPGIYDEVV   300
PLTEEEINTY KAIHLDLEEY RNSSRVEKFL FDTKEEILMH LWRYPSLSIH GIEGAFDEPG   360
TKTVIPGRVI GKFSIRLVPH MNVSAVEKQV TRHLEDVFSK RNSSNKMVVS MTLGLHPWIA   420
NIDDTQYLAA KRAIRTVFGT EPDMIRDGST IPIAKMFQEI VHKSVVLIPL GAVDDGEHSQ   480
NEKINRWNYI EGTKLFAAFF LEMAQLH                                       507

SEQ ID NO: 33           moltype = AA  length = 776
FEATURE                 Location/Qualifiers
source                  1..776
                        mol_type = protein
                        organism = Homo sapiens
SEQUENCE: 33
MAAPGDPQDE LLPLAGPGSQ WLRHRGEGEN EAVTPKGATP APQAGEPSPG LGARAREAAS    60
REAGSGPARQ SPVAMETAST GVAGVSSAMD HTFSTTSKDG EGSCYTSLIS DICYPPQEDS   120
TYFTGILQKE NGHVTISESP EELGTPGPSL PDVPGIESRG LFSSDSGIEM TPAESTEVNK   180
ILADPLDQMK AEAYKYIDIT RPEEVKHQEQ HHPELEDKDL DFKNKDTDIS IKPEGVREPD   240
KPAPVEGKII KDHLLEESTF APYIDDLSEE QRRAPQITTP VKITLTEIEP SVETTTQEKT   300
PEKQDICLKP SPDTVPTVTV SEPEDDSPGS ITPPSSGTEP SAAESQGKGS ISEDELITAI   360
KEAKGLSYET AENPRPVGQL ADRPEVKARS GPPTIPSPLD HEASSAESGD SEIELVSEDP   420
MAAEDALPSG YVSFGHVGGP PPSPASPSIQ YSILREEREA ELDSELIIES CDASSASEES   480
PKREQDSPPM KPSALDAIRE ETGVRAEEEA PSRRGLAEPG SFLDYPSTEP QPGPELPPGD   540
GALEPETPML PRKPEEDSSS NQSPAATKGP GPLGPGAPPP LLFLNKQKAI DLLYWRDIKQ   600
TGIVFGSFLL LLFSLTQFSV VSVVAYLALA ALSATISFRI YKSVLQAVQK TDEGHPFKAY   660
LELEITLSQE QIQKYTDCLQ FYVNSTLKEL RRLFLVQDLV DSLKFAVLMW LLTYVGALFN   720
GLTLLLMAVV SMFTLPVVYV KHQAQIDQYL GLVRTHINAV VAKIQAKIPG AKRHAE       776

SEQ ID NO: 34           moltype = AA  length = 1294
FEATURE                 Location/Qualifiers
source                  1..1294
                        mol_type = protein
                        organism = Homo sapiens
SEQUENCE: 34
```

```
MALAGLCALL ACCWGPAAVL ATAAGDVDPS KELECKLKSI TVSALPFLRE NDLSIMHSPS   60
ASEPKLLFSV RNDFPGEMVV VDDLENTELP YFVLEISGNT EDIPLVRWRQ QWLENGTLLF  120
HIHHQDGAPS LPGQDPTEEP QHESAEEELR ILHISVMGGM IALLLSILCL VMILYTRRRW  180
CKRRRVPQPQ KSASAEAANE IHYIPSVLIG GHGRESLRNA RVQGHNSSGT LSIRETPILD  240
GYEYDITDLR HHLQRECMNG GEDFASQVTR TLDSLQGCNE KSGMDLTPGS DNAKLSLMNK  300
YKDNIIATSP VDSNHQQATL LSHTSSSQRK RINNKARAGS AFLNPEGDSG TEAENDPQLT  360
FYTDPSRSRR RSRVGSPRSP VNKTTLTLIS ITSCVIGLVC SSHVNCPLVV KITLHVPEHL  420
IADGSRFILL EGSQLDASDW LNPAQVVLFS QQNSSGPWAM DLCARRLLDP CEHQCDPETG  480
ECLCYEGYMK DPVHKHLCIR NEWGTNQGPW PYTIFQRGFD LVLGEQPSDK IFRFTYTLGE  540
GMWLPLSKSF VIPPAELAIN PSAKCKTDMT VMEDAVEVRE ELMTSSSFDS LEVLLDSFGP  600
VRDCSKDNGG CSKNFRCISD RKLDSTGCVC PSGLSPMKDS SGCYDRHIGV DCSDGFNGGC  660
EQLCLQQMAP FPDDPTLYNI LMFCGCIEDY KLGVDGRSCQ LITETCPEGS DCGESRELPM  720
NQTLFGEMFF GYNNHSKEVA AGQVLKGTFR QNNFARGLDQ QLPDGLVVAT VPLENQCLEE  780
ISEPTPDPDF LTGMVNFSEV SGYPVLQHWK VRSVMYHIKL NQVAISQALS NALHSLDGAT  840
SRADFVALLD QFGNHYIQEA IYGFEESCSI WYPNKQVQRR LWLEYEDISK GNSPSDESEE  900
RERDPKVLTF PEYITSLSDS GTKHMAAGVR MECHSKGRCP SSCPLCHVTS SPDTPAEPVL  960
LEVTKAAPIY ELVTNNQTQR LLQEATMSSL WCSGTGDVIE DWCRCDSTAF GADGLPTCAP 1020
LPQPVLRLST VHEPSSTLVV LEWEHSEPPI GVQIVDYLLR QEKVTDRMDH SKVETETVLS 1080
FVDDIISGAK SPCAMPSQVP DKQLTTISLI IRCLEPDTIY MFTLWGVDNT GRRSRPSDVI 1140
VKTPCPVVDD VKAQEIADKI YNLFNGYTSG KEQQTAYNTL LDLGSPTLHR VLYHYNQHYE 1200
SFGEFTWRCE DELGPRKAGL ILSQLGDLSS WCNGLLQEPK ISLRRSSLKY LGCRYSEIKP 1260
YGLDWAELSR DLRKTCEEQT LSIPYNDYGD SKEI                              1294
```

```
SEQ ID NO: 35            moltype = AA   length = 1522
FEATURE                  Location/Qualifiers
source                   1..1522
                         mol_type = protein
                         organism = Homo sapiens
SEQUENCE: 35
MKAVRNLLIY IFSTYLLVMF GFNAAQDFWC STLVKGVIYG SYSVSEMFPK NFTNCTWTLE   60
NPDPTKYSIY LKFSKKDLSC SNFSLLAYQF DHFSHEKIKD LLRKNHSIMQ LCNSKNAFVF  120
LQYDKNFIQI RRVFPTNFPG LQKKGEEDQK SFFEFLVLNK VSPSQFGCHV LCTWLESCLK  180
SENGRTESCG IMYTKCTCPQ HLGEWGIDDQ SLILLNNVVL PLNEQTEGCL TQELQTTQVC  240
NLTREAKRPP KEEFGMMGDH TIKSQRPRSV HEKRVPQEQA DAAKFMAQTG ESGVEEWSQW  300
STCSVTCGQG SQVRTRTCVS PYGTHCSGPL RESRVCNNTA LCPVHGVWEE WSPWSLCSFT  360
CGRGQRTRTR SCTPPQYGGR PCEGPETHHK PCNIALCPVD GQWQEWSSWS QCSVTCSNGT  420
QQRSRQCTAA AHGGSECRGP WAESRECYNP ECTANGQWNQ WGHWSGCSKS CDGGWERRIR  480
TCQGAVITGQ QCEGTGEEVR RCNEQRCPAP YEICPEDYLM SMVWKRTPAG DLAFNQCPLN  540
ATGTTSRRCS LSLHGVAFWE QPSFARCISN EYRHLQHSIK EHLAKGQRML AGDGMSQVTK  600
TLLDLTQRKN FYAGDLLMSV EILRNVTDTF KRASYIPASD GVQNFFQIVS NLLDEENKEK  660
WEDAQQIYPG SIELMQVIED FIHIVGMGMM DFQNSYLMTG NVVASIQKLP AASVLTDINF  720
PMKGRKGMVD WARNSEDRVV IPKSIFTPVS SKELDESSVF VLGAVLYKNL DLILPTLRNY  780
TVINSKIIVV TIRPEPKTTD SFLEIELAHL ANGTLNPYCV LWDDSKTNES LGTWSTQGCK  840
TVLTDASHTK CLCDRLSTFA ILAQQPREII MESSGTPSVT LIVGSGLSCL ALITLAVVYA  900
ALWRYIRSER SIILINFCLS IISSNILILV GQTQTHNKSI CTTTTAFLHF FFLASFCWVL  960
TEAWQSYMAV TGKIRTRLIR KRFLCLGWGL PALVVATSVG FTRTKGYGTD HYCWLSLEGG 1020
LLYAFVGPAA AVVLVNMVIG ILVFNKLVSR DGILDKKLKH RAGQMSEPHS GLTLKCAKCG 1080
VVSTTALSAT TASNAMASLW SSCVVLPLLA LTWMSAVLAM TDKRSILFQI LFAVFDSLQG 1140
FVIVMVHCIL RREVQDAFRC RLRNCQDPIN ADSSSSFPNG HAQIMTDFEK DVDIACRSVL 1200
HKDIGPCRAA TITGTLSRIS LNDDEEEKGT NPEGLSYSTL PGNVISKVII QQPTGLHMPM 1260
SMNELSNPCL KKENSELRRT VYLCTDDNLR GADMDIVHPQ ERMMESDYIV MPRSSVNNQP 1320
SMKEESKMNI GMETLPHERL LHYKVNPEFN MNPPVMDQFN MNLEQHLAPQ EHMQNLPFEP 1380
RTAVKNFMAS ELDDNAGLSR SETGSTISMS SLERRKSRYS DLDFEKVMHT RKRHMELFQE 1440
LNQKFQTLDR FRDIPNTSSM ENPAPNKNPW DTFKNPSEYP HYTTINVLDT EAKDALELRP 1500
AEWEKCLNLP LDVQEGDFQT EV                                          1522
```

```
SEQ ID NO: 36            moltype = AA   length = 879
FEATURE                  Location/Qualifiers
source                   1..879
                         mol_type = protein
                         organism = Homo sapiens
SEQUENCE: 36
MKMLTRLQVL TLALFSKGFL LSLGDHNFLR REIKIEGDLV LGGLFPINEK GTGTEECGRI   60
NEDRGIQRLE AMLFAIDEIN KDDYLLPGVK LGVHILDTCS RDTYALEQSL EFVRASLTKV  120
DEAEYMCPDG SYAIQENIPL LIAGVIGGSY SSVSIQVANL LRLFQIPQIS YASTSAKLSD  180
KSRYDYFART VPPDFYQAKA MAEILRFFNW TYVSTVASEG DYGETGIEAF EQEARLRNIC  240
IATAEKVGRS NIRKSYDSVI RELLQKPNAR VVVLFMRSDD SRELIAAASR ANASFTWVAS  300
DGWGAQESII KGSEHVAYGA ITLELASQPV RQFDRYFQSL NPYNNHRNPW FRDFWEQKFQ  360
CSLQNKRNHR RVCDKHLAID SSNYEQESKI MFVVNAVYAM AHALHKMQRT LCPNTTKLCD  420
AMKILDGKKL YKDYLLKINF TAPFNPNKDA DSIVKFDTFG DGMGRYNVFN FQNVGGKYSY  480
LKVGHWAETL SLDVNSIHWS RNSVPTSQCS DPCAPNEMKN MQPGDVCCWI CIPCEPYEYL  540
ADEFTCMDCG SGQWPTADLT GCYDLPEDYI RWEDAWAIGP VTIACLGFMC TCMVVTVFIK  600
HNNTPLVKAS GRELCYILLF GVGLSYCMTF FFIAKPSPVI CALRRLGLGS SFAICYSALL  660
TKTNCIARIF DGVKNGAQRP KFISPSSQVF ICLGLILVQI VMVSVWLILE APGTRRYTLA  720
EKRETVILKC NVKDSSMLIS LTYDVILVIL CTVYAFKTRK CPENFNEAKF IGFTMYTTCI  780
IWLAFLPIFY VTSSDYRVQT TTMCISVSLS GFVVLGCLFA PKVHIILFQP QKNVVTHRLH  840
LNRFSVSGTG TTYSQSSAST YVPTVCNGRE VLDSTTSSL                        879
```

```
SEQ ID NO: 37            moltype = AA   length = 620
```

```
FEATURE                    Location/Qualifiers
source                     1..620
                           mol_type = protein
                           organism = Homo sapiens
SEQUENCE: 37
MPSERCLSIQ EMLTGQRLCH SESHNDSVLA ALNQQRSDGI LCDITLIAEE QKFHAHKAVL      60
AACSDYFRAM FSLCMVESGA DEVNLHGVTS LGLKQALEFA YTGQILLEPG VIQDVLAAGS     120
HLQLLELLNL CSHYLIQELN SFNYLDLYRL ADLFNLTLLE KAVIDFLVKH LSELLKSRPE     180
EVLTLPYCLL QEVLKSDRLT SLSEEQIWQL AVRWLEHNCH YQYMDELLQY IRFGLMDVDT     240
LHTVALSHPL VQASETATAL VNEALEYHQS IYAQPVWQTR RTKPRFQSDT LYIIGGKKRE     300
VCKVKELRYF NPVDQENALI AAIANWSELA PMPVGRSHHC VAVMGDFLFV AGGEVEHASG     360
RTCAVRTACR YDPRSNSWAE IAPMKNCREH FVLGAMEEYL YAVGGRNELR QVLPTVERYC     420
PKKNKWTFVQ SFDRSLSCHA GYVADGLLWI SGGVTNTAQY QNRLMVYEPN QNKWISRSPM     480
LQRRVYHSMA AVQRKLYVLG GNDLDYNNDR ILVRHIDSYN IDTDQWTRCN FNLLTGQNES     540
GVAVHNGRIY LVGGYSIWTN EPLACIQVLD VSREGKEEVF YGPTLPFASN GIAACFLPAP     600
YFTCPNLQTL QVPHHRIGTI                                                 620

SEQ ID NO: 38              moltype = AA  length = 707
FEATURE                    Location/Qualifiers
source                     1..707
                           mol_type = protein
                           organism = Homo sapiens
SEQUENCE: 38
MSLWQPLVLV LLVLGCCFAA PRQRQSTLVL FPGDLRTNLT DRQLAEEYLY RYGYTRVAEM      60
RGESKSLGPA LLLLQKQLSL PETGELDSAT LKAMRTPRCG VPDLGRFQTF EGDLKWHHHN     120
ITYWIQNYSE DLPRAVIDDA FARAFALWSA VTPLTFTRVY SRDADIVIQF GVAEHGDGYP     180
FDGKDGLLAH AFPPGPGIQG DAHFDDDELW SLGKGVVVPT RFGNADGAAC HFPFIFEGRS     240
YSACTTDGRS DGLPWCSTTA NYDTDDRFGF CPSERLYTQD GNADGKPCQF PPIFQGQSYS     300
ACTTDGRSDG YRWCATTANY DRDKLFGFCP TRADSTVMGG NSAGELCVFP FTFLGKEYST     360
CTSEGRGDGR LWCATTSNFD SDKKWGFCPD QGYSLFLVAA HEFGHALGLD HSSVPEALMY     420
PMYRFTEGPP LHKDDVNGIR HLYGPRPEPE PRPPTTTTPQ PTAPPTVCPT GPPTVHPSER     480
PTAGPTGPPS AGPTGPPTAG PSTATTVPLS PVDDACNVNI FDAIAEIGNQ LYLFKDGKYW     540
RFSEGRGSRP QGPFLIADKW PALPRKLDSV FEERLSKKLF FFSGRQVWVY TGASVLGPRR     600
LDKLGLGADV AQVTGALRSG RGKMLLFSGR RLWRFDVKAQ MVDPRSASEV DRMFPGVPLD     660
THDVFQYREK AYFCQDRFYW RVSSRSELNQ VDQVGYVTYD ILQCPED                   707

SEQ ID NO: 39              moltype = AA  length = 523
FEATURE                    Location/Qualifiers
source                     1..523
                           mol_type = protein
                           organism = Homo sapiens
SEQUENCE: 39
MSLVSQNARH CSAEITADYG DGRGEIQATN ASGSPTSMLV VDAPQCPQAP INSQCVNTSQ      60
AVQDPNDLEV LIDEQSRRLG ALRVHDPLED RSIALVNFMR MKSQTEGSIQ QSEMLEFLRE     120
YSDQFPEILR RASAHLDQVF GLNLRVIDPQ ADTYNLVSKR GFQITDRIAE SLDMPKASLL     180
ALVLGHILLN GNRAREASIW DLLLKVDMWD KPQRINNLFG NTRNLLTTDF VCMRFLEYWP     240
VYGTNPLEFE FLWGSRAHRE ITKMEALKFV SDAHDEEWYS WPEEYNKALE SDKTKERSLT     300
AGLEFWSEDT MNDKANDLVQ LAISVTEEML PIHQDELLAH TGKEFEDVFP NILNRATLIL     360
DMFYGLSLIE VDTSEHIYLL VQQPESEEEQ VMLESLGRPT QEYVMPILGL IFLMGNRVKE     420
ANVWNLLRRF SVDVGRKHSI TRKLMRQRYL ECRPLSYSNP VEYELLWGPR AHHETIKMKV     480
LEYMARLYRK RPQNWPEQYR EAVEDEEARA KSEATIMFFL DPT                       523

SEQ ID NO: 40              moltype = AA  length = 720
FEATURE                    Location/Qualifiers
source                     1..720
                           mol_type = protein
                           organism = Homo sapiens
SEQUENCE: 40
MSEGAAAASP PGAASAAAAS AEEGTAAAAA AAAAGGGPDG GGEGAAEPPR ELRCSDCIVW      60
NRQQTWLCVV PLFIGFIGLG LSLMLLKWIV VGSVKEYVPT DLVDSKGMGQ DPFFLSKPSS     120
FPKAMETTTT TTSTTSPATP SAGGAASSRT PNRISTRLTT ITRAPTRFPG HRVPIRASPR     180
STTARNTAAP ATVPSTTAPF FSSSTLGSRP PVPGTPSTQA MPSWPTAAYA TSSYLHDSTP     240
SWTLSPFQDA ASSSSSSSSS ATTTTPETST SPKFHTTTYS TERSEHFKPC RDKDLAYCLN     300
DGECFVIETL TGSHKHCRCK EGYQGVRCDQ FLPKTDSILS DPTDHLGIEF MESEEVYQRQ     360
VLSISCIIFG IVIVGMFCAA FYFKSKKQAK QIQEQLKVPQ NGKSYSLKAS STMAKSENLV     420
KSHVQLQNYS KVERHPVTAL EKMMESSFVG PQSFPEVPSP DRGSQSVKHH RSLSSCCSPG     480
QRSGMLHRNA FRRTPPSPRS RLGGIVGPAY QQLEESRIPD QDTIPCQGIE VRKTISHLPI     540
QLWCVERPLD LKYSSSGLKT QRNTSINMQL PSRETNPYFN SLEQKDLVGY SSTRASSVPI     600
IPSVGLEETC LQMPGISEVK SIKWCKNSYS ADVVNVSIPV SDCLIAEQQE VKILLETVQE     660
QIRILTDARR SEDYELASVE TEDSASENTA FLPLSPTAKS EREAQFVLRN EIQRDSALTK     720

SEQ ID NO: 41              moltype = AA  length = 977
FEATURE                    Location/Qualifiers
source                     1..977
                           mol_type = protein
                           organism = Homo sapiens
SEQUENCE: 41
MKPSIAEMLH RGRMLWIILL STIALGWTTP IPLIEDSEEI DEPCFDPCYC EVKESLFHIH      60
CDSKGFTNIS QITEFWSRPF KLYLQRNSMR KLYTNSFLHL NNAVSINLGN NALQDIQTGA     120
```

```
FNGLKILKRL YLHENKLDVF RNDTFLGLES LEYLQADYNV IKRIESGAFR NLSKLRVLIL    180
NDNLIPMLPT NLFKAVSLTH LDLRGNRLKV LFYRGMLDHI GRSLMELQLE ENPWNCTCEI    240
VQLKSWLERI PYTALVGDIT CETPFHFHGK DLREIRKTEL CPLLSDSEVE ASLGIPHSSS    300
SKENAWPTKP SSMLSSVHFT ASSVEYKSSN KQPKPTKQPR TPRPPSTSQA LYPGPNQPPI    360
APYQTRPPIP IICPTGCTCN LHINDLGLTV NCKERGFNNI SELLPRPLNA KKLYLSSNLI    420
QKIYRSDFWN FSSLDLLHLG NNRISYVQDG AFINLPNLKS LFLNGNDIEK LTPGMFRGLQ    480
SLHYLYFEFN VIREIQPAAF SLMPNLKLLF LNNNLLRTLP TDAFAGTSLA RLNLRKNYFL    540
YLPVAGVLEH LNAIVQIDLN ENPWDCTCDL VPFKQWIETI SSVSVVGDVL CRSPENLTHR    600
DVRTIELEVL CPEMLHVAPA GESPAQPGDS HLIGAPTSAS PYEFSPPGGP VPLSVLILSL    660
LVLFFSAVFV AAGLFAYVLR RRRKKLPFRS KRQEGVDLTG IQMQCHRLFE DGGGGGGGSG    720
GGGRPTLSSP EKAPPVGHVY EYIPHPVTQM CNNPIYKPRE EEEVAVSSAQ EAGSAERGGP    780
GTQPPGMGEA LLGSEQFAET PKENHSNYRT LLEKEKEWAL AVSSSQLNTI VTVNHHHPHH    840
PAVGGVSGVV GGTGGDLAGF RHHEKNGGVV LFPPGGGCGS GSMLLDRERP QPAPCTVGFV    900
DCLYGTVPKL KELHVHPPGM QYPDLQQDAR LKETLLFSAG KGFTDHQTQK SDYLELRAKL    960
QTKPDYLEVL EKTTYRF                                                    977

SEQ ID NO: 42            moltype = AA   length = 247
FEATURE                  Location/Qualifiers
source                   1..247
                         mol_type = protein
                         organism = Homo sapiens
SEQUENCE: 42
MTILFLTMVI SYFGCMKAAP MKEANIRGQG GLAYPGVRTH GTLESVNGPK AGSRGLTSLA     60
DTFEHVIEEL LDEDQKVRPN EENNKDADLY TSRVMLSSQV PLEPPLLFLL EEYKNYLDAA    120
NMSMRVRRHS DPARRGELSV CDSISEWVTA ADKKTAVDMS GGTVTVLEKV PVSKGQLKQY    180
FYETKCNPMG YTKEGCRGID KRHWNSQCRT TQSYVRALTM DSKKRIGWRF IRIDTSCVCT    240
LTIKRGR                                                              247

SEQ ID NO: 43            moltype = AA   length = 223
FEATURE                  Location/Qualifiers
source                   1..223
                         mol_type = protein
                         organism = Homo sapiens
SEQUENCE: 43
MQLKPMEINP EMLNKVLSRL GVAGQWRFVD VLGLEEESLG SVPAPACALL LLFPLTAQHE     60
NPRKKQIEEL KGQEVSPKVY FMKQTIGNSC GTIGLIHAVA NNQDKLGFED GSVLKQFLSE    120
TEKMSPEDRA KCFEKNEAIQ AAHDAVAQEG QCRVDDKVNF HFILFNNVDG HLYELDGRMP    180
FPVNHGASSE DTLLKDAAKV CREFTEREQG EVRFSAVALC KAA                      223

SEQ ID NO: 44            moltype = DNA   length = 17
FEATURE                  Location/Qualifiers
source                   1..17
                         mol_type = other DNA
                         organism = synthetic construct
SEQUENCE: 44
tttttttttt ttttttg                                                    17

SEQ ID NO: 45            moltype = AA   length = 445
FEATURE                  Location/Qualifiers
SITE                     2
                         note = Citrulline
SITE                     46
                         note = Citrulline
SITE                     62
                         note = Citrulline
SITE                     77
                         note = Citrulline
SITE                     86
                         note = Citrulline
SITE                     121
                         note = Citrulline
SITE                     156
                         note = Citrulline
SITE                     162
                         note = Citrulline
SITE                     213
                         note = Citrulline
SITE                     241
                         note = Citrulline
SITE                     251
                         note = Citrulline
SITE                     262
                         note = Citrulline
SITE                     276
                         note = Citrulline
SITE                     282
                         note = Citrulline
SITE                     306
                         note = Citrulline
```

-continued

```
SITE                     309
                         note = Citrulline
SITE                     318
                         note = Citrulline
SITE                     320
                         note = Citrulline
SITE                     359
                         note = Citrulline
SITE                     380
                         note = Citrulline
SITE                     390
                         note = Citrulline
SITE                     391
                         note = Citrulline
source                   1..445
                         mol_type = protein
                         organism = synthetic construct
SEQUENCE: 45
MXEIVHLQAG QCGNQIGAKF WEVISDEHGI DPTGTYHGDS DLQLEXINVY YNEATGGKYV  60
PXAVLVDLEP GTMDSVXSGP FGQIFXPDNF VFGQSGAGNN WAKGHYTEGA ELVDSVLDVV  120
XKEAESCDCL QGFQLTHSLG GGTGSGMGTL LISKIXEEYP DXIMNTFSVV PSPKVSDTVV  180
EPYNATLSVH QLVENTDETY CIDNEALYDI CFXTLKLTTP TYGDLNHLVS ATMSGVTTCL  240
XFPGQLNADL XKLAVNMVPF PXLHFFMPGF APLTSXGSQQ YXALTVPELT QQMFDAKNMM  300
AACDPXHGXY LTVAAVFXGX MSMKEVDEQM LNVQNKNSSY FVEWIPNNVK TAVCDIPPXG  360
LKMSATFIGN STAIQELFKX ISEQFTAMFX XKAFLHWYTG EGMDEMEFTE AESNMNDLVS  420
EYQQYQDATA EEEGEFEEEA EEEVA                                        445

SEQ ID NO: 46            moltype = AA  length = 15
FEATURE                  Location/Qualifiers
VARIANT                  1
                         note = lysine or no amino acid
VARIANT                  15
                         note = serine or no amino acid
source                   1..15
                         mol_type = protein
                         organism = synthetic construct
SEQUENCE: 46
XIREEYPDRI MNTFX                                                   15

SEQ ID NO: 47            moltype = AA  length = 451
FEATURE                  Location/Qualifiers
source                   1..451
                         mol_type = protein
                         organism = Homo sapiens
SEQUENCE: 47
MRECISIHVG QAGVQIGNAC WELYCLEHGI QPDGQMPSDK TIGGGDDSFN TFFSETGAGK  60
HVPRAVFVDL EPTVIDEVRT GTYRQLFHPE QLITGKEDAA NNYARGHYTI GKEIIDLVLD  120
RIRKLADQCT GLQGFLVFHS FGGGTGSGFT SLLMERLSVD YGKKSKLEFS IYPAPQVSTA  180
VVEPYNSILT THTTLEHSDC AFMVDNEAIY DICRRNLDIE RPTYTNLNRL ISQIVSSITA  240
SLRFDGALNV DLTEFQTNLV PYPRIHFPLA TYAPVISAEK AYHEQLSVAE ITNACFEPAN  300
QMVKCDPRHG KYMACCLLYR GDVVPKDVNA AIATIKTKRS IQFVDWCPTG FKVGINYQPP  360
TVVPGGDLAK VQRAVCMLSN TTAIAEAWAR LDHKFDLMYA KRAFVHWYVG EGMEEGEFSE  420
AREDMAALEK DYEEVGVDSV EGEGEEEGEE Y                                 451

SEQ ID NO: 48            moltype = AA  length = 451
FEATURE                  Location/Qualifiers
source                   1..451
                         mol_type = protein
                         organism = Homo sapiens
SEQUENCE: 48
MRECISIHVG QAGVQIGNAC WELYCLEHGI QPDGQMPSDK TIGGGDDSFN TFFSETGAGK  60
HVPRAVFVDL EPTVIDEVRT GTYRQLFHPE QLITGKEDAA NNYARGHYTI GKEIIDLVLD  120
RIRKLADQCT GLQGFLVFHS FGGGTGSGFT SLLMERLSVD YGKKSKLEFS IYPAPQVSTA  180
VVEPYNSILT THTTLEHSDC AFMVDNEAIY DICRRNLDIE RPTYTNLNRL ISQIVSSITA  240
SLRFDGALNV DLTEFQTNLV PYPRIHFPLA TYAPVISAEK AYHEQLSVAE ITNACFEPAN  300
QMVKCDPRHG KYMACCLLYR GDVVPKDVNA AIATIKTKRS IQFVDWCPTG FKVGINYQPP  360
TVVPGGDLAK VQRAVCMLSN TTAIAEAWAR LDHKFDLMYA KRAFVHWYVG EGMEEGEFSE  420
AREDMAALEK DYEEVGVDSV EGEGEEEGEE Y                                 451

SEQ ID NO: 49            moltype = AA  length = 17
FEATURE                  Location/Qualifiers
VARIANT                  1
                         note = lysine or no amino acid
VARIANT                  17
                         note = aspartic acid or no amino acid
source                   1..17
                         mol_type = protein
                         organism = synthetic construct
SEQUENCE: 49
```

-continued

```
XYMACCLLYR GDVVPKX                                              17

SEQ ID NO: 50           moltype = AA  length = 15
FEATURE                 Location/Qualifiers
VARIANT                 1
                        note = glutamic acid or no amino acid
VARIANT                 15
                        note = glutamine or no amino acid
source                  1..15
                        mol_type = protein
                        organism = synthetic construct
SEQUENCE: 50
XVRTGTYRQL FHPEX                                                15

SEQ ID NO: 51           moltype = AA  length = 422
FEATURE                 Location/Qualifiers
source                  1..422
                        mol_type = protein
                        organism = Homo sapiens
SEQUENCE: 51
MVSESHHEAL AAPPVTTVAT VLPSNATEPA SPGEGKEDAF SKLKEKFMNE LHKIPLPPWA  60
LIAIAIVAVL LVLTCCFCIC KKCLFKKKNK KKGKEKGGKN AINMKDVKDL GKTMKDQALK  120
DDDAETGLTD GEEKEEPKEE EKLGKLQYSL DYDFQNNQLL VGIIQAAELP ALDMGGTSDP  180
YVKVFLLPDK KKKFETKVHR KTLNPVFNEQ FTFKVPYSEL GGKTLVMAVY DFDRFSKHDI  240
IGEFKVPMNT VDFGHVTEEW RDLQSAEKEE QEKLGDICFS LRYVPTAGKL TVVILEAKNL  300
KKMDVGGLSD PYVKIHLMQN GKRLKKKKTT IKKNTLNPYY NESFSFEVPF EQIQKVQVVV  360
TVLDYDKIGK NDAIGKVFVG YNSTGAELRH WSDMLANPRR PIAQWHTLQV EEEVDAMLAV  420
KK                                                              422

SEQ ID NO: 52           moltype = AA  length = 42
FEATURE                 Location/Qualifiers
source                  1..42
                        mol_type = protein
                        organism = Homo sapiens
SEQUENCE: 52
DAEFRHDSGY EVHHQKLVFF AEDVGSNKGA IIGLMVGGVV IA                   42

SEQ ID NO: 53           moltype = AA  length = 12
FEATURE                 Location/Qualifiers
VARIANT                 1
                        note = lysine or no amino acid
VARIANT                 12
                        note = tyrosine or no amino acid
source                  1..12
                        mol_type = protein
                        organism = synthetic construct
SEQUENCE: 53
XSTLARVIVD KX                                                    12

SEQ ID NO: 54           moltype = AA  length = 16
FEATURE                 Location/Qualifiers
VARIANT                 1
                        note = lysine or no amino acid
VARIANT                 16
                        note = arginine or no amino acid
source                  1..16
                        mol_type = protein
                        organism = synthetic construct
SEQUENCE: 54
XITPGARGAF SEEYKX                                                16

SEQ ID NO: 55           moltype = AA  length = 1193
FEATURE                 Location/Qualifiers
source                  1..1193
                        mol_type = protein
                        organism = Homo sapiens
SEQUENCE: 55
MPALWLGCCL CFSLLLLPAAR ATSRREVCDC NGKSRQCIFD RELHRQTGNG FRCLNCNDNT  60
DGIHCEKCKN GFYRHRERDR CLPCNCNSKG SLSARCDNSG RCSCKPGVTG ARCDRCLPGF  120
HMLTDAGCTQ DQRLLDSKCD CDPAGIAGPC DAGRCVCKPA VTGERCDRCR SGYYNLDGGN  180
PEGCTQCFCY GHSASCRSSA EYSVHKITST FHQDVDGWKA VQRNGSPAKL QWSQRHQDVF  240
SSAQRLDPVY FVAPAKFLGN QQVSYGQSLS FDYRVDRGGR HPSAHDVILE GAGLRITAPL  300
MPLGKTLPCG LTKTYTFRLN EHPSNNWSPQ LSYFEYRRLL RNLTALRIRA TYGEYSTGYI  360
DNVTLISARP VSGAPAPWVE QCICPVGYKG QFCQDCASGY KRDSARLGPF GTCIPCNCQG  420
GGACDPDTGD CYSGDENPDI ECADCPIGFY NDPHDPRSCK PCPCHNGFSC SVMPETEEVV  480
CNNCPPGVTG ARCELCADGY FGDPFGEHGP VRPCQPCQCN NNVDPSASGN CDRLTGRCLK  540
CIHNTAGIYC DQCKAGYFGD PLAPNPADKC RACNCNPMGS EPVGCRSDGT CVCKPGFGGP  600
NCEHGAFSCP ACYNQVKIQM DQFMQQLQRM EALISKAQGG DGVVPDTELE GRMQQAEQAL  660
QDILRDAQIS EGASRSLGLQ LAKVRSQENS YQSRLDDLKM TVERVRALGS QYQNRVRDTH  720
```

-continued

```
RLITQMQLSL AESEASLGNT NIPASDHYVG PNGFKSLAQE ATRLAESHVE SASNMEQLTR   780
ETEDYSKQAL SLVRKALHEG VGSGSGSPDG AVVQGLVEKL EKTKSLAQQL TREATQAEIE   840
ADRSYQHSLR LLDSVSRLQG VSDQSFQVEE AKRIKQKADS LSSLVTRHMD EFKRTQKNLG   900
NWKEEAQQLL QNGKSGREKS DQLLSRANLA KSRAQEALSM GNATFYEVES ILKNLREFDL   960
QVDNRKAEAE EAMKRLSYIS QKVSDASDKT QQAERALGSA AADAQRAKNG AGEALEISSE  1020
IEQEIGSLNL EANVTADGAL AMEKGLASLK SEMREVEGEL ERKELEFDTN MDAVQMVITE  1080
AQKVDTRAKN AGVTIQDTLN TLDGLLHLMD QPLSVDEEGL VLLEQKLSRA KTQINSQLRP  1140
MMSELEERAR QQRGHLHLLE TSIDGILADV KNLENIRDNL PPGCYNTQAL EQQ         1193

SEQ ID NO: 56             moltype = AA  length = 165
FEATURE                   Location/Qualifiers
SITE                      19
                          note = Citrulline
SITE                      37
                          note = Citrulline
SITE                      55
                          note = Citrulline
SITE                      69
                          note = Citrulline
SITE                      144
                          note = Citrulline
SITE                      148
                          note = Citrulline
source                    1..165
                          mol_type = protein
                          organism = synthetic construct
SEQUENCE: 56
MVNPTVFFDI AVDGEPLGXV SFELFADKVP KTAENFXALS TGEKGFGYKG SCFHXIIPGF   60
MCQGGDFTXH NGTGGKSIYG EKFEDENFIL KHTGPGILSM ANAGPNTNGS QFFICTAKTE  120
WLDGKHVVFG KVKEGMNIVE AMEXFGSXNG KTSKKITIAD CGQLE                  165

SEQ ID NO: 57             moltype = AA  length = 14
FEATURE                   Location/Qualifiers
VARIANT                   1
                          note = lysine or no amino acid
VARIANT                   14
                          note = glycine or no amino acid
source                    1..14
                          mol_type = protein
                          organism = synthetic construct
SEQUENCE: 57
XAENFRALST GEKX                                                     14

SEQ ID NO: 58             moltype = AA  length = 60
FEATURE                   Location/Qualifiers
source                    1..60
                          mol_type = protein
                          organism = Homo sapiens
SEQUENCE: 58
MPSQMEHAME TMMFTFHKFA GDKGYLTKED LRVLMEKEFP GFLENQKDPL AVDKIMKDLD   60

SEQ ID NO: 59             moltype = AA  length = 37
FEATURE                   Location/Qualifiers
SITE                      3
                          note = Citrulline
source                    1..37
                          mol_type = protein
                          organism = synthetic construct
SEQUENCE: 59
QCXDGKVGFQ SFFSLIAGLT IACNDYFVVH MKQKGKK                            37

SEQ ID NO: 60             moltype = AA  length = 15
FEATURE                   Location/Qualifiers
VARIANT                   1
                          note = arginine or no amino acid
VARIANT                   15
                          note = asparagine or no amino acid
source                    1..15
                          mol_type = protein
                          organism = synthetic construct
SEQUENCE: 60
XILEQQNSSR TLEKX                                                    15

SEQ ID NO: 61             moltype = AA  length = 133
FEATURE                   Location/Qualifiers
source                    1..133
                          mol_type = protein
                          organism = Homo sapiens
SEQUENCE: 61
```

-continued

```
MADAFLGTWK LVDSKNFDDY MKSLGVGFAT RQVASMTKPT TIIEKNGDIL TLKTHSTFKN  60
TEISFKLGVE FDETTADDRK VKSIVTLDGG KLVHLQKWDG QETTLVRELI DGKLILTLTH  120
GTAVCTRTYE KEA                                                     133

SEQ ID NO: 62           moltype = AA  length = 463
FEATURE                 Location/Qualifiers
SITE                    37
                        note = Citrulline
SITE                    67
                        note = Citrulline
SITE                    69
                        note = Citrulline
SITE                    96
                        note = Citrulline
SITE                    134
                        note = Citrulline
SITE                    166
                        note = Citrulline
SITE                    218
                        note = Citrulline
SITE                    240
                        note = Citrulline
SITE                    247
                        note = Citrulline
SITE                    266
                        note = Citrulline
SITE                    273
                        note = Citrulline
SITE                    321
                        note = Citrulline
SITE                    322
                        note = Citrulline
SITE                    381
                        note = Citrulline
SITE                    382
                        note = Citrulline
SITE                    423
                        note = Citrulline
SITE                    427
                        note = Citrulline
SITE                    430
                        note = Citrulline
source                  1..463
                        mol_type = protein
                        organism = synthetic construct
SEQUENCE: 62
MGKEKTHINI VVIGHVDSGK STTTGHLIYK CGGIDKXTIE KFEKEAAEMG KGSFKYAWVL  60
DKLKAEXEXG ITIDISLWKF ETTKYYITII DAPGHXDFIK NMITGTSQAD CAVLIVAAGV  120
GEFEAGISKN GQTXEHALLA YTLGVKQLIV GVNKMDSTEP AYSEKXYDEI VKEVSAYIKK  180
IGYNPATVPF VPISGWHGDN MLEPSPNMPW FKGWKVEXKE GNASGVSLLE ALDTILPPTX  240
PTDKPLXLPL QDVYKIGGIG TVPVGXVETG ILXPGMVVTF APVNITTEVK SVEMHHEALS  300
EALPGDNVGF NVKNVSVKDI XXGNVCGDSK SDPPQEAAQF TSQVIILNHP GQISAGYSPV  360
IDCHTAHIAC KFAELKEKID XXSGKKLEDN PKSLKSGDAA IVEMVPGKPM CVESFSQYPP  420
LGXFAVXDMX QTVAVGVIKN VEKKSGGAGK VTKSAQKAQK AGK                    463

SEQ ID NO: 63           moltype = AA  length = 13
FEATURE                 Location/Qualifiers
VARIANT                 1
                        note = lysine or no amino acid
VARIANT                 13
                        note = isoleucine or no amino acid
source                  1..13
                        mol_type = protein
                        organism = synthetic construct
SEQUENCE: 63
XPLRLPLQDV YKX                                                     13

SEQ ID NO: 64           moltype = AA  length = 18
FEATURE                 Location/Qualifiers
VARIANT                 1
                        note = aspartic acid or no amino acid
VARIANT                 18
                        note = threonine or no amino acid
source                  1..18
                        mol_type = protein
                        organism = synthetic construct
SEQUENCE: 64
XVYKIGGIGT VPVGRVEX                                                18
```

```
SEQ ID NO: 65            moltype = AA   length = 421
FEATURE                  Location/Qualifiers
source                   1..421
                         mol_type = protein
                         organism = Homo sapiens
SEQUENCE: 65
MNRGFSRKSH TFLPKIFFRK MSSSGAKDKP ELQFPFLQDE DTVATLLECK TLFILRGLPG   60
SGKSTLARVI VDKYRDGTKM VSADAYKITP GARGAFSEEY KRLDEDLAAY CRRRDIRILV   120
LDDTNHERER LEQLFEMADQ YQYQVVLVEP KTAWRLDCAQ LKEKNQWQLS ADDLKKLKPG   180
LEKDFLPLYF GWFLTKKSSE TLRKAGQVFL EELGNHKAFK KELRQFVPGD EPREKMDLVT   240
YFGKRPPGVL HCTTKFCDYG KAPGAEEYAQ QDVLKKSYSK AFTLTISALF VTPKTTGARV   300
ELSEQQLQLW PSDVDKLSPT DNLPRGSRAH ITLGCAADVE AVQTGLDLLE ILRQEKGGSR   360
GEEVGELSRG KLYSLGNGRW MLTLAKNMEV RAIFTGYYGK GKPVPTQGSR KGGALQSCTI   420
I                                                                   421

SEQ ID NO: 66            moltype = AA   length = 1669
FEATURE                  Location/Qualifiers
source                   1..1669
                         mol_type = protein
                         organism = Homo sapiens
SEQUENCE: 66
MGPRLSVWLL LLPAALLLHE EHSRAAAKGG CAGSGCGKCD CHGVKGQKGE RGLPGLQGVI   60
GFPGMQGPEG PQGPPGGQKGD TGEPGLPGTK GTRGPPGASG YPGNPGLPGI PGQDGPPGPP   120
GIPGCNGTKG ERGPLGPPGL PGFAGNPGPP GLPGMKGDPG EILGHVPGML LKGERGFPGI   180
PGTPGPPGLP GLQGPVGPPG FTGPPGPPGP PGPPGEKGQM GLSFQGPKGD KGDQGVSGPP   240
GVPGQAQVQE KGDFATKGEK GQKGEPGFQG MPGVGEKGEP GKPGPRGKPG KDGDKGEKGS   300
PGFPGEPGYP GLIGRQGPQG EKGEAGPPGP PGIVIGTGPL GEKGERGYPG TPGPRGEPGP   360
KGFPGLPGQP GPPGLPVPGQ AGAPGFPGER GEKGDRGFPG TSLPGPSGRD GLPGPPGSPG   420
PPGQPGYTNG IVECQPGPPG DQGPPGIPGQ PGFIGEIGEK GQKGESCLIC DIDGYRGPPG   480
PQGPPGEIGF PGQPGAKGDR GLPGRDGVAG VPGPQGTPGL IGQPGAKGEP GEFYFDLRLK   540
GDKGDPGFPG QPGMTGRAGS PGRDGHPGLP GPKGSPGSVG LKGERGPPGG VGFPGSRGDT   600
GPPGPPGYGP AGPIGDKGQA GFPGGPGSPG LPGPKGEPGK IVPLPGPPGA EGLPGSPGFP   660
GPQGDRGFPG TPGRPGLPGE KGAVGQPGIG FPGPPGPKGV DGLPGDMGPP GTPGRPGFNG   720
LPGNPGVQGQ KGEPGVGLPG LKGLPGLPGI PGTPGEKGSI GVPGVPGEHG AIGPPGLQGI   780
RGEPGPPGLP GSVGSPGVPG IGPPGARGPP GGQGPPGLSG PPGIKGEKGF PGFPGLDMPG   840
PKGDKGAQGL PGITGQSGLP GLPGQQGAPG IPGFPGSKGE MGVMGTPGQP GSPGPVGAPG   900
LPGEKGDHGF PGSSGPRGDP GLKGDKGDVG LPGKPGSMDK VDMGSMKGQK GDQGEKGQIG   960
PIGEKGSRGD PGTPGVPGKD GQAGQPGQPG PKGDPGISGT PGAPGLPGPK GSVGGMGLPG   1020
TPGEKGVPGI PGPQGSPGLP GDKGAKGEKG QAGPPGIGIP GLRGEKGDQG IAGFPGSPGE   1080
KGEKGSIGIP GMPGSPGLKG SPGSVGYPGS PGLPGEKGDK GLPGLDGIPG VKGEAGLPGT   1140
PGPTGPAGQK GEPGSDGIPG SAGEKGEPGL PGRGFPGFPG AKGDKGSKGE VGFPGLAGSP   1200
GIPGSKGEQG FMGPPGPQGQ PGLPGSPGHA TEGPKGDRGP QGQPGLPGLP GPMGPPGLPG   1260
IDGVKGDKGN PGWPGAPGVP GPKGDPGFQG MPGIGGSPGI TGSKGDMGPP GVPGFQGPKG   1320
LPGLQGIKGD QGDQGVPGAK GLPGPPGPPG PYDIIKGEPG LPGPEGPPGL KGLQGLPGPK   1380
GQQGVTGLVG IPGPPGIPGF DGAPGQKGEM GPAGPTGPRG FPGPPGPDGL PGSMGPPGTP   1440
SVDHGFLVTR HSQTIDDPQC PSGTKILYHG YSLLYVQGNE RAHGQDLGTA GSCLRKFSTM   1500
PFLFCNINNV CNFASRNDYS YWLSTPEPMP MSMAPITGEN IRPFISRCAV CEAPAMVMAV   1560
HSQTIQIPPC PSGWSSLWIG YSFVMHTSAG AEGSGQALAS PGSCLEEFRS APFIECHGRG   1620
TCNYYANAYS FWLATIERSE MFKKPTPSTL KAGELRTHVS RCQVCMRRT             1669

SEQ ID NO: 67            moltype = AA   length = 17
FEATURE                  Location/Qualifiers
VARIANT                  1
                         note = lysine or no amino acid
VARIANT                  17
                         note = phenylalanine or no amino acid
source                   1..17
                         mol_type = protein
                         organism = synthetic construct
SEQUENCE: 67
XAISSPTVSR LTDTTKX                                                   17

SEQ ID NO: 68            moltype = AA   length = 331
FEATURE                  Location/Qualifiers
source                   1..331
                         mol_type = protein
                         organism = Homo sapiens
SEQUENCE: 68
MTAKMETTFY DDALNASFLP SESGPYGYSN PKILKQSMTL NLADPVGSLK PHLRAKNSDL   60
LTSPDVGLLK LASPELERLI IQSSNGHITT TPTPTQFLCP KNVTDEQEGF AEGFVRALAE   120
LHSQNTLPSV TSAAQPVNGA GMVAPAVASV AGGSGSGGFS ASLHSEPPVY ANLSNFNPGA   180
LSSGGGGAPSY GAAGLAFPAQ PQQQQQPPHH LPQQMPVQHP RLQALKEEPQ TVPEMPGETP   240
PLSPIDMESQ ERIKAERKRM RNRIAASKCR KRKLERIARL EEKVKTLKAQ NSELASTANM   300
LREQVAQLKQ KVMNHVNSGC QLMLTQQLQT F                                   331

SEQ ID NO: 69            moltype = AA   length = 21
FEATURE                  Location/Qualifiers
VARIANT                  1
                         note = lysine or no amino acid
```

```
SITE                       8
                           note = Citrulline
VARIANT                    21
                           note = glutamic acid or no amino acid
source                     1..21
                           mol_type = protein
                           organism = synthetic construct
SEQUENCE: 69
XTGGAVDXLT DTSRYTGSHK X                                                     21

SEQ ID NO: 70              moltype = AA  length = 21
FEATURE                    Location/Qualifiers
VARIANT                    1
                           note = lysine or no amino acid
VARIANT                    21
                           note = glutamic acid or no amino acid
source                     1..21
                           mol_type = protein
                           organism = synthetic construct
SEQUENCE: 70
XTGGAVDRLT DTSRYTGSHK X                                                     21

SEQ ID NO: 71              moltype = AA  length = 21
FEATURE                    Location/Qualifiers
VARIANT                    1
                           note = lysine or no amino acid
VARIANT                    21
                           note = asparagine or no amino acid
source                     1..21
                           mol_type = protein
                           organism = synthetic construct
SEQUENCE: 71
XGIAGRQDIL DDSGYVSAYK X                                                     21

SEQ ID NO: 72              moltype = AA  length = 195
FEATURE                    Location/Qualifiers
source                     1..195
                           mol_type = protein
                           organism = Homo sapiens
SEQUENCE: 72
MSSCSNVCGS RQAQAAAEGG YQRYGVRSYL HQFYEDCTAS IWEYEDDFQI QRSPNRWSSV       60
FWKVGLISGT VFVILGLTVL AVGFLVPPKI EAFGEADFVV VDTHAVQFNS ALDMYKLAGA       120
VLFCIGGTSM AGCLLMSVFV KSYSKEEKFL QQKFKERIAD IKAHTQPVTK APGPGETKIP       180
VTLSRVQNVQ PLLAT                                                        195

SEQ ID NO: 73              moltype = AA  length = 371
FEATURE                    Location/Qualifiers
source                     1..371
                           mol_type = protein
                           organism = Homo sapiens
SEQUENCE: 73
MAELQEVQIT EEKPLLPGQT PEAAKEAELA ARILLDQGQT HSVETPYGSV TFTVYGTPKP       60
KRPAILTYHD VGLNYKSCFQ PLFQFEDMQE IIQNFVRVHV DAPGMEEGAP VFPLGYQYPS       120
LDQLADMIPC VLQYLNFSTI IGVGVGAGAY ILARYALNHP DTVEGLVLIN IDPNAKGWMD       180
WAAHKLTGLT SSIPEMILGH LFSQEELSGN SELIQKYRNI ITHAPNLDNI ELYWNSYNNR       240
RDLNFERGGD ITLRCPVMLV VGDQAPHEDA VVECNSKLDP TQTSFLKMAD SGGQPQLTQP       300
GKLTEAFKYF LQGMGYMASS CMTRLSRSRT ASLTSAASVD GNRSRSRTLS QSSESGTLSS       360
GPPGHTMEVS C                                                            371

SEQ ID NO: 74              moltype = AA  length = 18
FEATURE                    Location/Qualifiers
VARIANT                    1
                           note = arginine or no amino acid
VARIANT                    18
                           note = serine or no amino acid
source                     1..18
                           mol_type = protein
                           organism = synthetic construct
SEQUENCE: 74
XTASLTSAAS VDGNRSRX                                                         18

SEQ ID NO: 75              moltype = AA  length = 92
FEATURE                    Location/Qualifiers
source                     1..92
                           mol_type = protein
                           organism = Homo sapiens
SEQUENCE: 75
MSELEKAMVA LIDVFHQYSG REGDKHKLKK SELKELINNE LSHFLEEIKE QEVVDKVMET       60
LDNDGDGECD FQEFMAFVAM VTTACHEFFE HE                                    92
```

-continued

```
SEQ ID NO: 76              moltype = AA  length = 434
FEATURE                    Location/Qualifiers
source                     1..434
                           mol_type = protein
                           organism = Homo sapiens
SEQUENCE: 76
MSIEKIWARE ILDSRGNPTV EVDLYTAKGL FRAAVPSGAS TGIYEALELR DGDKQRYLGK  60
GVLKAVDHIN STIAPALISS GLSVVEQEKL DNLMLELDGT ENKSKFGANA ILGVSLAVCK  120
AGAAERELPL YRHIAQLAGN SDLILPVPAF NVINGGSHAG NKLAMQEFMI LPVGAESFRD  180
AMRLGAEVYH TLKGVIKDKY GKDATNVGDE GGFAPNILEN SEALELVKEA IDKAGYTEKI  240
VIGMDVAASE FYRDGKYDLD FKSPTDPSRY ITGDQLGALY QDFVRDYPVV SIEDPFDQDD  300
WAAWSKFTAN VGIQIVGDDL TVTNPKRIER AVEEKACNCL LLKVNQIGSV TEAIQACKLA  360
QENGWGVMVS HRSGETEDTF IADLVVGLCT GQIKTGAPCR SERLAKYNQL MRIEEELGDE  420
ARFAGHNFRN PSVL                                                    434

SEQ ID NO: 77              moltype = AA  length = 76
FEATURE                    Location/Qualifiers
source                     1..76
                           mol_type = protein
                           organism = Homo sapiens
SEQUENCE: 77
QPDAINAPVT CCYNFTNRKI SVQRLASYRR ITSSKCPKEA VIFKTIVAKE ICADPKQKWV  60
QDSMDHLDKQ TQTPKT                                                  76

SEQ ID NO: 78              moltype = AA  length = 758
FEATURE                    Location/Qualifiers
source                     1..758
                           mol_type = protein
                           organism = Homo sapiens
SEQUENCE: 78
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQEPESGK VVQEGFLREP GPPGLSHQLM SGMPGAPLLP GEPREATRQP SGTGPEDTEG  180
GRHAPELLKH QLLGDLHQEG PPLKGAGGKE RPGSKEEVDE DRDVDESSPQ DSPPSKASPA  240
QDGRPPQTAA REATSIPGFP AEGAIPLPVD FLSKVSTEIP ASEPDGPSVG RAKGQDAPLE  300
FTFHVEITPN VQKEQAHSEE HLGRAAFPGA PGEGPEARGP SLGEDTKEAD LPEPSEKQPA  360
AAPRGKPVSR VPQLKARMVS KSKDGTGSDD KKAKTSTRSS AKTLKNRPCL SPKHPTPGSS  420
DPLIQPSSPA VCPEPPSSPK YVSSVTSRTG SSGAKEMKLK GADGKTKIAT PRGAAPPGQK  480
GQANATRIPA KTPPAPKTPP SSGEPPKSGD RSGYSSPGSP GTPGSRSRTP SLPTPPTREP  540
KKVAVVRTPP KSPSSAKSRL QTAPVPMPDL KNVKSKIGST ENLKHQPGGG KVQIINKKLD  600
LSNVQSKCGS KDNIKHVPGG GSVQIVYKPV DLSKVTSKCG SLGNIHHKPG GGQVEVKSEK  660
LDFKDRVQSK IGSLDNITHV PGGGNKKIET HKLTFRENAK AKTDHGAEIV YKSPVVSGDT  720
SPRHLSNVSS TGSIDMVDSP QLATLADEVS ASLAKQGL                          758

SEQ ID NO: 79              moltype = AA  length = 543
FEATURE                    Location/Qualifiers
source                     1..543
                           mol_type = protein
                           organism = Homo sapiens
SEQUENCE: 79
MSSFSYEPYY STSYKRRYVE TPRVHISSVR SGYSTARSAY SSYSAPVSSS LSVRRSYSSS  60
SGSLMPSLEN LDLSQVAAIS NDLKSIRTQE KAQLQDLNDR FASFIERVHE LEQQNKVLEA  120
ELLVLRQKHS EPSRFRALYE QEIRDLRLAA EDATNEKQAL QGEREGLEET LRNLQARYEE  180
EVLSREDAEG RLMEARKGAD EAALARAELE KRIDSLMDEI SFLKKVHEEE IAELQAQIQY  240
AQISVEMDVT KPDLSAALKD IRAQYEKLAA KNMQNAEEWF KSRFTVLTES AAKNTDAVRA  300
AKDEVSESRR LLKAKTLEIE ACRGMNEALE KQLQELEDKQ NADISAMQDT INKLENELRT  360
TKSEMARYLK EYQDLLNVKM ALDIEIAAYR KLLEGEETRL SFTSVGSITS GYSQSSQVFG  420
RSAYGGLQTS SYLMSTRSFP SYYTSHVQEE QIEVEETIEA AKAEEEAKDEP PSEGEAEEEE  480
KDKEEAEEEE AAEEEEAAKE ESEEAKEEEE GGEGEEGEET KEAEEEEKKV EGAGEEQAAK  540
KKD                                                                543

SEQ ID NO: 80              moltype = AA  length = 1026
FEATURE                    Location/Qualifiers
source                     1..1026
                           mol_type = protein
                           organism = Homo sapiens
SEQUENCE: 80
MMSFGGADAL LGAPFAPLHG GGSLHYALAR KGGAGGTRSA AGSSSGFHSW TRTSVSSVSA  60
SPSRFRGAGA ASSTDSLDTL SNGPEGCMVA VATSRSEKEQ LQALNDRFAG YIDKVRQLEA  120
HNRSLEGEAA ALRQQQAGRS AMGELYEREV REMRGAVLRL GAARGQLRLE QEHLLEDIAH  180
VRQRLDDEAR QREEAEAAAR ALARFAQEAE AARVDLQKKA QALQEECGYL RRHHQEEVGE  240
LLGQIQGSGA AQAQMQAETR DALKCDVTSA LREIRAQLEG HAVQSTLQSE EWFRVRLDRL  300
SEAAKVNTDA MRSAQEEITE YRRQLQARTT ELEALKSTKD SLERQRSELE DRHQADIASY  360
QEAIQQLDAE LRNTKWEMAA QLREYQDLLN VKMALDIEIA AYRKLLEGEE CRIGFGPIPF  420
SLPEGLPKIP SVSTHIKVKS EEKIKVVEKS EKETVIVEEQ TEETQVTEEV TEEEEKEAKE  480
EEGKEEEGGE EEEAEGGEEE TKSPPAEEAA SPEKEAKSPV KEEAKSPAEA KSPEKEEAKS  540
PAEVKSPEKA KSPAKEEAKS PPEAKSPEKE EAKSPAEVKS PEKAKSPAKE EAKSPAEAKS  600
PEKAKSPVKE EAKSPAEAKS PVKEEAKSPA EVKSPEKAKS PTKEEAKSPE KAKSPEKAKS  660
```

-continued

```
PEKEEAKSPE KAKSPVKAEA KSPEKAKSPV KAEAKSPEKA KSPVKEEAKS PEKAKSPVKE   720
EAKSPEKAKS PVKEEAKTPE KAKSPVKEEA KSPEKAKSPE KAKTLDVKSP EAKTPAKEEA   780
RSPADKFPEK AKSPVKEEVK SPEKAKSPLK EDAKAPEKEI PKKEEVKSPV KEEEKPQEVK   840
VKEPPKKAEE EKAPATPKTE EKKDSKKEEA PKKEAPKPKV EEKKEPAVEK PKESKVEAKK   900
EEAEDKKKVP TPEKEAPAKV EVKEDAKPKE KTEVAKKEPD DAKAKEPSKP AEKKEAAPEK   960
KDTKEEKAKK PEEKPKTEAK AKEDDKTLSK EPSKPKAEKA EKSSSTDQKD SKPPEKATED  1020
KAAKGK                                                             1026

SEQ ID NO: 81          moltype = AA  length = 434
FEATURE                Location/Qualifiers
source                 1..434
                       mol_type = protein
                       organism = Homo sapiens
SEQUENCE: 81
MSIEKIWARE ILDSRGNPTV EVDLYTAKGL FRAAVPSGAS TGIYEALELR DGDKQRYLGK   60
GVLKAVDHIN STIAPALISS GLSVVEQEKL DNLMLELDGT ENKSKFGANA ILGVSLAVCK  120
AGAAERELPL YRHIAQLAGN SDLILPVPAF NVINGGSHAG NKLAMQEFMI LPVGAESFRD  180
AMRLGAEVYH TLKGVIKDKY GKDATNVGDE GGFAPNILEN SEALELVKEA IDKAGYTEKI  240
VIGMDVAASE FYRDGKYDLD FKSPTDPSRY ITGDQLGALY QDFVRDYPVV SIEDPFDQDD  300
WAAWSKFTAN VGIQIVGDDL TVTNPKRIER AVEEKACNCL LLKVNQIGSV TEAIQACKLA  360
QENGWGVMVS HRSGETEDTF IADLVVGLCT GQIKTGAPCR SERLAKYNQL MRIEEELGDE  420
ARFAGHNFRN PSVL                                                    434

SEQ ID NO: 82          moltype = AA  length = 622
FEATURE                Location/Qualifiers
source                 1..622
                       mol_type = protein
                       organism = Homo sapiens
SEQUENCE: 82
MAHVRGLQLP GCLALAALCS LVHSQHVFLA PQQARSLLQR VRRANTFLEE VRKGNLEREC   60
VEETCSYEEA FEALESSTAT DVFWAKYTAC ETARTPRDKL AACLEGNCAE GLGTNYRGHV  120
NITRSGIECQ LWRSRYPHKP EINSTTHPGA DLQENFCRNP DSSTTGPWCY TTDPTVRRQE  180
CSIPVCGQDQ VTVAMTPRSE GSSVNLSPPL EQCVPDRGQQ YQGRLAVTTH GLPCLAWASA  240
QAKALSKHQD FNSAVQLVEN FCRNPDGDEE GVWCYVAGKP GDFGYCDLNY CEEAVEEETG  300
DGLDEDSDRA IEGRTATSEY QTFFNPRTFG SGEADCGLRP LFEKKSLEDK TERELLESYI  360
DGRIVEGSDA EIGMSPWQVM LFRKSPQELL CGASLISDRW VLTAAHCLLY PPWDKNFTEN  420
DLLVRIGKHS RTRYERNIEK ISMLEKIYIH PRYNWRENLD RDIALMKLKK PVAFSDYIHP  480
VCLPDRETAA SLLQAGYKGR VTGWGNLKET WTANVGKGQP SVLQVVNLPI VERPVCKDST  540
RIRITDNMFC AGYKPDEGKR GDACEGDSGG PFVMKSPFNN RWYQMGIVSW GEGCDRDGKY  600
GFYTHVFRLK KWIQKVIDQF GE                                           622

SEQ ID NO: 83          moltype = AA  length = 885
FEATURE                Location/Qualifiers
source                 1..885
                       mol_type = protein
                       organism = Homo sapiens
SEQUENCE: 83
MAPPSTREPR VLSATSATKS DGEMVLPGFP DADSFVKFAL GSVVAVTKAS GGLPQFGDEY   60
DFYRSFPGFQ AFCETQGDRL LQCMSRVMQY HGCRSNIKDR SKVTELEDKF DLLVDANDVI  120
LERVGILLDE ASGVNKNQQP VLPAGLQVPK TVVSSWNRKA AEYGKKAKSE TFRLLHAKNI  180
IRPQLKFREK IDNSNTPFLP KIFIKPNAQK PLPQALSKER RERPQDRPED LDVPPALADF  240
IHQQRTQQVE QDMFAHPYQY ELNHFTPADA VLQKPQPQLY RPIEETPCHF ISSLDELVEL  300
NEKLLNCQEF AVDLEHHSYR SFLGLTCLMQ ISTRTEDFII DTLELRSDMY ILNESLTDPA  360
IVKVFHGADS DIEWLQKDFG LYVVNMFDTH QAARLLNLGR HSLDHLLKLY CNVDSNKQYQ  420
LADWRIRPLP EEMLSYARDD THYLLYIYDK MRLEMWERGN GDPVQLQVVW QRSRDICLKK  480
FIKPIFTDES YLELYRKQKK HLNTQQLTAF QLLFAWRDKT ARREDESYGY VLPNHMMLKI  540
AEELPKEPQG IIACCNPVPP LVRQQINEMH LLIQQAREMP LLKSEVAAGV KKSGPLPSAE  600
RLENVLFGPH DCSHAPPDGY PIIPTSGSVP VQKQASLFPD EKEDNLLGTT CLIATAVITL  660
FNEPSAEDSK KGPLTVAQKK AQNIMESFEN PFRMFLPSLG HRAPVSQAAK FDPSTKIYEI  720
SNRWKLAQVQ VQKDSKEAVK KKAAEQTAAR EQAKEACKAA AEQAISVRQQ VVLENAAKKR  780
ERATSDPRTT EQKQEKKRLK ISKKPKDPEP PEKEFTPYDY SQSDFKAFAG NSKSKVSSQF  840
DPNKQTPSGK KCIAAKKIKQ SVGNKSMSFP TGKSDRGFRY NWPQR                  885

SEQ ID NO: 84          moltype = AA  length = 2419
FEATURE                Location/Qualifiers
source                 1..2419
                       mol_type = protein
                       organism = Homo sapiens
SEQUENCE: 84
MEQFPKETVV ESSGPKVLET AEEIQERRQE VLTRYQSFKE RVAERGQKLE DSYHLQVFKR   60
DADDLGKWIM EKVNILTDKS YEDPTNIQGK YQKHQSLEAE VQTKSRLMSE LEKTREERFT  120
MGHSAHEETK AHIEELRHLW DLLLELTLEK GDQLLRALKF QQYVQECADI LEWIGDKEAI  180
ATSVELGEDW ERTEVLHKKF EDFQVELVAK EGRVVEVNQY ANECAEENHP DLPLIQSKQN  240
EVNAAWERLR GLALQRQKAL SNAANLQRFK RDVTEAIQWI KEKEPVLTSE DYGKDLVASE  300
GLFHSHKGLE RNLAVMSDKV KELCAKAEKL TLSHPSDAPQ IQEMKEDLVS SWEHIRALAT  360
SRYEKLQATY WYHRFSSDFD ELSGWMNEKT AAINADELPT DVAGGEVLLD RHQQHKHEID  420
SYDDRFQSAD ETGQDLVNAN HEASDEVREK MEILDNNWTA LLELWDERHR QYEQCLDFHL  480
FYRDSEQVDS WMSRQEAFLE NEDLGNSLGS AEALLQKHED FEEAFTAQEE KIITVDKTAT  540
KLIGDDHYDS ENIKAIRDGL LARRDALREK AATRRRLLKE SLLLQKLYED SDDLKNWINK  600
```

```
KKKLADDEDY KDIQNLKSRV QKQQVFEKEL AVNKTQLENI QKTGQEMIEG GHYASDNVTT   660
RLSEVASLWE ELLEATKQKG TQLHEANQQL QFENNAEDLQ RWLEDVEWQV TSEDYGKGLA   720
EVQNRLRKHG LLESAVAARQ DQVDILTDLA AYFEEIGHPD SKDIRARQES LVCRFEALKE   780
PLATRKKKLL DLLHLQLICR DTEDEEAWIQ ETEPSATSTY LGKDLIASKK LLNRHRVILE   840
NIASHEPRIQ EITERGNKMV EEGHFAAEDV ASRVKSLNQN MESLRARAAR RQNDLEANVQ   900
FQQYLADLHE AETWIREKEP IVDNTNYGAD EEAAGALLKK HEAFLLDLNS FGDSMKALRN   960
QANACQQQQA APVEGVAGEQ RVMALYDFQA RSPREVTMKK GDVLTLLSSI NKDWWKVEAA  1020
DHQGIVPAVY VRRLAHDEFP MLPQRRREEP GNITQRQEQI ENQYRSLLDR AEEERRRLLQ  1080
RYNEFLLAYE AGDMLEWIQE KKAENTGVEL DDVWELQKKF DEFQKDLNTN EPRLRDINKV  1140
ADDLLFEGLL TPEGAQIRQE LNSRWGSLQR LADEQRQLLG SAHAVEVFHR EADDTKEQIE  1200
KKCQALSAAD PGSDLFSVQA LQRRHEGFER DLVPLGDKVT ILGETAERLS ESHPDATEDL  1260
QRQKMELNEA WEDLQGRTKD RKESLNEAQK FYLFLSKARD LQNWISSIGG MVSSQELAED  1320
LTGIEILLER HQEHRADMEA EAPTFQALED FSAELIDSGH HASPEIEKKL QAVKLERDDL  1380
EKAWEKRKKI LDQCLELQMF QGNCDQVESW MVARENSLRS DDKSSLDSLE ALMKKRDDLD  1440
KAITAQEGKI TDLEHFAESL IADEHYAKEE IATRLQRVLD RWKALKAQLI DERTKLGDYA  1500
NLKQFYRDLE ELEEWISEML PTACDESYKD ATNIQRKYLK HQTFAHEVDG RSEQVHGVIN  1560
LGNSLIECSA CDGNEEAMKE QLEQLKEHWD HLLERTNDKG KKLNEASRQQ RFNTSIRDFE  1620
FWLSEAETLL AMKDQARDLA SAGNLLKKHQ LLEREMLARE DALKDLNTLA EDLLSSGTFN  1680
VDQIVKKKDN VNKRFLNVQE LAAAHHEKLK EAYALFQFFQ DLDDEESWIE EKLIRVSSQD  1740
YGRDLQGVQN LLKKHKRLEG ELVAHEPAIQ NVLDMAEKLK DKAAVGQEEI QLRLAQFVEH  1800
WEKLKELAKA RGLKLEESLE YLQFMQNAEE EEAWINEKNA LAVRGDCGDT LAATQSLLMK  1860
HEALENDFAV HETRVQNVCA QGEDILNKVL QEESQNKEIS SKIEALNEKT PSLAKAIAAW  1920
KLQLEDDYAF QEFNWKADVV EAWIADKETS LKTNGNGADL GDFLTLLAKQ DTLDASLQSF  1980
QQERLPEITD LKDKLISAQH NQSKAIEERY AALLKRWEQL LEASAVHRQK LLEKQLPLQK  2040
AEDLFVEFAH KASALNNWCE KMEENLSEPV HCVSLNEIRQ LQKDHEDFLA SLARAQADFK  2100
CLLELDQQIK ALGVPSSPYT WLTVEVLERT WKHLSDIIEE REQELQKEEA RQVKNFEMCQ  2160
EFEQNASTFL QWILETRAYF LDGSLLKETG TLESQLEANK RKQKEIQAMK RQLTKIVDLG  2220
DNLEDALILD IKYSTIGLAQ QWDQLYQLGL RMQHNLEQQI QAKDIKGVSE ETLKEFSTIY  2280
KHFDENLTGR LTHKEFRSCL RGLNYYLPMV EEDEHEPKFE KFLDAVDPGR KGYVSLEDYT  2340
AFLIDKESEN IKSSDEIENA FQALAEGKSY ITKEDMKQAL TPEQVSFCAT HMQQYMDPRG  2400
RSHLSGYDYV GFTNSYFGN                                                2419

SEQ ID NO: 85          moltype = AA  length = 745
FEATURE                Location/Qualifiers
source                 1..745
                       mol_type = protein
                       organism = Homo sapiens
SEQUENCE: 85
MGVPFFSSLR CMVDLGPCWA GGLTAEMKLL LALAGLLAIL ATPQPSEGAA PAVLGEVDTS   60
LVLSSMEEAK QLVDKAYKER RESIKQRLRS GSASPMELLS YFKQPVAATR TAVRAADYLH  120
VALDLLERKL RSLWRRPFNV TDVLTPAQLN VLSKSSGCAY QDVGVTCPEQ DKYRTITGMC  180
NNRRSPTLGA SNRAFVRWLP AEYEDGFSLP YGWTPGVKRN GFPVALARAV SNEIVRFPTD  240
QLTPDQERSL MFMQWGQLLD HDLDFTPEPA ARASFVTGVN CETSCVQQPP CFPLKIPPND  300
PRIKNQADCI PFFRSCPACP GSNITIRNQI NALTSFVDAS MVYGSEEPLA RNLRNMSNQL  360
GLLAVNQRFQ DNGRALLPFD NLHDDPCLLT NRSARIPCFL AGDTRSSEMP ELTSMHTLLL  420
REHNRLATEL KSLNPRWDGE RLYQEARKIV GAMVQIITYR DYLPLVLGPT AMRKYLPTYR  480
SYNDSVDPRI ANVFTNAFRY GHTLIQPFMF RLDNRYQPME PNPRVPLSRV FFASWRVVLE  540
GGIDPILRGL MATPAKLNRQ NQIAVDEIRE RLFEQVMRIG LDLPALNMQR SRDHGLPGYN  600
AWRRFCGLPQ PETVGQLGTV LRNLKLARKL MEQYGTPNNI DIWMGGVSEP LKRKGRVGPL  660
LACIIGTQFR KLRDGDRFWW ENEGVFSMQQ RQALAQISLP RIICDNTGIT TVSKNNIFMS  720
NSYPRDFVNC STLPALNLAS WREAS                                          745

SEQ ID NO: 86          moltype = AA  length = 1048
FEATURE                Location/Qualifiers
source                 1..1048
                       mol_type = protein
                       organism = Homo sapiens
SEQUENCE: 86
MSLQFIGLQR RDVVALVNFL RHLTQKPDVD LEAHPKILKK CGEKRLHRRT VLFNELMLWL   60
GYYRELRFHN PDLSSVLEEF EVRCVAVARR GYTYPFGDRG KARDHLAVLD RTEFDTDVRH  120
DAEIVERALV SAVILAKMSV RETLVTAIGQ TEPIAFVHLK DTEVQRIEEN LEGVRRNMFC  180
VKPLDLNLDR HANTALVNAV NKLVYTGRLI MNVRRSWEEL ERKCLARIQE RCKLLVKELR  240
MCLSFDSNYC RNILKHAVEN GDSADTLLEL LIEDFDIYVD SFPQSAHTFL GARSPSLEFD  300
DDANLLSLGG GSAFSSVPKK HVPTQPLDGW SWIASPWKGH KPFRFEAHGS LAPAAEAHAA  360
RSAAVGYYDE EEKRRERQKR VDDEVVQREK QQLKAWEERQ QNLQQRQQQP PPPARKPSAS  420
RRLFGSSADE DDDDDDDEKN IFTPIKKPGT SGKGAASGGG VSSIFSGLLS SGSQKPTSGP  480
LNIPQQQQRH AAFSLVSPQV TKASPGRVRR DSAWDVRPLT ETRGDLFSGD EDSDSSDGYP  540
PNRQDPRFTD TLVDITDTET SAKPPVTTAY KFEQPTLTFG AGVNVPAGAG AAILTPTPVN  600
PSTAPAPAPT PTFAGTQTPV NGNSPWAPTA PLPGDMNPAN WPRERAWALK NPHLAYNPFR  660
MPTTSTASQN TVSTTPRRPS TPRAAVTQTA SRDAADEVWA LRDQTAESPV EDSEEEDDDS  720
SDTGSVVSLG HTTPSSDYNN DVISPPSQTP EQSTPSRIRK AKLSSPMTTT STSQKPVLGK  780
RVATPHASAR AQTVTSTPVQ GRLEKQVSGT PSTVPATLLQ PQPASSKTTS SRNVTSGAGT  840
SSASSARQPS ASASVLSPTE DDVVSPATSP LSMLSSASPS PAKSAPPSPV KGRGSRVGVP  900
SLKPTLGGKA VVGRPPSVPV SGSAPGRLSG SSRAASTTPT YPAVTTVYPP SSTAKSSVSN  960
APPVASPSIL KPGASAALQS RRSTGTAAVG SPVKSTTGMK TVAFDLSSPQ KSGTGPQPGS 1020
AGMGGAKTPS DAVQNILQKI EKIKNTEE                                     1048

SEQ ID NO: 87          moltype = AA  length = 812
FEATURE                Location/Qualifiers
```

```
source                    1..812
                          mol_type = protein
                          organism = Homo sapiens
SEQUENCE: 87
LFPLAERPDR VELMPLPPWQ PVGENFTLSC RVPGAGPRAS LTLTLLRGAQ ELIRRSFAGE   60
PPRARGAVLT ATVLARREDH GANFSCRAEL DLRPHGLGLF ENSSAPRELR TFSLSPDAPR  120
LAAPRLLEVG SERPVSCTLD GLFPASEARV YLALGDQNLS PDVTLEGDAF VATATATASA  180
EQEGARQLIC NVTLGGENRE TRENVTIYSF PAPLLTLSEP SVSEGQMVTV TCAAGTQALV  240
TLEGVPAAVP GQPAQLQLNA TENDDRRSFF CDATLDVDGE TLIKNRSAEL RVLYAPRLDD  300
SDCPRSWTWP EGPEQTLRCE ARGNPEPSVH CARSDGGAVL ALGLLGPVTR ALSGTYRCKA  360
ANDQGEAVKD VTLTVEYAPA LDSVGCPERI TWLEGTEASL SCVAHGVPPP DVICVRSGEL  420
GAVIEGLLRV AREHAGTYRC EATNPRGSAA KNVAVTVEYG PRFEEPSCPS NWTWVEGSGR  480
LFSCEVDGKP QPSVKCVGSG GATEGVLLPL APPDPSPRAP RIPRVLAPGI YVCNATNRHG  540
SVAKTVVVSA ESPPEMDEST CPSHQTWLEG AEASALACAA RGRPSPGVRC SREGIPWPEQ  600
QRVSREDAGT YHCVATNAHG TDSRTVTVGV EYRPVVAELA ASPPGGVRPG GNFTLTCRAE  660
AWPPAQISWR APPGALNIGL SSNNSTLSVA GAMGSHGGEY ECAATNAHGR HARRITVRVA  720
GPWLWVAVGG AAGGAALLAA GAGLAFYVQS TACKKGEYNV QEAESSGEAV CLNGAGGGAG  780
GAAGAEGGPE AAGGAAESPA EGEVFAIQLT SA                                812

SEQ ID NO: 88             moltype = AA   length = 342
FEATURE                   Location/Qualifiers
source                    1..342
                          mol_type = protein
                          organism = Homo sapiens
SEQUENCE: 88
MLQGHSSVFQ ALLGTFFTWG MTAAGAALVF VFSSGQRRIL DGSLGFAAGV MLAASYWSLL   60
APAVEMATSS GGFGAFAFFP VAVGFTLGAA FVYLADLLMP HLGAAEDPQT TLALNFGSTL  120
MKKKSDPEGP ALLFPESELS IRIGRAGLLS DKSENGEAYQ RKKAAATGLP EGPAVPVPSR  180
GNLAQPGGSS WRRIALLILA ITIHNVPEGL AVGVGFGAIE KTASATFESA RNLAIGIGIQ  240
NFPEGLAVSL PLRGAGFSTW RAFWYGQLSG MVEPLAGVFG AFAVVLAEPI LPYALAFAAG  300
AMVYVVMDDI IPEAQISGNG KLASWASILG FVVMMSLDVG LG                     342

SEQ ID NO: 89             moltype = AA   length = 1827
FEATURE                   Location/Qualifiers
source                    1..1827
                          mol_type = protein
                          organism = Homo sapiens
SEQUENCE: 89
MADERKDEAK APHWTSAPLT EASAHSHPPE IKDQGGAGEG LVRSANGFPY REDEEGAFGE   60
HGSQGTYSNT KENGINGELT SADRETAEEV SARIVQVVTA EAVAVLKGEQ EKEAQHKDQT  120
AALPLAAEET ANLPPSPPPS PASEQTVTVE EDLLTASKME FHDQQELTPS TAEPSDQKEK  180
ESEKQSKPGE DLKHAALVSQ PETTKTYPDK KDMQGTEEEK APLALFGHTL VASLEDMKQK  240
TEPSLVVPGI DLPKEPPTPK EQKDWFIEMP TEAKKDEWGL VAPISPGPLT PMREKDVFDD  300
IPKWEGKQFD SPMPSPFQGG SFTLPLDVMK NEIVTETSPF APAFLQPDDK KSLQQTSGPA  360
TAKDSFKIEE PHEAKPDKMA EAPPSEAMTL PKDAHIPVVE EHVMGKVLEE EKEAINQETV  420
QQRDTFTPSG QEPILTEKET ELKLEEKTTI SDKEAVPKES KPPKPADEEI GIIQTSTEHT  480
FSEQKDQEPT TDMLKQDSFP VSLEQAVTDS AMTSKTLEKA MTEPSALIEK SSIQELFEMR  540
VDDKDKIEGV GAATSAELDM PFYEDKSGMS KYFETSALKE EATKSIEPGS DYYELSDTRE  600
SVHESIDTMS PMHKNGDKEF QTGKESQPSP PAQEAGYSTL AQSYPSDLPE EPSSPQERMF  660
TIDPKVYGEK RDLHSKNKDD LTLSRSLGLG GRSAIEQRSM SINLPMSCLD SIALGFNFGR  720
GHDLSPLASD ILTNTSGSMD EGDDYLPATT PALEKAPCFP VESKEEEQIE KVKATGEEST  780
QAEISCESPF LAKDFYKNGT VMAPDLPEML DLAGTRSRLA SVSADAEVAR RKSVPSETVV  840
EDSRTGLPPV TDENHVIVKT DSQLEDLGYC VFNKYTVPLP SPVQDSENLS GESGTFYEGT  900
DDKVRRDLAT DLSLIEVKLA AAGRVKDEFS VDKEASAHIS GDKSGLSKEF DQEKKANDRL  960
DTVLEKSEEH ADSKEHAKKT EEAGDEIETF GLGVTYEQAL AKDLSIPTDA SSEKAEKGLS 1020
SVPEIAEVEP SKKVEQGLDF AVQGQLDVKI SDFGQMASGL NIDDRRATEL KLEATQDMTP 1080
SSKAPQEADA PMGVESGHMK EGTKVSETEV KEKVAKPDLV HQEAVDKEES YESSGEHESL 1140
TMESLKADEG KKETSPESSL IQDEIAVKLS VEIPCPPAVS EADLATDERA DVQMEFIQGP 1200
KEESKETPDI SITPSDVAEP LHETIVSEPA EIQSEEEEIE AQGEYDKLLF RSDTLQITDL 1260
GVSGAREEFV ETCPSEHKGV IESVVTIEDD FITVVQTTTD EGESGSHSVR FAALEQPEVE 1320
RRPSPHDEEE FEVEEAAEAQ AEPKDGSPEA PASPEREEVA LSEYKTETYD DYKDETTIDD 1380
SIMDADSLWV DTQDDDRSIM TEQLETIPKE EKAEKEARRS SLEKHRKEKP FKTGRGRIST 1440
PERKVAKKEP STVSRDEVRR KKAVYKKAEL AKKTEVQAHS PSRKFILKPA IKYTRPTHLS 1500
CVKRKTTAAG GESALAPSVF KQAKDKVSDG VTKSPEKRSS LPRPSSILPP RRGVSGDRDE 1560
NSFSLNSSIS SSARRTTRSE PIRRAGKSGT STPTTPGSTA ITPGTPPSYS SRTPGTPGTP 1620
SYPRTPHTPG TPKSAILVPS EKKVAIIRTP PKSPATPKQL RLINQPLPDL KNVKSKIGST 1680
DNIKYQPKGG QVQIVTKKID LSHVTSKCGS LKNIRHRPGG GRVKIESVKL DFKEKAQAKV 1740
GSLDNAHHVP GGGNVKIDSQ KLNFREHAKA RVDHGAEIIT QSPGRSSVAS PRRLSNVSSS 1800
GSINLLESPQ LATLAEDVTA ALAKQGL                                     1827

SEQ ID NO: 90             moltype = AA   length = 758
FEATURE                   Location/Qualifiers
source                    1..758
                          mol_type = protein
                          organism = Homo sapiens
SEQUENCE: 90
MAEPRQEFEV MEDHAGTYGL GDRKDQGGYT MHQDQEGDTD AGLKESPLQT PTEDGSEEPG   60
SETSDAKSTP TAEDVTAPLV DEGAPGKQAA AQPHTEIPEG TTAEEAGIGD TPSLEDEAAG  120
HVTQEPESGK VVQEGFLREP GPPGLSHQLM SGMPGAPLLP EGPREATRQP SGTGPEDTEG  180
```

```
GRHAPELLKH QLLGDLHQEG PPLKGAGGKE RPGSKEEVDE DRDVDESSPQ DSPPSKASPA   240
QDGRPPQTAA REATSIPGFP AEGAIPLPVD FLSKVSTEIP ASEPDGPSVG RAKGQDAPLE   300
FTFHVEITPN VQKEQAHSEE HLGRAAFPGA PGEGPEARGP SLGEDTKEAD LPEPSEKQPA   360
AAPRGKPVSR VPQLKARMVS KSKDGTGSDD KKAKTSTRSS AKTLKNRPCL SPKHPTPGSS   420
DPLIQPSSPA VCPEPPSSPK YVSSVTSRTG SSGAKEMKLK GADGKTKIAT PRGAAPPGQK   480
GQANATRIPA KTPPAPKTPP SSGEPPKSGD RSGYSSPGSP GTPGSRSRTP SLPTPPPTREP  540
KKVAVVRTPP KSPSSAKSRL QTAPVPMPDL KNVKSKIGST ENLKHQPGGG KVQIINKKLD   600
LSNVQSKCGS KDNIKHVPGG GSVQIVYKPV DLSKVTSKCG SLGNIHHKPG GGQVEVKSEK   660
LDFKDRVQSK IGSLDNITHV PGGGNKKIET HKLTFRENAK AKTDHGAEIV YKSPVVSGDT   720
SPRHLSNVSS TGSIDMVDSP QLATLADEVS ASLAKQGL                          758
```

```
SEQ ID NO: 91          moltype = AA  length = 422
FEATURE                Location/Qualifiers
source                 1..422
                       mol_type = protein
                       organism = Homo sapiens
SEQUENCE: 91
MDVLSPGQGN NTTSPPAPFE TGGNTTGISD VTVSYQVITS LLLGTLIFCA VLGNACVVAA   60
IALERSLQNV ANYLIGSLAV TDLMVSVLVL PMAALYQVLN KWTLGQVTCD LFIALDVLCC   120
TSSILHLCAI ALDRYWAITD PIDYVNKRTP RRAAALISLT WLIGFLISIP PMLGWRTPED   180
RSDPDACTIS KDHGYTIYST FGAFYIPLLL MLVLYGRIFR AARFRIRKTV KKVEKTGADT   240
RHGASPAPQP KKSVNGESGS RNWRLGVESK AGGALCANGA VRQGDDGAAL EVIEVHRVGN   300
SKEHLPLPSE AGPTPCAPAS FERKNERNAE AKRKMALARE RKTVKTLGII MGTFILCWLP   360
FFIVALVLPF CESSCHMPTL LGAIINWLGY SNSLLNPVIY AYFNKDFQNA FKKIIKCKFC   420
RQ                                                                 422
```

```
SEQ ID NO: 92          moltype = AA  length = 1894
FEATURE                Location/Qualifiers
source                 1..1894
                       mol_type = protein
                       organism = Homo sapiens
SEQUENCE: 92
MKAMPWNWTC LLSHLLMVGM GSSTLLTRQP APLSQKQRSF VTFRGEPAEG FNHLVVDERT   60
GHIYLGAVNR IYKLSSDLKV LVTHETGPDE DNPKCYPPRI VQTCNEPLTT TNNVNKMLLI   120
DYKENRLIAC GSLYQGICKL LRLEDLFKLG EPYHKKEHYL SGVNESGSVF GVIVSYSNLD   180
DKLFIATAVD GKPEYFPTIS SRKLTKNSEA DGMFAYVFHD EFVASMIKIP SDTFTIIPDF   240
DIYYVYGFSS GNFVYFLTLQ PEMVSPPGST TKEQVYTSKL VRLCKEDTAF NSYVEVPIGC   300
ERSGVEYRLL QAAYLSKAGA VLGRTLGVHP DDDLLFTVFS KGQKRKMKSL DESALCIFIL   360
KQINDRIKER LQSCYRGEGT LDLAWLKVKD IPCSSALLTI DDNFCGLDMN APLGVSDMVR   420
GIPVFTEDRD RMTSVIAYVY KNHSLAFVGT KSGKLKKIRV DGPRGNALQY ETVQVVDPGP   480
VLRDMAFSKD HEQLYIMSER QLTRVPVESC GQYQSCGECL GSGDPHCGWC VLHNTCTRKE   540
RCERSKEPRR FASEMKQCVR LTVHPNNISV SQYNVLLVLE TYNVPELSAG VNCTFEDLSE   600
MDGLVVGNQI QCYSPAAKEV PRIITENGDH HVVQLQLKSK ETGMTFASTS FVFYNCSVHN   660
SCLSCVESPY RCHWCKYRHV CTHDPKTCSF QEGRVKLPED CPQLLRVDKI LVPVEVIKPI   720
TLKAKNLPQP QSGQRGYECI LNIQGSEQRV PALRFNSSSV QCQNTSYSYE GMEINNLPVE   780
LTVVWNGHFN IDNPAQNKVH LYKCGAMRES CGLCLKADPD FACGWCQGPG QCTLRQHCPA   840
QESQWLELSG AKSKCTNPRI TEIIPVTGPR EGGTKVTIRG ENLGLEFRDI ASHVKVAGVE   900
CSPLVDGYIP AEQIVCEMGE AKPSQHAGFV EICVAVCRPE FMARSSQLYY FMTLTLSDLK   960
PSRGPMSGGT QVTITGTNLN AGSNVVVMFG KQPCLFHRRS PSYIVCNTTS SDEVLEMKVS   1020
VQVDRAKIHQ DLVFQYVEDP TIVRIEPEWS IVSGNTPIAV WGTHLDLIQN PQIRAKHGGK   1080
EHINICEVLN ATEMTCQAPA LALGPDHQSD LTERPEEFGF ILDNVQSLLI LNKTNFTYYP   1140
NPVFEAFGPS GILELKPGTP IILKGKNLIP PVAGGNVKLN YTVLVGEKPC TVTVSDVQLL   1200
CESPNLIGRH KVMARVGGME YSPGMVYIAP DSPLSLPAIV SIAVAGGLLI IFIVAVLIAY   1260
KRKSRESDLT LKRLQMQMDN LESRVALECK EAFAELQTDI HELTSDLDGA GIPFLDYRTY   1320
TMRVLFPGIE DHPVLRDLEV PGYRQERVEK GLKLFAQLIN NKVFLLSFIR TLESQRSFSM   1380
RDRGNVASLI MTVLQSKLEY ATDVLKQLLA DLIDKNLESK NHPKLLLRRT ESVAEKMLTN   1440
WFTFLLYKFL KECAGEPLFS LFCAIKQQME KGPIDAITGE ARYSLSEDKL IRQQIDYKTL   1500
VLSCVSPDNA NSPEVPVKIL NCDTITQVKE KILDAIFKNV PCSHRPKAAD MDLEWRQGSG   1560
ARMILQDEDI TTKIENDWKR LNTLAHYQVP DGSVVALVSK QVTAYNAVNN STVSRTSASK   1620
YENMIRYTGS PDSLRSRTPM ITPDLESGVK MWHLVKNHEH GDQKEGDRGS KMVSEIYLTR   1680
LLATKGTLQK FVDDLFETIF STAHRGSALP LAIKYMFDFL DEQADKHGIH DPHVRHTWKS   1740
NCLPLRFWVN MIKNPQFVFD IHKNSITDAC LSVVAQTFMD SCSTSEHRLG KDSPSNKLLY   1800
AKDIPSYKNW VERYYSDIGK MPAISDQDMN AYLAEQSRMH MNEFNTMSAL SEIFSYVGKY   1860
SEEILGPLDH DDQCGKQKLA YKLEQVITLM SLDS                              1894
```

```
SEQ ID NO: 93          moltype = AA  length = 184
FEATURE                Location/Qualifiers
source                 1..184
                       mol_type = protein
                       organism = Homo sapiens
SEQUENCE: 93
PVPPGEDSKD VAAPHRQPLT SSERIDKQIR YILDGISALR KETCNKSNMC ESSKEALAEN   60
NLNLPKMAEK DGCFQSGFNE ETCLVKIITG LLEFEVYLEY LQNRFESSEE QARAVQMSTK   120
VLIQFLQKKA KNLDAITTPD PTTNASLLTK LQAQNQWLQD MTTHLILRSF KEFLQSSLRA   180
LRQM                                                               184
```

```
SEQ ID NO: 94          moltype = AA  length = 306
FEATURE                Location/Qualifiers
source                 1..306
```

-continued

```
                          mol_type = protein
                          organism = Homo sapiens
SEQUENCE: 94
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                             306

SEQ ID NO: 95            moltype = AA   length = 114
FEATURE                  Location/Qualifiers
source                   1..114
                         mol_type = protein
                         organism = Homo sapiens
SEQUENCE: 95
MNWVNVISDL KKIEDLIQSM HIDATLYTES DVHPSCKVTA MKCFLLELQV SLESGDASIH   60
DTVENLIILA NNSLSSNGNV TESGCKECEE LEEKNIKEFL QSFVHIVQMF INTS         114

SEQ ID NO: 96            moltype = AA   length = 137
FEATURE                  Location/Qualifiers
source                   1..137
                         mol_type = protein
                         organism = Homo sapiens
SEQUENCE: 96
MIVKAGITIP RNPGCPNSED KNFPRTVMVN LNIHNRNTNT NPKRSSDYYN RSTSPWNLHR   60
NEDPERYPSV IWEAKCRHLG CINADGNVDY HMNSVPIQQE ILVLRREPPH CPNSFRLEKI   120
LVSVGCTCVT PIVHHVA                                                 137

SEQ ID NO: 97            moltype = AA   length = 153
FEATURE                  Location/Qualifiers
source                   1..153
                         mol_type = protein
                         organism = Homo sapiens
SEQUENCE: 97
MRPSGRKSSK MQAFRIWDVN QKTFYLRNNQ LVAGYLQGPN VNLEEKIDVV PIEPHALFLG   60
IHGGKMCLSC VKSGDETRLQ LEAVNITDLS ENRKQDKRFA FIRSDSGPTT SFESAACPGW   120
FLCTAMEADQ PVSLTNMPDE GVMVTKFYFQ EDE                               153

SEQ ID NO: 98            moltype = AA   length = 162
FEATURE                  Location/Qualifiers
source                   1..162
                         mol_type = protein
                         organism = Homo sapiens
SEQUENCE: 98
MDSVCPQGKY IHPQNNSICC TKCHKGTYLY NDCPGPGQDT DCRECESGSF TASENHLRHC   60
LSCSKCRKEM GQVEISSCTV DRDTVCGCRK NQYRHYWSEN LFQCFNCSLC LNGTVHLSCQ   120
EKQNTVCTCH AGFFLRENEC VSCSNCKKSL ECTKLCLPQI EN                     162

SEQ ID NO: 99            moltype = AA   length = 165
FEATURE                  Location/Qualifiers
source                   1..165
                         mol_type = protein
                         organism = Homo sapiens
SEQUENCE: 99
APMAEGGGQN HHEVVKFMDV YQRSYCHPIE TLVDIFQEYP DEIEYIFKPS CVPLMRCGGC   60
CNDEGLECVP TEESNITMQI MRIKPHQGQH IGEMSFLQHN KCECRPKKDR ARQENPCGPC   120
SERRKHLFVQ DPQTCKCSCK NTDSRCKARQ LELNERTCRC DKPRR                  165

SEQ ID NO: 100           moltype = AA   length = 673
FEATURE                  Location/Qualifiers
source                   1..673
                         mol_type = protein
                         organism = Homo sapiens
SEQUENCE: 100
FKIETTPESR YLAQIGDSVS LTCSTTGCES PFFSWRTQID SPLNGKVTNE GTTSTLTMNP   60
VSFGNEHSYL CTATCESRKL EKGIQVEIYS FPKDPEIHLS GPLEAGKPIT VKCSVADVYP   120
FDRLEIDLLK GDHLMKSQEF LEDADRKSLE TKSLEVTFTP VIEDIGKVLV CRAKLHIDEM   180
DSVPTVRQAV KELQVYISPK NTVISVNPST KLQEGGSVTM TCSSEGLPAP EIFWSKKLDN   240
GNLQHLSGNA TLTLIAMRME DSGIYVCEGV NLIGKNRKEV ELIVQEKPFT VEISPGPRIA   300
AQIGDSVMLT CSVMGCESPS FSWRTQIDSP LSGKVRSEGT NSTLTLSPVS FENEHSYLCT   360
VTCGHKKLEK GIQVELYSFP RDPEIEMSGG LVNGSSVTVS CKVPSVYPLD RLEIELLKGE   420
TILENIEFLE DTDMKSLENK SLEMTFIPTI EDTGKALVCQ AKLHIDDMEF EPKQRQSTQT   480
LYVNVAPRDT TVLVSPSSIL EEGSSVNMTC LSQGFPAPKI LWSRQLPNGE LQPLSENATL   540
TLISTKMEDS GVYLCEGINQ AGRSRKEVEL IIQVTPKDIK LTAFPSESVK EGDTVIISCT   600
CGNVPETWII LKKKAETGDT VLKSIDGAYT IRKAQLKDAG VYECESKNKV GSQLRSLTLD   660
VQGRENNKDY FSP                                                     673

SEQ ID NO: 101           moltype = AA   length = 466
```

-continued

```
FEATURE          Location/Qualifiers
source           1..466
                 mol_type = protein
                 organism = Homo sapiens
SEQUENCE: 101
MVSQALRLLC LLLGLQGCLA AGGVAKASGG ETRDMPWKPG PHRVFVTQEE AHGVLHRRRR   60
ANAFLEELRP GSLERECKEE QCSFEEAREI FKDAERTKLF WISYSDGDQC ASSPCQNGGS  120
CKDQLQSYIC FCLPAFEGRN CETHKDDQLI CVNENGGCEQ YCSDHTGTKR SCRCHEGYSL  180
LADGVSCTPT VEYPCGKIPI LEKRNASKPQ GRIVGGKVCP KGECPWQVLL LVNGAQLCGG  240
TLINTIWVVS AAHCFDKIKN WRNLIAVLGE HDLSEHDGDE QSRRVAQVII PSTYVPGTTN  300
HDIALLRLHQ PVVLTDHVVP LCLPERTFSE RTLAFVRFSL VSGWGQLLDR GATALELMVL  360
NVPRLMTQDC LQQSRKVGDS PNITEYMFCA GYSDGSKDSC KGDSGGPHAT HYRGTWYLTG  420
IVSWGQGCAT VGHFGVYTRV SQYIEWLQKL MRSEPRPGVL LRAPFP             466

SEQ ID NO: 102       moltype = AA  length = 1487
FEATURE          Location/Qualifiers
source           1..1487
                 mol_type = protein
                 organism = Homo sapiens
SEQUENCE: 102
MIRLGAPQTL VLLTLLVAAV LRCQGQDVQE AGSCVQDGQR YNDKDVWKPE PCRICVCDTG   60
TVLCDDIICE DVKDCLSPEI PFGECCPICP TDLATASGQP GPKGQKGEPG DIKDIVGPKG  120
PPGPQGPAGE QGPRGDRGDK GEKGAPGPRG RDGEPGTPGN PGPPGPPGPP GPPGLGGNFA  180
AQMAGGFDEK AGGAQLGVMQ GPMGPMGPRG PPGPAGAPGP QGPQGNPGEP GEPGVSGPMG  240
PRGPPGPPGK PGDDGEAGKP GKAGERGPPG PQGRARGFPGT PGLPGVKGHR GYPGLDGAKG  300
EAGAPGVKGE SGSPGENGSP GPMGPRGLPG ERGRTGPAGA AGARGNDGQP GPAGPPGPVG  360
PAGGPGFPGA PGAKGEAGPT GARGPEGAQG PRGEPGTPGS PGPAGASGNP GTDGIPGAKG  420
SAGAPGIAGA PGFPGPRGPP GPQGATGPLG PKGQTGEPGI AGFKGEQGPK GEPGPAGPQG  480
APGPAGEEGK RGARGEPGGV GPIGPPGERG APGNRGFPGQ DGLAGPKGAP GERGPSGLAG  540
PKGANGDPGR PGEPGLPGAR GLTGRPGDAG PQGKVGPSGA PGEDGRPGPP GPQGARGQPG  600
VMGFPGPKGA NGEPGKAGEK GLPGAPGLRG LPGKDGETGA AGPPGPAGPA GERGEQGAPG  660
PSGFQGLPGP PGPPGEGGKP GDQGVPGEAG APGLVGPRGE RGPPGERGSP GAQGLQGPRG  720
LPGTPGTDGP KGASGPAGPP GAQGPPGLQG MPGERGAAGI AGPKGDRGDV GEKGPEGAPG  780
KDGGRGLTGP IGPPGPAGAN GEKGEVGPPG PAGSAGARGA PGERGETGPP GPAGFAGPPG  840
ADGQPGAKGE QGEAGQKGDA GAPGPQGPSG APGPQGPTGV TGPKGARGAQ GPPGATGFPG  900
AAGRVGPPGS NGNPGPPGPP GPSGKDGPKG ARGDSGPPGR AGEPGLQGPA GPPGEKGEPG  960
DDGPSGAEGP PGPQGLAGQR GIVGLPGQRG ERGFPGLPGP SGEPGKQGAP GASGDRGPPG 1020
PVGPPGLTGP AGEPGREGSP GADGPPGRDG AAGVKGDRGE TGAVGAPGAP GPPGSPGPAG 1080
PTGKQGDRGE AGAQGPMGPS GPAGARGIQG PQGPRGDKGE AGEPGERGLK GHRGFTGLQG 1140
LPGPPGPSGD QGASGPAGPS GPRGPPGPVG PSGKDGANGI PGPIGPPGPR GRSGETGPAG 1200
PPGNPGPPGP PGPPGPGIDM SAFAGLGPRE KGPDPLQYMR ADQAAGGLRQ HDAEVDATLK 1260
SLNNQIESIR SPEGSRKNPA RTCRDLKLCH PEWKSGDYWI DPNQGCTLDA MKVFCNMETG 1320
ETCVYPNPAN VPKKNWWSSK SKEKKHIWFG ETINGGFHFS YGDDNLAPNT ANVQMTFLRL 1380
LSTEGSQNIT YHCKNSIAYL DEAAGNLKKA LLIQGSNDVE IRAEGNSRFT YTALKDGCTK 1440
HTGKWGKTVI EYRSQKTSRL PIIDIAPMDI GGPEQEFGVD IGPVCFL             1487

SEQ ID NO: 103       moltype = AA  length = 119
FEATURE          Location/Qualifiers
source           1..119
                 mol_type = protein
                 organism = Homo sapiens
SEQUENCE: 103
MSRSVALAVL ALLSLSGLEA IQRTPKIQVY SRHPAENGKS NFLNCYVSGF HPSDIEVDLL   60
KNGERIEKVE HSDLSFSKDW SFYLLYYTEF TPTEKDEYAC RVNHVTLSQP KIVKWDRDM   119

SEQ ID NO: 104       moltype = AA  length = 53
FEATURE          Location/Qualifiers
source           1..53
                 mol_type = protein
                 organism = Homo sapiens
SEQUENCE: 104
EQAPGTAPCS RGSSWSADLD KCMDCASCRA RPHSDFCLGC AAAPPAPFRL LWP           53

SEQ ID NO: 105       moltype = AA  length = 174
FEATURE          Location/Qualifiers
source           1..174
                 mol_type = protein
                 organism = Homo sapiens
SEQUENCE: 105
MAPEPGSTCR LREYYDQTAQ MCCSKCSPGQ HAKVFCTKTS DTVCDSCEDS TYTQLWNWVP   60
ECLSCGSRCS SDQVETQACT REQNRICTCR PGWYCALSKQ EGCRLCAPLR KCRPGFGVAR  120
PGTETSDVVC KPCAPGTFSN TTSSTDICRP HQICNVVAIP GNASMDAVCT STSP          174

SEQ ID NO: 106       moltype = AA  length = 102
FEATURE          Location/Qualifiers
source           1..102
                 mol_type = protein
                 organism = Homo sapiens
SEQUENCE: 106
```

```
MEKLLCFLVL TSLSHAFGQT DMSRKAFVFP KESDTSYVSL KAPLTKPLKA FTVCLHFYTE  60
LSSTHEINTI YLGGPFSPNV LNWRALKYEV QGEVFTKPQL WP                     102

SEQ ID NO: 107          moltype = AA  length = 76
FEATURE                 Location/Qualifiers
source                  1..76
                        mol_type = protein
                        organism = Homo sapiens
SEQUENCE: 107
MRRGPRSLRG RDAPAPTPCV PAECFDLLVR HCVACGLLRT PRPKPAGASS PAPRTALQPQ  60
ESVGAGAGEA ALPLPG                                                  76

SEQ ID NO: 108          moltype = AA  length = 152
FEATURE                 Location/Qualifiers
source                  1..152
                        mol_type = protein
                        organism = Homo sapiens
SEQUENCE: 108
AVQGPEETVT QDCLQLIADS ETPTIQKGSY TFVPWLLSFK RGSALEEKEN KILVKETGYF  60
FIYGQVLYTD KTYAMGHLIQ RKKVHVFGDE LSLVTLFRCI QNMPETLPNN SCYSAGIAKL  120
EEGDELQLAI PRENAQISLD GDVTFFGALK LL                                152

SEQ ID NO: 109          moltype = AA  length = 31
FEATURE                 Location/Qualifiers
source                  1..31
                        mol_type = protein
                        organism = Homo sapiens
SEQUENCE: 109
HAEGTFTSDV SSYLEGQAAK EFIAWLVKGR G                                 31

SEQ ID NO: 110          moltype = AA  length = 733
FEATURE                 Location/Qualifiers
source                  1..733
                        mol_type = protein
                        organism = Homo sapiens
SEQUENCE: 110
MPEETQAQDQ PMEEEEVETF AFQAEIAQLM SLIINTFYSN KEIFLRELIS NSSDALDKIR  60
YESLTDPSKL DSGKELHINL IPNKQDRTLT IVDTGIGMTK ADLINNLGTI AKSGTKAFME  120
ALQAGADISM IGQFGVGFYS AYLVAEKVTV ITKHNDDEQY AWESSAGGSF TVRTDTGEPM  180
GRGTKVILHL KEDQTEYLEE RRIKEIVKKH SQFIGYPITL FVEKERDKEV SDDEAEEKED  240
KEEEKEKEEK ESDDKPEIED VGSDEEEEEK KDGDKKKKKK IKEKYIDQEE LNKTKPIWTR  300
NPDDITNEEY GEFYKSLTND WEDHLAVKHF SVEGQLEFRA LLFVPRRAPF DLFENRKKKN  360
NIKLYVRRVF IMDNCEELIP EYLNFIRGVV DSEDLPLNIS REMLQQSKIL KVIRKNLVKK  420
CLELFTELAE DKENYKKFYE QFSKNIKLGI HEDSQNRKKL SELLRYYTSA SGDEMVSLKD  480
YCTRMKENQK HIYYITGETK DQVANSAFVE RLRKHGLEVI YMIEPIDEYC VQQLKEFEGK  540
TLVSVTKEGL ELPEDEEEKK KQEEKKTKFE NLCKIMKDIL EKKVEKVVVS NRLVTSPCCI  600
VTSTYGWTAN MERIMKAQAL RDNSTMGYMA AKKHLEINPD HSIIETLRQK AEADKNDKSV  660
KDLVILLYET ALLSSGFSLE DPQTHANRIY RMIKLGLGID EDDPTADDSS AAVTEEMPPL  720
EGDDDTSRME EVD                                                     733

SEQ ID NO: 111          moltype = AA  length = 53
FEATURE                 Location/Qualifiers
source                  1..53
                        mol_type = protein
                        organism = Homo sapiens
SEQUENCE: 111
NSDSECPLSH DGYCLHDGVC MYIEALDKYA CNCVVGYIGE RCQYRDLKWW ELR         53

SEQ ID NO: 112          moltype = AA  length = 1744
FEATURE                 Location/Qualifiers
source                  1..1744
                        mol_type = protein
                        organism = Homo sapiens
SEQUENCE: 112
MRLLWGLIWA SSFFTLSLQK PRLLLFSPSV VHLGVPLSVG VQLQDVPRGQ VVKGSVFLRN  60
PSRNNVPCSP KVDFTLSSER DFALLSLQVP LKDAKSCGLH QLLRGPEVQL VAHSPWLKDS  120
LSRTTNIQGI NLLFSSRRGH LFLQTDQPIY NPGQRVRYRV FALDQKMRPS TDTITVMVEN  180
SHGLRVRKKE VYMPSSIFQD DFVIPDISEP GTWKISARFS DGLESNSSTQ FEVKKYVLPN  240
FEVKITPGKP YILTVPGHLD EMQLDIQARY IYGKPVQGVA YVRFGLLDED GKKTFFRGLE  300
SQTKLVNGQS HISLSKAEFQ DALEKLNMGI TDLQGLRLYV AAAIIESPGG EMEEAELTSW  360
YFVSSPFSLD LSKTKRHLVP GAPFLLQALV REMSGSPASG IPVKVSATVS SPGSVPEVQD  420
IQQNTDGSGQ VSIPIIIPQT ISELQLSVSA GSPHPAIARL TVAAPPSGGP GFLSIERPDS  480
RPPRVGDTLN LNLRAVGSGA TFSHYYYMIL SRGQIVFMNR EPKRTLTSVS VFVDHHLAPS  540
FYFVAFYYHG DHPVANSLRV DVQAGACEGK LELSVDGAKQ YRNGESVKLH LETDSLALVA  600
LGALDTALYA AGSKSHKPLN MGKVFEAMNS YDLGCGPGGG DSALQVFQAA GLAFSDGDQW  660
TLSRKRLSCP KEKTTRKKRN VNFQKAINEK LGQYASPTAK RCCQDGVTRL PMMRSCEQRA  720
ARVQQPDCRE PFLSCCQFAE SLRKKSRDKG QAGLQRALEI LQEEDLIDED DIPVRSFFPE  780
NWLWRVETVD RFQILTLWLP DSLTTWEIHG LSLSKTKGLC VATPVQLRVF REFHLHLRLP  840
MSVRRFEQLE LRPVLYNYLD KNLTVSVHVS PVEGLCLAGG GGLAQQVLVP AGSARPVAFS  900
```

```
VVPTAAAAVS LKVVARGSFE FPVGDAVSKV LQIEKEGAIH REELVYELNP LDHRGRTLEI    960
PGNSDPNMIP DGDFNSYVRV TASDPLDTLG SEGALSPGGV ASLLRLPRGC GEQTMIYLAP   1020
TLAASRYLDK TEQWSTLPPE TKDHAVDLIQ KGYMRIQQFR KADGSYAAWL SRDSSTWLTA   1080
FVLKVLSLAQ EQVGGSPEKL QETSNWLLSQ QQADGSFQDP CPVLDRSMQG GLVGNDETVA   1140
LTAFVTIALH HGLAVFQDEG AEPLKQRVEA SISKANSFLG EKASAGLLGA HAAAITAYAL   1200
TLTKAPVDLL GVAHNNLMAM AQETGDNLYW GSVTGSQSNA VSPTPAPRNP SDPMPQAPAL   1260
WIETTAYALL HLLLHEGKAE MADQASAWLT RQGSFQGGFR STQDTVIALD ALSAYWIASH   1320
TTEERGLNVT LSSTGRNGFK SHALQLNNRQ IRGLEEELQF SLGSKINVKV GGNSKGTLKV   1380
LRTYNVLDMK NTTCQDLQIE VTVKGHVEYT MEANEDYEDY EYDELPAKDD PDAPLQPVTP   1440
LQLFEGRRNR RRREAPKVVE EQESRVHYTV CIWRNGKVGL SGMAIADVTL LSGFHALRAD   1500
LEKLTSLSDR YVSHFETEGP HVLLYFDSVP TSRECVGFEA VQEVPVGLVQ PASATLYDYY   1560
NPERRCSVFY GAPSKSRLLA TLCSAEVCQC AEGKCPRQRR ALERGLQDED GYRMKFACYY   1620
PRVEYGFQVK VLREDSRAAF RLFETKITQV LHFTKDVKAA ANQMRNFLVR ASCRLRLEPG   1680
KEYLIMGLDG ATYDLEGHPQ YLLDSNSWIE EMPSERLCRS TRQRAACAQL NDFLQEYGTQ   1740
GCQV                                                                1744

SEQ ID NO: 113          moltype = AA  length = 1663
FEATURE                 Location/Qualifiers
source                  1..1663
                        mol_type = protein
                        organism = Homo sapiens
SEQUENCE: 113
MGPTSGPSLL LLLLTHLPLA LGSPMYSIIT PNILRLESEE TMVLEAHDAQ GDVPVTVTVH    60
DFPGKKLVLS SEKTVLTPAT NHMGNVTFTI PANREFKSEK GRNKFVTVQA TFGTQVVEKV   120
VLVSLQSGYL FIQTDKTIYT PGSTVLYRIF TVNHKLLPVG RTVMVNIENP EGIPVKQDSL   180
SSQNQLGVLP LSWDIPELVN MGQWKIRAYY ENSPQQVFST EFEVKEYVLP SFEVIVEPTE   240
KFYYIYNEKG LEVTITARFL YGKKVEGTAF VIFGIQDGEQ RISLPESLKR IPIEDGSGEV   300
VLSRKVLLDG VQNPRAEDLV GKSLYVSATV ILHSGSDMVQ AERSGIPIVT SPYQIHFTKT   360
PKYFKPGMPF DLMVFVTNPD GSPAYRVPVA VQGEDTVQSL TQGDGVAKLS INTHPSQKPL   420
SITVRTKKQE LSEAEQATRT MQALPYSTVG NSNNYLHLSV LRTELRPGET LNVNFLLRMD   480
RAHEAKIRYY TYLIMNKGRL LKAGRQVREP GQDLVVLPLS ITTDFIPSFR LVAYYTLIGA   540
SGQREVVADS VWVDVKDSCV GSLVVKSGQS EDRQPVPGQQ MTLKIEGDHG ARVVLVAVDK   600
GVFVLNKKNK LTQSKIWDVV EKADIGCTPG SGKDYAGVFS DAGLTFTSSS GQQTAQRAEL   660
QCPQPAARRR RSVQLTEKRM DKVGKYPKEL RKCCEDGMRE NPMRFSCQRR TRFISLGEAC   720
KKVFLDCCNY ITELRRQHAR ASHLGLARSN LDEDIIAAEN IVSRSEFPES WLWNVEDLKE   780
PPKNGISTKL MNIFLKDSIT TWEILAVSMS DKKGICVADP FEVTVMQDFF IDLRLPYSVV   840
RNEQVEIRAV LYNYRQNQEL KVRVELLHNP AFCSLATTKR RHQQTVTIPP KSSLSVPYVI   900
VPLKTGLQEV EVKAAVYHHF ISDGVRKSLK VVPEGIRMNK TVAVRTLDPE RLGREGVQKE   960
DIPPADLSDQ VPDTESETRI LLQGTPVAQM TEDAVDAERL KHLIVTPSGC GEQNMIGMTP   1020
TVIAVHYLDE TEQWEKFGLE KRQGALELIK KGYTQQLAFR QPSSAFAAFV KRAPSTWLTA   1080
YVVKVFSLAV NLIAIDSQVL CGAVKWLILE KQKPDGVFQE DAPVIHQEMI GGLRNNNEKD   1140
MALTAFVLIS LQEAKDICEE QVNSLPGSIT KAGDFLEANY MNLQRSYTVA IAGYALAQMG   1200
RLKGPLLNKF LTTAKDKNRW EDPGKQLYNV EATSYALLAL LQLKDFDFVP PVVRWLNEQR   1260
YYGGGYGSTQ ATFMVFQALA QYQKDAPDHQ ELNLDVSLQL PSRSSKITHR IHWESASLLR   1320
SEETKENEGF TVTAEGKGQG TLSVVTMYHA KAKDQLTCNK FDLKVTIKPA PETEKRPQDA   1380
KNTMILEICT RYRGDQDATM SILDISMMTG FAPDTDDLKQ LANGVDRYIS KYELDKAFSD   1440
RNTLIIYLDK VSHSEDDCLA FKVHQYFNVE LIQPGAVKVY AYYNLEESCT RFYHPEKEDG   1500
KLNKLCRDEL CRCAEENCFI QKSDDKVTLE ERLDKACEPG VDYVYKTRLV KVQLSNDFDE   1560
YIMAIEQTIK SGSDEVQVGQ QRTFISPIKC REALKLEEKK HYLMWGLSSD FWGEKPNLSY   1620
IIGKDTWVEH WPEEDECQDE ENQKQCQDLG AFTESMVVFG CPN                     1663

SEQ ID NO: 114          moltype = AA  length = 245
FEATURE                 Location/Qualifiers
source                  1..245
                        mol_type = protein
                        organism = Homo sapiens
SEQUENCE: 114
MEGPRGWLVL CVLAISLASM VTEDLCRAPD GKKGEAGRPG RRGRPGLKGE QGEPGAPGIR    60
TGIQGLTKGDQ GEPGPSGNPG KVGYPGPSGP LGARGIPGGK LGKGSPGNIK DQPRPAFSAI   120
RRNPPMGGNV VIFDTVITNQ EEPYQNHSGR FVCTVPGYYY FTFQVLSQWE ICLSIVSSSR   180
GQVRRSLGFC DTTNKGLFQV VSGGMVLQLQ QGDQVWVEKD PKKGHIYQGS EADSVFSGFL   240
IFPSA                                                               245

SEQ ID NO: 115          moltype = AA  length = 866
FEATURE                 Location/Qualifiers
source                  1..866
                        mol_type = protein
                        organism = Homo sapiens
SEQUENCE: 115
MFSMRIVCLV LSVVGTAWTA DSGEGDFLAE GGGVRGPRVV ERHQSACKDS DWPFCSDEDW    60
NYKCPSGCRM KGLIDEVNQD FTNRINKLKN SLFEYQKNNK DSHSLTTNIM EILRGDFSSA   120
NNRDNTYNRV SEDLRSRIEV LKRKVIEKVQ HIQLLQKNVR AQLVDMKRLE VDIDIKIRSC   180
RGSCSRALAR EVDLKDYEDQ QKQLEQVIAK DLLPSRDRQH LPLIKMKPVP DLVPGNFKSQ   240
LQKVPPEWKA LTDMPQMRME LERPGGNEIT RGGSTSYGTG SETESPRNPS SAGSWNSGSS   300
GPGSTGNRNP GSSGTGGTAT WKPGSSGPGS TGSWNSGSSG TGSTGNQNPG SPRPGSTGTW   360
NPGSSERGSA GHWTSESSVS GSTGQWHSES GSFRPDSPGS GNARPNNPDW GTFEEVSGNV   420
SPGTRREYHT EKLVTSKGDK ELRTGKEKVT SGSTTTTRRS CSKTVTKTVI GPDGHKEVTK   480
EVVTSEDGSD CPEAMDLGTL SGIGTLDGFR HRHPDEAAFF DTASTGKTFP GFFSPMLGEF   540
VSETESRGSE SGIFTNTKES SSHHPGIAEF PSRGKSSSYS KQFTSSTSYN RGDSTFESKS   600
```

-continued

```
YKMADEAGSE ADHEGTHSTK RGHAKSRPVR DCDDVLQTHP SGTQSGIFNI KLPGSSKIFS   660
VYCDQETSLG GWLLIQQRMD GSLNFNRTWQ DYKRGFGSLN DEGEGEFWLG NDYLHLLTQR   720
GSVLRVELED WAGNEAYAEY HFRVGSEAEG YALQVSSYEG TAGDALIEGS VEEGAEYTSH   780
NNMQFSTFDR DADQWEENCA EVYGGGWWYN NCQAANLNGI YYPGGSYDPR NNSPYEIENG   840
VVWVSFRGAD YSLRAVRMKI RPLVTQ                                        866
```